US012616840B2

(12) United States Patent
Berényi et al.

(10) Patent No.: US 12,616,840 B2
(45) Date of Patent: May 5, 2026

(54) SYSTEMS AND METHODS FOR SEIZURE DETECTION AND CLOSED-LOOP NEUROSTIMULATION

(71) Applicant: Blackrock Microsystems, Inc., Salt Lake City, UT (US)

(72) Inventors: Antal Berényi, Szeged (HU); Tamás Kurics, Budapest (HU); Miklós Bence, Budapest (HU); Máté Németh, Kistarcsa (HU); Tamás Laszlovszky, Pomáz (HU); Mihály Nádasdi, Maglód (HU); Péter Ráfi, Budapest (HU); Viktor Vincze, Szentes (HU); Szabolcs Hőgye, Budapest (HU)

(73) Assignee: Blackrock Microsystems, Inc., Salt Lake City, UT (US)

( * ) Notice: Subject to any disclaimer, the term of this patent is extended or adjusted under 35 U.S.C. 154(b) by 0 days.

(21) Appl. No.: 18/981,252

(22) Filed: Dec. 13, 2024

(65) Prior Publication Data

US 2025/0195894 A1      Jun. 19, 2025

Related U.S. Application Data

(60) Provisional application No. 63/610,955, filed on Dec. 15, 2023.

(51) Int. Cl.
*A61N 1/36*          (2006.01)
*A61N 1/372*         (2006.01)

(52) U.S. Cl.
CPC ..... *A61N 1/36139* (2013.01); *A61N 1/36064* (2013.01); *A61N 1/36171* (2013.01); *A61N 1/37235* (2013.01)

(58) Field of Classification Search
None
See application file for complete search history.

(56) References Cited

U.S. PATENT DOCUMENTS 6,248,126 B1    6/2001 Lesser et al.
6,547,746 B1 *  4/2003 Marino .................. A61B 5/377
                                                600/545

(Continued)

FOREIGN PATENT DOCUMENTS

WO    WO-1999034758 A1    7/1999
WO    WO-2005058135 A2    6/2005
WO    WO-2022226606 A1    11/2022

OTHER PUBLICATIONS

International Search Report and Written Opinion for International Application No. PCT/US2024/060196, by Blackrock Microsystems, Inc., mailed Mar. 6, 2025; 15 pages.

(Continued)

*Primary Examiner* — Benjamin J Klein
*Assistant Examiner* — Willow Grace Welch
(74) *Attorney, Agent, or Firm* — COOLEY LLP

(57)          ABSTRACT

Embodiments described herein relate to systems, devices, and methods for monitoring brain activity and delivering electrical brain stimulation to a patient. In some embodiments, a system can deliver responsive electrical stimulation in a closed-loop manner and can offer real-time or near real-time monitoring of induced neurophysiological effects. After detecting a targeted brain pattern (i.e., an epileptic seizure), the system may deliver high-intensity ultra-short electrical stimulation impulses non-invasively or minimal-invasively to diminish or stop the neural oscillations underlying the epileptic seizure. The stimuli are delivered in time and space, relative to the emerging seizure rhythm patterns, such that they diminish or terminate the seizure. The system may include an implantable device including one or more electrodes electrically coupled to one or more processors. The processor(s) may be operatively coupled to a memory, (Continued)

one or more communication modules, and may optionally be coupled to a battery and one or more additional sensor(s).

29 Claims, 43 Drawing Sheets

(56)                    References Cited

U.S. PATENT DOCUMENTS

| | | | |
|---|---|---|---|
| 8,849,369 | B2 | 9/2014 | Cogan et al. |
| 8,934,965 | B2 | 1/2015 | Rogers et al. |
| 9,072,887 | B2 | 7/2015 | Kagan et al. |
| 10,349,860 | B2 | 7/2019 | Rogers et al. |
| 10,743,809 | B1 * | 8/2020 | Kamousi ............. A61B 5/4848 |
| 11,317,850 | B2 | 5/2022 | Gu et al. |
| 2005/0256418 | A1 * | 11/2005 | Mietus ................. A61B 5/4818 |
| | | | 600/512 |
| 2016/0029946 | A1 * | 2/2016 | Simon .................. A61B 5/7203 |
| | | | 600/544 |
| 2016/0144186 | A1 | 5/2016 | Kaemmerer et al. |
| 2016/0228705 | A1 * | 8/2016 | Crowder ............ A61N 1/36064 |
| 2017/0196497 | A1 * | 7/2017 | Ray .......................... G06N 7/01 |
| 2018/0008835 | A1 * | 1/2018 | Nakagawa ........... A61N 1/3987 |
| 2019/0160287 | A1 | 5/2019 | Harrer et al. |
| 2020/0164201 | A1 * | 5/2020 | Berenyi ............... A61N 1/0476 |
| 2021/0353224 | A1 * | 11/2021 | Etkin ..................... G16H 30/40 |

OTHER PUBLICATIONS

Akbarian, B., et al., "Research Paper: Automatic Seizure Detection Based on Nonlinear Dynamical Analysis of EEG Signals and Mutual Information," Basic and Clinical Neuroscience, [Epub Jul. 1, 2018]; Jul.-Aug. 2018, 9(4), pp. 227-240.

Alekseichuk, I., et al., "Electric field dynamics in the brain during multi-electrode transcranial electric stimulation," Nature Communications, Jun. 12, 2019, 10(1):2573; 10 pages.

Arrais Junior, E., et al., "Real-time premature ventricular contractions detection based on Redundant Discrete Wavelet Transform," Research on Biomedical Engineering, Sep. 2018, 34(3), pp. 187-197.

Baumgartner, C., et al., "Automatic Computer-Based Detection of Epileptic Seizures," Frontiers in Neurology, Aug. 9, 2018, 9:639; 9 pages.

Beniczky, S., et al., "Automated real-time detection of tonic-clonic seizures using a wearable EMG device," Neurology Journals, [Epub Jan. 5, 2018]; Jan. 30, 2018, 90(5):e428-e434, pp. e1-e7.

Bergey, G. K., et al., "Long-term treatment with responsive brain stimulation in adults with refractory partial seizures," American Academy of Neurology, [Epub Jan. 23, 2015]; Feb. 24, 2015, 84(4), pp. 810-817.

Berényi, A., et al., "Closed-Loop Control of Epilepsy by Transcranial Electrical Stimulation," Science, Aug. 10, 2012, 337(6095), pp. 735-737.

Bikson, M., et al., "Rational modulation of neuronal processing with applied electric fields," Proceedings of the 28th Institute of Electrical and Electronics Engineers (IEEE) EMBS Annual International Conference in New York City, Aug. 30-Sep. 3, 2006. Published in 2006 International Conference of the IEEE Engineering in Medicine and Biology Society, 2006, pp. 1616-1619.

Boon, P., et al., "A prospective, multicenter study of cardiac-based seizure detection to activate vagus nerve stimulation," Seizure— European Journal of Epilepsy, Nov. 2015, vol. 32, pp. 52-61.

Carpenter, L. L., et al. "Transcranial Magnetic Stimulation (TMS) for Major Depression: A Multisite, Naturalistic, Observational Study of Acute Treatment Outcomes In Clinical Practice," Depression and Anxiety, Jun. 11, 2012, 29(7), pp. 587-596.

Chen, Z., et al., "Treatment Outcomes in Patients With Newly Diagnosed Epilepsy Treated With Established and New Antiepileptic Drugs: A 30-Year Longitudinal Cohort Study," JAMA Neurology, [Epub Dec. 26, 2017]; Mar. 2018, 75(3), pp. 279-286.

Chhatbar, P. Y., et al., "Evidence of transcranial direct current stimulation-generated electric fields at subthalamic level in human brain in vivo," Brain Stimulation, Mar. 13, 2018, 11(4), pp. 727-733.

Correa, A. G., et al. "Adaptive Filtering for Epileptic Event Detection in the EEG." Journal of Medical and Biological Engineering, Mar. 6, 2019, vol. 39, pp. 912-918.

Datta, A., et al., "Gyri-precise head model of transcranial direct current stimulation: improved spatial focality using a ring electrode versus conventional rectangular pad," Brain Stimulation, Oct. 2, 2009, pp. 201-207, 201.e1; 8 pages.

De O. Mota, H., et al., "Real-time wavelet transform algorithms for the processing of continuous streams of data," IEEE International Workshop on Intelligent Signal Processing, Faro, 2005, pp. 346-351.

Deng, Z., et al., "Coil design considerations for deep transcranial magnetic stimulation," Clinical Neurophysiology, [Epub Dec. 22, 2013]; Jun. 2014, 125(6), pp. 1202-1212.

Dmochowski, J. P., et al., "Targeted transcranial direct current stimulation for rehabilitation after stroke," NeuroImage, [Epub Mar. 5, 2013]; Jul. 15, 2013, vol. 75, pp. 12-19.

Duun-Henriksen, J., et al., "A new era in electroencephalographic monitoring? Subscalp devices for ultra-long-term recordings," Epilepsia, [Epub Aug. 27, 2020]; Sep. 2020, 61(9), pp. 1805-1817.

Farooq, M. S., et al., "Epileptic Seizure Detection Using Machine Learning: Taxonomy, Opportunities, and Challenges," Diagnostics, Mar. 10, 2013, 13(6):1058; 22 pages.

Fisher, R., et al., "Electrical stimulation of the anterior nucleus of thalamus for treatment of refractory epilepsy," Epilepsia, [Epub Apr. 22, 2010]; May 2010, 51(5), pp. 899-908.

Fürbaß, F., et al., "Combining Time Series and Frequency Domain Analysis for a Automatic Seizure Detection," 2012 Annual International Conference of the IEEE Engineering in Medicine and Biology Society, Nov. 10, 2012, pp. 1020-1023.

Fürbass, F., et al., "Prospective multi-center study of an automatic online seizure detection system for epilepsy monitoring units," Clinical Neurophysiology, [Epub Oct. 2, 2014]; Jun. 2015, 126(6):1124-1131.

Gabor, A. J., et al., "Automated seizure detection using a self-organizing neural network," Electroencephalography and Clinical Neurophysiology, Sep. 1996, 99(3), pp. 257-266.

Gabor, A.J., et al., "Seizure detection using a self-organizing neural network: validation and comparison with other detection strategies," Electroencephalography and Clinical Neurophysiology, [Epub Jun. 29, 1998]; Jul. 1998, 107(1), pp. 27-32.

Ganguly, T. M., et al., "Seizure Detection in Continuous Inpatient EEG," Neurology Journal, [Epub Apr. 11, 2022]; May 31, 2022, 98(22), pp. e2224-e2232.

Gel'Fand, I. M., et al., "Calculation of amount of information about a random function contained in another such function," American Mathematical Society Translations, Series 2,1959, pp. 199-246.

George, M. S., et al., "Daily Left Prefrontal Transcranial Magnetic Stimulation Therapy for Major Depressive Disorder," Arch Gen Psychiatry, May 2010, 67(5), pp. 507-516.

Gilron, R., et al., "Sleep-Aware Adaptive Deep Brain Stimulation Control: Chronic Use at Home With Dual Independent Linear Discriminate Detectors," Frontiers in Neuroscience, Oct. 18, 2021, 15(732499); 10 pages.

Gilron, R., et al., "Long-term wireless streaming of neural recordings for circuit discovery and adaptive stimulation in individuals with Parkinson's disease," Nature Biotechnology, [Epub May 3, 2021]; Sep. 2021, 39:1078-1085; 22 pages (including Methods and Reporting Summary).

Gotman, J., "Automatic seizure detection: improvements and evaluation," Electroencephalography and Clinical Neurophysiology, Oct. 1990, 76(4), pp. 317-324.

Grech, R., et al., "Review on solving the inverse problem in EEG source analysis," Journal of NeuroEngineering and Rehabilitation, Nov. 7, 2008, 5(25); 33 pages.

Griebel, G., et al., "50 years of hurdles and hope in anxiolytic drug discovery," Nature Reviews Drug Discovery, [Epub Aug. 30, 2013]; Sep. 2013, vol. 12, pp. 667-687.

(56)                    References Cited

OTHER PUBLICATIONS

Grossman, N., et al., "Noninvasive Deep Brain Stimulation via Temporally Interfering Electric Fields," Cell, Jun. 1, 2017, 169(6):1029-1041, e1-e17; 30 pages (including Graphical Abstract and Supplemental Figures).
Halford, J. J., et al., "Detection of generalized tonic-clonic seizures using surface electromyographic monitoring," Epilepsia, [Epub Oct. 5, 2017]; Nov. 2017, 54(11), pp. 1861-1869.
Halford, J. J., et al., "Standardized database development for EEG epileptiform transient detection: EEGnet scoring system and machine learning analysis," Journal of Neuroscience Methods, [Epub Nov. 19, 2012]; Jan. 30, 2013, 212(2), pp. 308-316.
Haneef, Z., et al., "Sub-scalp electroencephalography: A next-generation technique to study human neurophysiology," Clinical Neurophysiology, [Epub Jul. 18, 2022]; Sep. 2022, vol. 141, pp. 77-87.
Harangozo, M., et al., "Closed-loop implementation of intersectional short-pulse (ISP) stimulation to stop temporal lobe seizures," [abstract], Program No. 371.10/B85. 2019 Neuroscience Meeting Planner. Chicago, IL: Society for Neurosciences, 2019 [online]; 2 pages.
Harati, A., et al., "The TUH EEG CORPUS: A big data resource for automated EEG interpretation," 2014 IEEE Signal Processing in Medicine and Biology Symposium (SPMB), 2014, pp. 1-5.
Hartmann, M. M., et al., "EpiScan: Online seizure detection for epilepsy monitoring units," 33rd Annual International Conference of the IEEE Engineering in Medicine and Biology Society, 2011, pp. 6096-6099.
Hopfengärtner, R., et al., "An efficient, robust and fast method for the offline detection of epileptic seizures in long-term scalp EEG recordings," Clinical Neurophysiology, [Epub Sep. 21, 2007]; Nov. 2007, 118(11), pp. 2332-2343.
Hopfengärtner, R., et al., Automatic seizure detection in long-term scalp EEG using an adaptive thresholding technique: A validation study for clinical routine, Clinical Neurophysiology, [Epub Jan. 7, 2014]; Jul. 2014, 125(7), pp. 1346-1352.
Horvath, J. C., et al., "Quantitative Review Finds No Evidence of Cognitive Effects in Healthy Populations From Single-session Transcranial Direct Current Stimulation (tDCS)," Brain Stimulation, [Epub Jan. 16, 2015]; May-Jun. 2015, 8(3), pp. 535-550.
Huang, Y., et al., "Can transcranial electric stimulation with multiple electrodes reach deep targets?" Brain Stimulation, [Epub Sep. 26, 2018]; Jan.-Feb. 2019, 12(1), pp. 30-40.
Huang, Y., et al., "Measurements and models of electric fields in the in vivo human brain during transcranial electric stimulation," eLife, Feb. 7, 2017, 6:e18834; 26 pages.
Huang, Y., et al., "Optimization of interferential stimulation of the human brain with electrode arrays," Journal of Neural Engineering, Jun. 12, 2020, 17(3):036023; 12 pages.
Huang, Y., et al., "Optimized tDCS for Targeting Multiple Brain Regions: An Integrated Implementation," Annual International Conference of the IEEE Engineering in Medicine and Biology Society (EMBC), Jul. 2018, pp. 3545-3548.
Jaffino, G., et al., "FPGA-Based System for Real-time Epileptic Seizure Detection using KNN Classifier," 2023 Second International Conference on Electrical, Electronics, Information and Communication Technologies (ICEEICT), Jun. 26, 2023, pp. 1-5.
Jeppesen, J., et al., "Personalized seizure detection using logistic regression machine learning based on wearable ECG-monitoring device," Seizure: European Journal of Epilepsy, Apr. 13, 2023, vol. 107, pp. 155-161.
Jirsa, V. K., et al., "On the nature of seizure dynamics," Brain a Journal of Neurology, [Epub Jun. 11, 2014]; Aug. 2014, 137(8): 2210-2230.
Kaleem, M., et al., "Patient-specific seizure detection in long-term EEG using signal-derived empirical mode decomposition (EMD)-based dictionary approach," Journal of Neural Engineering, Jul. 11, 2018, 15(5):056004; 14 pages.
Kasschau, M., et al., "Transcranial Direct Current Stimulation Is Feasible for Remotely Supervised Home Delivery in Multiple Sclerosis," Neuromodulation: Technology at the Neural Interface, [Epub Apr. 18, 2016]; Dec. 2016, 19(8), pp. 824-831.
Kelly, K.M, et al., "Assessment of a scalp EEG-based automated seizure detection system," Clinical Neurophysiology, [Epub May 14, 2010]; Nov. 2010, 121(11), pp. 1832-1843.
Khan, M. R., et al., "A Low Complexity Patient-Specific threshold based Accelerator for the Grand-Mal Seizure Disorder," 2017 IEEE Biomedical Circuits and Systems Conference (BioCAS), 2017; 4 pages.
Kiening, K., et al., "A new translational target for deep brain stimulation to treat depression," EMBO Molecular Medicine, [Epub Jul. 4, 2013]; Aug. 2013, 5(8), pp. 1151-1153.
Kozák, G., et al., "Sustained efficacy of closed loop electrical stimulation for long-term treatment of absence epilepsy in rats," Scientific Reports, Jul. 24, 2017, 7:6300; 10 pages.
Krook-Magnuson, E., et al., Neuroelectronics and Biooptics: Closed-Loop Technologies in Neurological Disorders, JAMA Neurology, Jul. 2015, 72(7), pp. 823-829.
Kuhlmann, L., et al., "Seizure Detection Using Seizure Probability Estimation: Comparison of Features Used to Detect Seizures," Annals of Biomedical Engineering, [Epub Jul. 10, 2009]; Oct. 2009, 37(10), pp. 2129-2145.
Kutafina, E., et al., "Comparison of mobile and clinical EEG sensors through resting state simultaneous data collection," PeerJ, May 1, 2020, 8: e8969; 22 pages.
Lafon, B., et al., "Low frequency transcranial electrical stimulation does not entrain sleep rhythms measured by human intracranial recordings," Nature Communications, Oct. 31, 2017, 8:1199; 14 pages.
Lee, W., et al., "Image-Guided Transcranial Focused Ultrasound Stimulates Human Primary Somatosensory Cortex," Scientific Reports, Mar. 4, 2015, 5:8743; 10 pages.
Lee, W., et al., "Transcranial focused ultrasound stimulation of human primary visual cortex," Scientific Reports, Sep. 23, 2016, 6:34026; 12 pages.
Legon, W., et al., "Transcranial focused ultrasound modulates the activity of primary somatosensory cortex in humans," Nature Neuroscience, [Epub Jan. 12, 2014]; Feb. 2014, 17(2):322-329; 11 pages (including Online Methods).
Liu, A., et al., "Immediate neurophysiological effects of transcranial electrical stimulation," Nature Communications, Nov. 30, 2018, 9:5092; 23 pages.
Manzouri, F., et al., A Comparison of Energy-Efficient Seizure Detectors for Implantable Neurostimulation Devices, Frontiers in Systems Neuroscience, Mar. 4, 2022, 12:703797; 16 pages.
Manzouri, F., et al., "A Comparison of Machine Learning Classifiers for Energy-Efficient Implementation of Seizure Detection," Frontiers in Systems Neuroscience, Sep. 20, 2018, 12:43; 11 pages.
Mcgill, K. C., et al., "Length-Preserving Wavelet Transform Algorithms for Zero-Padded and Linearly-Extended Signals," Rehabilitation Research and Development Center, VA Medical Center, Palo Alto, CA, Jan. 1992, pp. 1-20.
Merikangas, K. R., et al., "Lifetime Prevalence of Mental Disorders in U.S. Adolescents: Results from the National Comorbidity Survey Replication-Adolescent Supplement (NCS-A)," Journal of the American Academy of Child & Adolescent Psychiatry, [Epub Jul. 31, 2010]; Oct. 2010, 49(10), pp. 980-989.
Michel, C. M., et al., "EEG source imaging," Clinical Neurophysiology, [Epub Jul. 28, 2004], Oct. 2004, 115(10), pp. 2195-2222.
Miller, G., "Is Pharma Running Out of Brainy Ideas?" Science, Jul. 30, 2010, 329(5991), pp. 502-504.
Morrell, M. J., et al., "Responsive Direct Brain Stimulation for Epilepsy," Neurosurgery Clinics of North America, [Epub Nov. 25, 2015]; Jan. 2016, pp. 111-121.
Morrell, M. J., "Responsive cortical stimulation for the treatment of medically intractable partial epilepsy," Neurology, [Epub Sep. 14, 2011]; Sep. 27, 2011, 77(13), pp. 1295-1304.
Murray, C. J. L., "The State of US Health, 1990-2010: Burden of Diseases, Injuries, and Risk Factors," JAMA, Aug. 14, 2013, 310(6), pp. 591-608.

(56) References Cited

OTHER PUBLICATIONS

Nafea, M. S., et al., "Supervised Machine Learning and Deep Learning Techniques for Epileptic Seizure Recognition Using EEG Signals—A Systematic Literature Review," Bioengineering, Dec. 8, 2022, 9(12):781; 35 pages.

Nitsche, M. A., et al., "Excitability changes induced in the human motor cortex by weak transcranial direct current stimulation," The Journal of Physiology, Sep. 15, 2000, 527(3):633-639.

Nowell, M., et al., "Utility of 3D multimodality imaging in the implantation of intracranial electrodes in epilepsy," Epilepsia, [Epub Feb. 5, 2015]; Mar. 2015, 56(3), pp. 403-413.

Onorati, F., et al., "Multicenter clinical assessment of improved wearable multimodal convulsive seizure detectors," Epilepsia, [Epub Oct. 4, 2017]; Nov. 2017, 58(11), pp. 1870-1879.

Opitz, A., et al., "Spatiotemporal structure of intracranial electric fields induced by transcranial electric stimulation in humans and nonhuman primates," Scientific Reports, Aug. 18, 2016, 6:31236; 11 pages.

Ozen, S., et al., "Transcranial Electric Stimulation Entrains Cortical Neuronal Populations in Rats," The Journal of Neuroscience, Aug. 25, 2010, 30(34), pp. 11476-11485.

Paul, Y., "Various epileptic seizure detection techniques using biomedical signals: a review," Brain Informatics, Jul. 10, 2018, 5(2):6; 19 pages.

Pauri, F., et al., "Long-term EEG-video-audio monitoring: computer detection of focal EEG seizure patterns," Electroencephalography and Clinical Neurophysiology, Jan. 1992, 82(1), pp. 1-9.

Perera, N. D., et al., "Spatial Feature Reduction in Long-term EEG for Patient-specific Epileptic Seizure Event Detection," ICSPS 2017: Proceedings of the 9th International Conference on Signal Processing Systems, Nov. 27, 2017, pp. 230-234.

Polanía, R., et al., "Studying and modifying brain function with non-invasive brain stimulation," Nature Neuroscience, [Epub Jan. 8, 2018]; Feb. 2018, vol. 12, pp. 174-187.

Ramdani et al., "Parametric recurrence quantification analysis of autoregressive processes for pattern recognition in multichannel electroencephalographic data," Pattern Recognition, [Epub Aug. 5, 2020]; Jan. 2021, 109:107572; 36 pages.

Rana, P., et al., "Seizure Detection Using the Phase-Slope Index and Multichannel ECoG," : IEEE Transactions on Biomedical Engineering, [Epub Jan. 18, 2012]; Apr. 2012, 59(4), pp. 1125-1134.

Rawald, T., et al., "PyRQA—Conducting recurrence quantification analysis on very long time series efficiently," Computers & Geosciences, [Epub Dec. 3, 2016]; Jul. 2017, vol. 104, pp. 101-108.

Razi, K. F., et al., "Epileptic Seizure Detection With Patient-Specific Feature and Channel Selection for Low-power Applications," IEEE Transactions on Biomedical Circuits and Systems, [Epub Jul. 6, 2022]; Aug. 2022, 16(4), pp. 626-635.

Reznikov, R., et al., "Posttraumatic Stress Disorder: Perspectives for the Use of Deep Brain Stimulation," Neuromodulation: Technology at the Neural Interface, [Epub Jan. 3, 2022]; Jan. 2017, 20(1), pp. 7-14.

Saab, M. E, et al., "A system to detect the onset of epileptic seizures in scalp EEG," Clinical Neurophysiology, [Epub Sep. 18, 2004]; Feb. 2005, 116(2), pp. 427-442.

Sato, T., et al., "Ultrasonic Neuromodulation Causes Widespread Cortical Activation via an Indirect Auditory Mechanism," Neuron, Jun. 6, 2018, 98(5), pp. 1031-1041.e5.

Schad, A., et al., "Application of a multivariate seizure detection and prediction method to non-invasive and intracranial long-term EEG recordings," Clinical Neurophysiology, [Epub Nov. 26, 2007]; Jan. 2008, 119(1), pp. 197-211.

Schalk, G., et al., "BCI2000: A General-Purpose Brain-Computer Interface (BCI) System," IEEE Transactions on Biomedical Engineering, [Epub May 24, 2004]; Jun. 2004, 51(6), pp. 1034-1043.

Schultz, D., et al., "Approximation of diagonal line based measures in recurrence quantification analysis," Physics Letters A, [Epub Jan. 29, 2015]; Jun. 12, 2015, 379(14-15), pp. 997-1011.

Shanir, M., et al., "Time Domain Analysis of EEG for Automatic Seizure Detection," Emerging Trends in Electrical And Electronics Engineering (ETEEE-2015), 2015; 5 pages.

Sparks, R., et al., "Automated multiple trajectory planning algorithm for the placement of stereo-electroencephalography (SEEG) electrodes in epilepsy," International Journal of Computer Assisted Radiology and Surgery treatment, [Epub Jul. 1, 2016]; 2017, vol. 12, pp. 123-136.

Spiegel, S., et al., "Chapter 6: Approximate Recurrence Quantification Analysis (aRQA) in Code of Best Practice," Book Series Published in Springer Proceedings in Physics (SPPHY), May 19, 2016, vol. 180, pp. 113-136.

Taswell, C., et al., "Algorithm 735: Wavelet Transform Algorithms for Finite-Duration Discrete-Time Signals," ACM Transactions on Mathematical Software (TOMS), Sep. 1, 1994, 20(3), pp. 398-412.

Titgemeyer, Y., et al., "Can commercially available wearable EEG devices be used for diagnostic purposes? An explorative pilot study," Epilepsy & Behavior, [Epub Oct. 20, 2019]; Feb. 2020, 103(106507); 8 pages.

Tyler, W. J., et al., "Remote Excitation of Neuronal Circuits Using Low-Intensity, Low-Frequency Ultrasound," PLOS One, Oct. 29, 2008, 3(10):e3511; 11 pages.

Villamar, M. F., et al, "Focal Modulation of the Primary Motor Cortex in Fibromyalgia Using 4x1-Ring High-Definition Transcranial Direct Current Stimulation (HD-tDCS): Immediate and Delayed Analgesic Effects of Cathodal and Anodal Stimulation," The Journal of Pain, [Epub Feb. 14, 2013]; Apr. 2013, 14(4), pp. 371-383.

Vöröslakos, M., et al., "Direct effects of transcranial electric stimulation on brain circuits in rats and humans," Nature Communications, Feb. 2, 2018, 9(1):483; 17 pages.

Wang, D. D., et al., "Pallidal Deep-Brain Stimulation Disrupts Pallidal Beta Oscillations and Coherence with Primary Motor Cortex in Parkinson's Disease," The Journal of Neuroscience, May 9, 2018, 38(19), pp. 4556-4568.

Webb, T. D., et al., "Remus: System for remote deep brain interventions," iScience, Nov. 18, 2022, 25(11):105251; 14 pages.

Webb, T. D., et al., "Sustained modulation of primate deep brain circuits with focused ultrasonic waves," Brain Stimulation, [Epub Apr. 18, 2023]; May-Jun. 2023, 16(3), pp. 798-805.

Wilson, S. B., et al., "Seizure detection: evaluation of the Reveal algorithm," Clinical Neurophysiology, [Epub Jun. 26, 2004]; Oct. 2004, 115(10), pp. 2280-2291.

Wong, S., et al., "EEG datasets for seizure detection and prediction—A review," Epilepsia Open, [Epub Feb. 5, 2023]; Jun. 2023, 8(2), pp. 252-267.

Yoo, S-S., et al., "Focused ultrasound modulates region-specific brain activity," NeuroImage, [Epub Feb. 24, 2011]; Jun. 1, 2011, 56(3), pp. 1267-1275.

Zandi, A. S., et al., "Detection of Epileptic Seizures in Scalp Electroencephalogram: An Automated Real-Time Wavelet-Based Approach," Journal of Clinical Neurophysiology, Feb. 2012, 29(1), pp. 1-16.

* cited by examiner

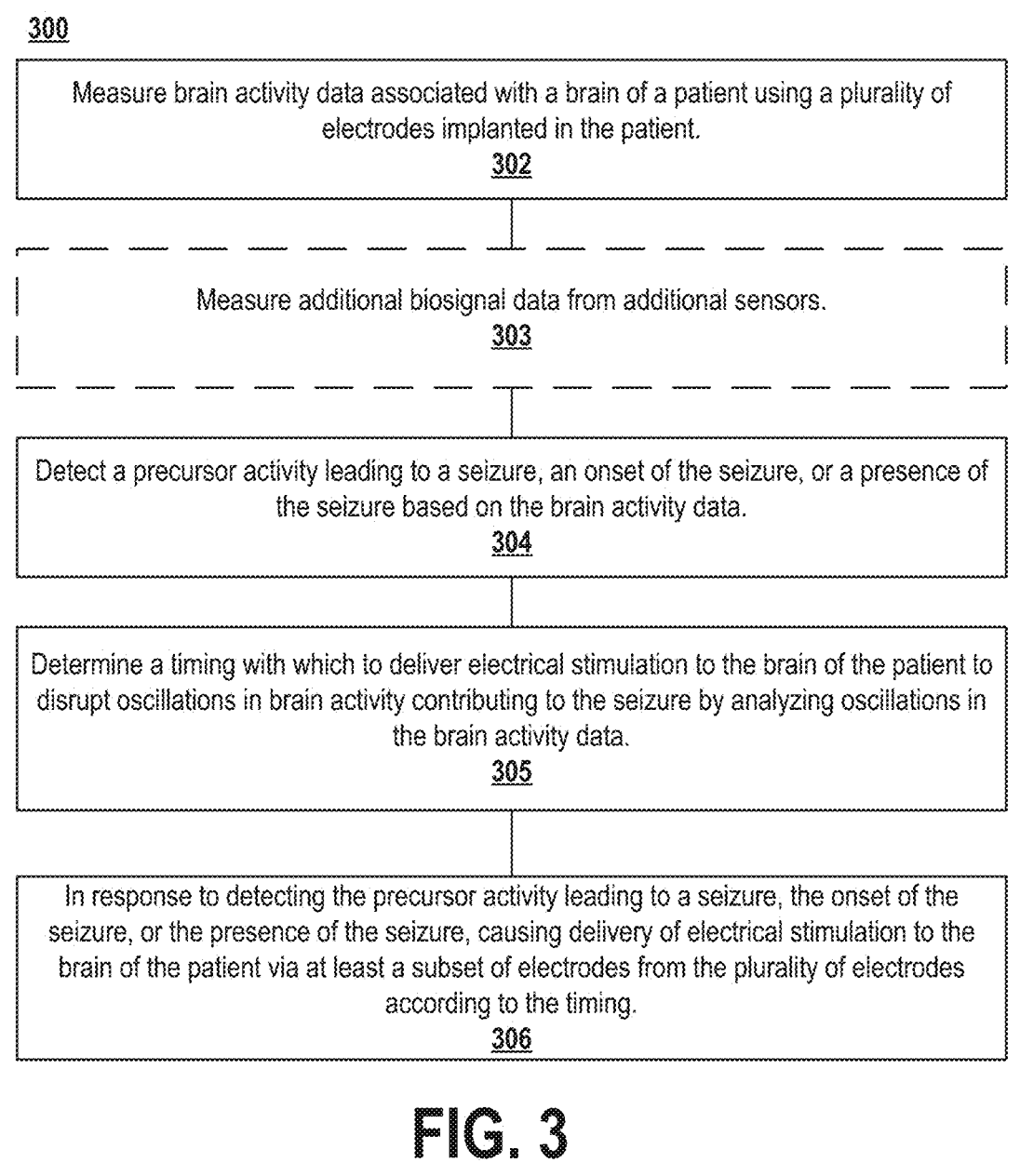

300

```
┌─────────────────────────────────────────────────────────────────────┐
│     Measure brain activity data associated with a brain of a patient   │
│               using a plurality of electrodes implanted in the patient.│
│                                  302                                   │
└─────────────────────────────────────────────────────────────────────┘
```

```
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│          Measure additional biosignal data from additional sensors.    │
│                                  303                                   │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
```

```
┌─────────────────────────────────────────────────────────────────────┐
│   Detect a precursor activity leading to a seizure, an onset of the    │
│   seizure, or a presence of the seizure based on the brain activity    │
│                               data.                                    │
│                                  304                                   │
└─────────────────────────────────────────────────────────────────────┘
```

```
┌─────────────────────────────────────────────────────────────────────┐
│  Determine a timing with which to deliver electrical stimulation to the│
│  brain of the patient to disrupt oscillations in brain activity        │
│  contributing to the seizure by analyzing oscillations in the brain    │
│  activity data.                                                        │
│                                  305                                   │
└─────────────────────────────────────────────────────────────────────┘
```

```
┌─────────────────────────────────────────────────────────────────────┐
│  In response to detecting the precursor activity leading to a seizure, │
│  the onset of the seizure, or the presence of the seizure, causing     │
│  delivery of electrical stimulation to the brain of the patient via at │
│  least a subset of electrodes from the plurality of electrodes         │
│  according to the timing.                                              │
│                                  306                                   │
└─────────────────────────────────────────────────────────────────────┘
```

FIG. 3

Based on: Baumgartner C, Koren JP, Rothmayer M. Automatic Computer-Based Detection of Epileptic Seizures. Front Neurol. 2018 Aug 9;9:639. doi: 10.3389/fneur.2018.00639.

| References | Ref. | EEG sample (hours) | Patients | Seizures | Sensitivity (%) | Specificity FAR (per hour) | Detection delay (s) |
|---|---|---|---|---|---|---|---|
| Gotman | 1 | 4362 | 44 | 179 | 73,20 | 0,84 | n.a. |
| Pauri et al. | 2 | 461 | 12 | 253 | 81,40 | 5,38 | n.a. |
| Gabor et al. | 3 | 528 | 33 | 62 | 90,30 | 0,71 | n.a. |
| Gabor | 4 | 4554 | 65 | 181 | 92,80 | 1,35 | n.a. |
| Wilson et al. | 5 | 1049 | 426 | 672 | 76,00 | 0,11 | n.a. |
| Saab and Gotman | 6 | 360 | 16 | 69 | 76,00 | 0,34 | 10,0 |
| Kuhlmann et al. | 7 | 525 | 21 | 88 | 81,00 | 0,60 | 16,9 |
| Meier et al. | 8 | 1403 | 57 | 91 | >96,0 | <0,5 | 7,0 |
| Schad et al. | 8 | 423 | 6 | 26 | 58,00 | 0,15 | n.a. |
| Kelly et al. | 9 | 1200 | 55 | 146 | 78,50 | 0,08 | n.a. |
| Zandi et al. | 10 | 236 | 26 | 79 | 91,00 | 0,33 | 7,0 |
| Hopfengärtner et al. | 11 | 3248 | 19 | 148 | 90,90 | 0,29 | 18,0 |
| Hopfengärtner et al. | 12 | 25278 | 159 | 794 | 87,30 | 0,22 | n.a. |
| Hartmann et al. | 13 | 4300 | 48 | 186 | 83,00 | 0,30 | n.a. |
| Fürbass et al. | 14 | 22000 | 275 | 623 | 73,00 | 0,30 | n.a. |
| Fürbass et al. | 15 | 15684 | 205 | 536 | 81,00 | 0,29 | n.a. |
| Current algorythm | 16 | 246,50 | 129 | 1171 | 94,78 | 0,24 | 0,5 |

1. Gotman J. Automatic seizure detection: improvements and evaluation. Electroencephalogr Clin Neurophysiol. (1990) 76:317-24.

2. Pauri F, Pierelli F, Chatrian GE, Erdly WW. Long-term EEG-video-audio monitoring: computer detection of focal EEG seizure patterns. Electroencephalogr Clin Neurophysiol. (1992) 82:1-9.

3. Gabor AJ, Leach RR, Dowla FU. Automated seizure detection using a self-organizing neural network. Electroencephalogr Clin Neurophysiol. (1996) 99:257-66.

4. Gabor AJ. Seizure detection using a self-organizing neural network: validation and comparison with other detection strategies. Electroencephalogr Clin Neurophysiol. (1998) 107:27-32.

5. Wilson SB, Scheuer ML, Emerson RG, Gabor AJ. Seizure detection: evaluation of the Reveal algorithm. Clin Neurophysiol. (2004) 115:2280-91.

6. Saab ME, Gotman J. A system to detect the onset of epileptic seizures in scalp EEG. Clin Neurophysiol. (2005) 116:427-42.

7. Kuhlmann L, Burkitt AN, Cook MJ, Fuller K, Grayden DB, Seiderer L, et al. Seizure detection using seizure probability estimation: comparison of features used to detect seizures. Ann Biomed Eng. (2009) 37:2129-45.

8. Schad A, Schindler K, Schelter B, Maiwald T, Brandt A, Timmer J, et al. Application of a multivariate seizure detection and prediction method to non-invasive and intracranial long-term EEG recordings. Clin Neurophysiol. (2008) 118:197-211.

9. Kelly KM, Shiau DS, Kern RT, Chien JH, Yang MC, Yandora KA, et al. Assessment of a scalp EEG-based automated seizure detection system. Clin Neurophysiol. (2010) 121:1832-43.

10. Zandi AS, Dumont GA, Javidan M, Tafreshi R. Detection of epileptic seizures in scalp electroencephalogram: an automated real-time wavelet-based approach. J Clin Neurophysiol. (2012) 29:1-16. doi: 10.1097/WNP.0b013e31824fbc 11. Hopfengärtner R, Kerling F, Bauer V, Stefan H. An efficient, robust and fast method for the offline detection of epileptic seizures in long-term scalp EEG recordings. Clin Neurophysiol. (2007) 118:2332-43.

12. Hopfengärtner R, Kasper BS, Graf W, Gollwitzer S, Kreiselmeyer G, Stefan H, et al. Automatic seizure detection in long-term scalp EEG using an adaptive thresholding technique: a validation study for clinical routine. Clin Neurophysiol. (2014) 125:1346-52.

13. Hartmann MM, Furbass F, Perko H, Skupch A, Lackmayer K, Baumgartner C, et al. EpiScan: online seizure detection for epilepsy monitoring units. Conf Proc IEEE Eng Med Biol Soc. (2011) 2011:6096-9.

14. Furbass F, Hartmann M, Perko H, Skupch A, Dollfuss P, Gritsch G, et al. Combining time series and frequency domain analysis for a automatic seizure detection. Conf Proc IEEE Eng Med Biol Soc. (2012) 2012:1020-3. doi: 10.1109/embc.2012.6346107

15. Furbass F, Ossenblok P, Hartmann M, Perko H, Skupch AM, Lindinger G, et al. Prospective multi-center study of an automatic online seizure detection system for epilepsy monitoring units. Clin Neurophysiol. (2015) 126:1124-31.

16. Karagozo M, Foldi T, Kozak G, Nagy AJ, Cserkontos T, Varsalakos RA, Berenyi A. Closed-loop implementation of intersectional short-pulse (ISP) stimulation to stop temporal lobe seizures. Annual Meeting of the Society for Neuroscience, (2019), 371.10.

FIG. 9

Steps to calculate RQA:

1    position of triplets to compare with each other:

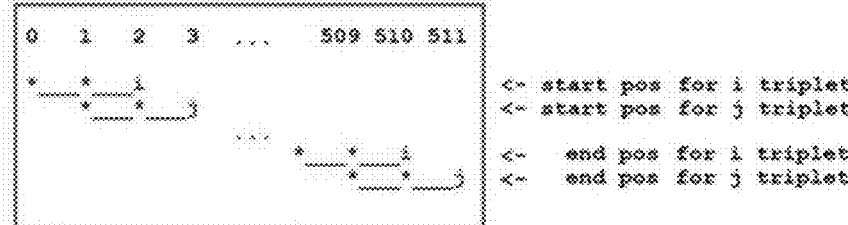

<- start pos for i triplet
<- start pos for j triplet

<-   end pos for i triplet
<-   end pos for j triplet

2    results of comparison
between triplet i and j:

```
0 0 1 0 1 1 0 0 0 1     i= 2   j= 3...511
  0 1 0 0 1 0 0 1 1     i= 3   j= 4...511
    0 1 0 1 0 1 1 0 1   i= 4   j= 5...511
    1 0 1 1 0 1 1 0
      0 0 1 0 1 0 1
        0 1 1 0 1 0
        1 1 0 1 1       ...
          1 0 1 0
          1 0 0
            0 1         i=509  j=510...511
            1           i=510  j=   511
```

3    the same table aligned left,
vertical trains of 1s counted:

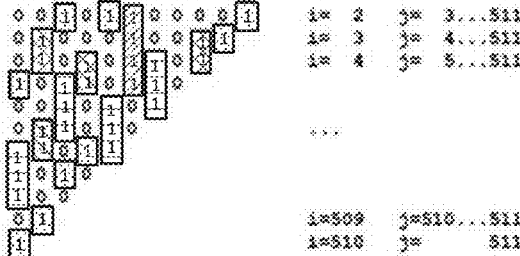

i= 2   j= 3...511
i= 3   j= 4...511
i= 4   j= 5...511

...

i=509  j=510...511
i=510  j=   511

4    histogram
distribution of train lengths:

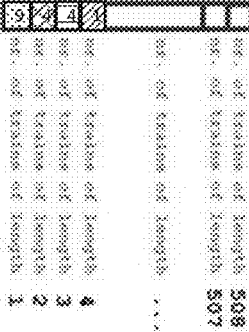

FIG. 12

Steps to calculate COHER feature value:

The COHER value for Channel A is the
average of coherences between channel A and every other channel
for all frequency components.

Steps to calculate coherence of one Channel Pair:

1   Divide the 512-long window into 7 overlapping segments of length 128.

2   Apply a Hanning window to all segments
    and calculate complex freq. spectrum.

3   For every complex freq. component,
    calculate
    1) magnitude square
    2) cross product with other channel's complex conjugate

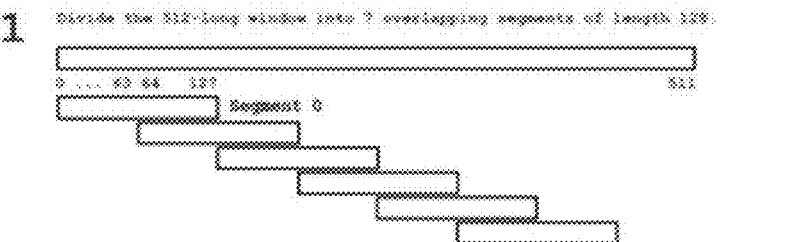

4   Coherence
    for channel pair AB     =
    for 1 freq component

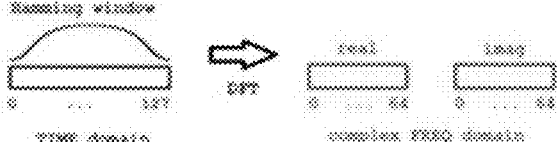

FIG. 14

Scaling and wavelet vector

SYSTEMS AND METHODS FOR SEIZURE DETECTION AND CLOSED-LOOP NEUROSTIMULATION

CROSS-REFERENCE TO RELATED APPLICATIONS

This application claims priority to and the benefit of U.S. Provisional Application 63/610,955, titled "SYSTEMS AND METHODS FOR SEIZURE DETECTION AND CLOSED-LOOP NEUROSTIMULATION" and filed Dec. 15, 2023, the disclosure of which is incorporated by reference herein in its entirety.

TECHNICAL FIELD

Embodiments described herein relate to systems, devices, and methods for monitoring brain activity and delivering electrical brain stimulation to a patient. More specifically, one or more embodiments described herein relate to monitoring brain activity to detect an onset of a seizure and to deliver electrical stimulation to inhibit the seizure.

BACKGROUND

High intensity neurostimulation can alter brain activity in a nearly instantaneous manner and can be used to terminate epileptic seizures. It is preferable to terminate initiation of seizures as soon as possible before the seizures generalize and before behavioral symptoms develop. In order to terminate a seizure, a system should be capable of fast/early recognition of seizure patterns (short detection delay), highly reliable seizure recognition (high sensitivity), and a low false alarm rate (high specificity). Achieving a low false alarm rate is important to avoid unnecessary stimulation of the brain, as high intensity stimulation may deplete battery and may cause inconvenience to patients. Known real-time seizure detector algorithms lack these capabilities, and as such, novel approaches and improved detection methodologies are needed to improve detector performance and facilitate closed-loop neurostimulation in epilepsy and other brain disorders.

SUMMARY

In some embodiments, a system comprises a plurality of electrodes configured for implantation in a patient and configured to measure a brain activity of the patient; a memory; and one or more processors operatively coupled to the memory and the plurality of electrodes. The one or more processors configured to receive brain activity data from the plurality of electrodes; detect an onset of a seizure based on the brain activity data; determine, based on a pattern in the brain activity data, a timing with which to deliver current pulses to a brain of the patient to disrupt at least one oscillation in brain activity contributing to the seizure; and activate a subset of electrodes from the plurality of electrodes to deliver the current pulses to a target region of the brain of the patient according to the timing. In some embodiments, the brain activity data includes electroencephalography (EEG) data. In some embodiments, the plurality of electrodes includes between 1 electrode contacts and 256 electrode contacts. In some embodiments, at least a subset of electrodes from the plurality of electrodes is implanted in one of a subgaleal space of the patient, a subdural space of the patient, an epidural space of the patient, or the brain of the patient. In some embodiments, the plurality of electrodes is implanted in a subgaleal space of the patient. In some embodiments, the plurality of electrodes is configured to deliver Intersectional Short-Pulse (ISP) stimulation. In some embodiments, each of the current pulses has an amplitude of about 0.1 mA to about 80 mA.

In some embodiments, the one or more processors is configured to determine the timing based on at least one of a phase or a frequency of the brain activity data, and to activate the subset of electrodes to deliver the current pulses one of immediately or after a predetermined delay, and with a predefined frequency. In some embodiments, the one or more processors is further configured to recognize the pattern of brain activity, the one or more processors is configured to activate the subset of electrodes to deliver the current pulses one of immediately or after a predetermined delay, the one or more current pulses configured to align with an inherent rhythmicity of the brain activity data. In some embodiments, the one or more processors includes at least one of a field-programmable gate array (FPGA) chip or a microcontroller.

In some embodiments, the system further comprises a battery configured to supply power to each of the processor, the memory, and the plurality of electrodes. In some embodiments, the battery is implanted in a chest of the patient. In other embodiments, the battery is disposed on a head of the patient. In some embodiments, the system further comprises one or more sensors configured to measure biosignal data associated with the patient, the one or more processors configured to detect a precursor activity leading to a seizure, the onset of the seizure, or a presence of the seizure further based on the biosignal data. In some embodiments, the one or more sensors are configured to measure at least one of electromyography (EMG) data, electrocardiogram (ECG) data, or heart rate. In some embodiments, the one or more processors is further configured to quantify the pattern in the brain activity data by calculating a measure of rhythmicity at predetermined frequency components of the brain activity data. In some embodiments, the measure of rhythmicity may include phase values of the signal, detection of peaks in the signal, detection of the signal crossing a threshold, etc.

In some embodiments, the system further comprises a communication interface configured to transfer information between the one or more processors and an external device, the external device configured to train a model for detecting a precursor activity leading to a seizure, the onset of the seizure, or a presence of the seizure, the model configured to be executed by the one or more processors. In some embodiments, the model is trained using datasets including ictal EEG data and non-ictal EEG data from at least one of the patient or another patient.

In some aspects, an implantable neurostimulator device comprises a memory; and a processor operatively coupled to the memory, the processor configured to be electrically coupled to a plurality of electrodes implanted in a patient. The processor configured to: receive brain activity data from the plurality of electrodes; detect a precursor activity leading to a seizure, the onset of the seizure, or a presence of the seizure based on the brain activity data; determine a timing with which to deliver current pulses to the brain of the patient to interfere with at least one oscillation in brain activity contributing to the seizure, by calculating a measure of rhythmicity of the brain activity data; and activate a subset of electrodes from the plurality of electrodes to deliver the current pulses to the region of the brain of the patient based on the timing. In some embodiments, the brain activity data includes electroencephalography (EEG) data. In some embodiments, the plurality of electrodes includes between 1 electrode contacts and 256 electrode contacts. In some embodiments, at least a subset of electrodes from the plurality of electrodes is implanted in one of a subgaleal space of the patient, a subdural space of the patient, an epidural space of the patient, or the brain of the patient. In some embodiments, the plurality of electrodes is implanted in a subgaleal space of the patient. In some embodiments, the plurality of electrodes is configured to deliver Intersectional Short-Pulse (ISP) stimulation. In some embodiments, each of the current pulses has an amplitude of about 0.1 mA to about 80 mA.

In some embodiments, the one or more processors is configured to determine the timing based on one of the measure of rhythmicity in the brain activity data or a feature of the rhythmicity in the brain activity data, and to activate the subset of electrodes to deliver the current pulses one of immediately or after a predetermined delay, and with a predefined frequency. In some embodiments, the one or more processors is further configured to recognize a pattern of brain activity, the one or more processors is configured to activate the subset of electrodes to deliver the current pulses one of immediately or after a predetermined delay, the one or more current pulses configured to align with an inherent rhythmicity of the brain activity data. In some embodiments, the one or more processors includes at least one of a field-programmable gate array (FPGA) chip or a microcontroller.

In some embodiments, the implantable neurostimulator device further comprises a battery configured to supply power to each of the processor, the memory, and the plurality of electrodes. In some embodiments, the battery is configured to be disposed on the head of the patient. In other embodiments, the battery is configured to be implanted in a chest (e.g., under the skin or under one or more muscles of the chest) of the patient. In some embodiments, the battery is rechargeable. In some embodiments, the implantable neurostimulator device further comprises one or more sensors configured to measure biosignal data associated with the patient, the one or more processors configured to detect the precursor activity leading to the seizure, the onset of the seizure, or the presence of the seizure further based on the biosignal data. In some embodiments, the one or more sensors are configured to measure at least one of electromyography (EMG) data, electrocardiogram (ECG) data, or heart rate.

In some aspects, a method comprises measuring brain activity data associated with a brain of a patient using a plurality of electrodes implanted in the patient; detecting an onset of a seizure based on the brain activity data; determining a timing with which to deliver electrical stimulation to the brain of the patient to disrupt oscillations in brain activity contributing to the seizure, by analyzing oscillations in the brain activity data; and in response to detecting a precursor activity leading to a seizure, an onset of the seizure, or the presence of the seizure, causing delivery of electrical stimulation to the brain of the patient via at least a subset of electrodes from the plurality of electrodes and according to the timing. In some embodiments, the brain activity data includes electroencephalography (EEG) data. EEG activity may include brain activity data recorded by scalp EEG, subgaleal or subdermal EEG, electrocorticogram (ECoG) recorded by subdural electrodes, optical or magnetic acquisition, and/or penetrating electrodes, such as DBS or stereoelectroencephalography (stereoEEG or sEEG) leads. In some embodiments, the EEG data includes data collected from 1-256 EEG channels. In some embodiments, the delivery of the electrical stimulation is performed using intersectional short-pulse (ISP) stimulation. In some embodiments, the ISP stimulation is delivered with an amplitude of about 0.1 mA to about 80 mA. In some embodiments, the method further comprises applying a filter to each of the EEG channels; and generating a virtual channel by calculating a weighted average of the EEG channels.

In some embodiments, the method further comprises applying a sliding window to the EEG channels and the virtual channel to produce windowed EEG channels and a windowed virtual channel; and calculating features for each of the windowed EEG channels and the windowed virtual channel based on a predefined time interval. In some embodiments, the features include at least one of time domain features, frequency domain features, spatial features, or temporal dynamic features. In some embodiments, the features include at least one of a root mean square, a line length, a variance, a kurtosis, a Hjorth mobility, a Hjorth complexity, a wavelet transform, a mutual information, a mean coherence, a standard deviation of mean phase delay, a recurrence rate, a determinism, an entropy, or an averaged diagonal line length.

In some embodiments, the method further comprises inputting the features to a regressive decision tree trained using EEG data from the patient or EEG data from at least one other patient; averaging outputs of the regressive decision trees to produce an averaged output; and comparing the averaged output to a dynamic threshold that is updated based on previous outputs of a classification model. In some embodiments, the determining the timing with which to deliver the electrical stimulation includes detecting a phase of the oscillations in the brain activity or in the virtual channel, the timing determined such that the electrical stimulation weakens, disrupts, or terminates the brain oscillation. In some embodiments, a filter is applied to the data sources used for the phase detection (e.g., EEG channel, virtual channel, other biosignal channel) to constrain the detection only to oscillations in a specific frequency band. In some embodiments, the electrical stimulation has a predefined refractory period and a predefined maximum stimulation number to prevent over-stimulation.

In some aspects, a method includes calculating one or more features based on brain activity recorded from each of a plurality of electrodes implanted in a patient; inputting at least one of (1) the one or more features, or (2) at least a portion of the recorded brain activity into a model trained using brain activity data of at least one of the patient or at least one other patient; determining a range of effective prediction probability threshold values and selecting a threshold value from the range of effective prediction probably threshold values; comparing an output of the model to the threshold value; in response to determining the output crosses (e.g., exceeds) the threshold value, determining a timing and a subset of electrodes with which to deliver electrical pulses; and causing delivery of the electrical pulses to the brain of the patient via the subset of electrodes and according to the timing.

BRIEF DESCRIPTION OF DRAWINGS

FIG. 3 is a flow chart diagram of a method for detecting seizure activity and delivering electrical brain stimulation to inhibit the seizure activity, according to an embodiment.

FIG. 9 is a table comparing previously existing seizure detection algorithms with the proposed seizure detection algorithm.

FIG. 12 shows an example method of calculating Recurrence Quantification Analysis.

FIG. 14 shows an example method of calculating a Coherence Feature Value.

DETAILED DESCRIPTION

Figure 1A:
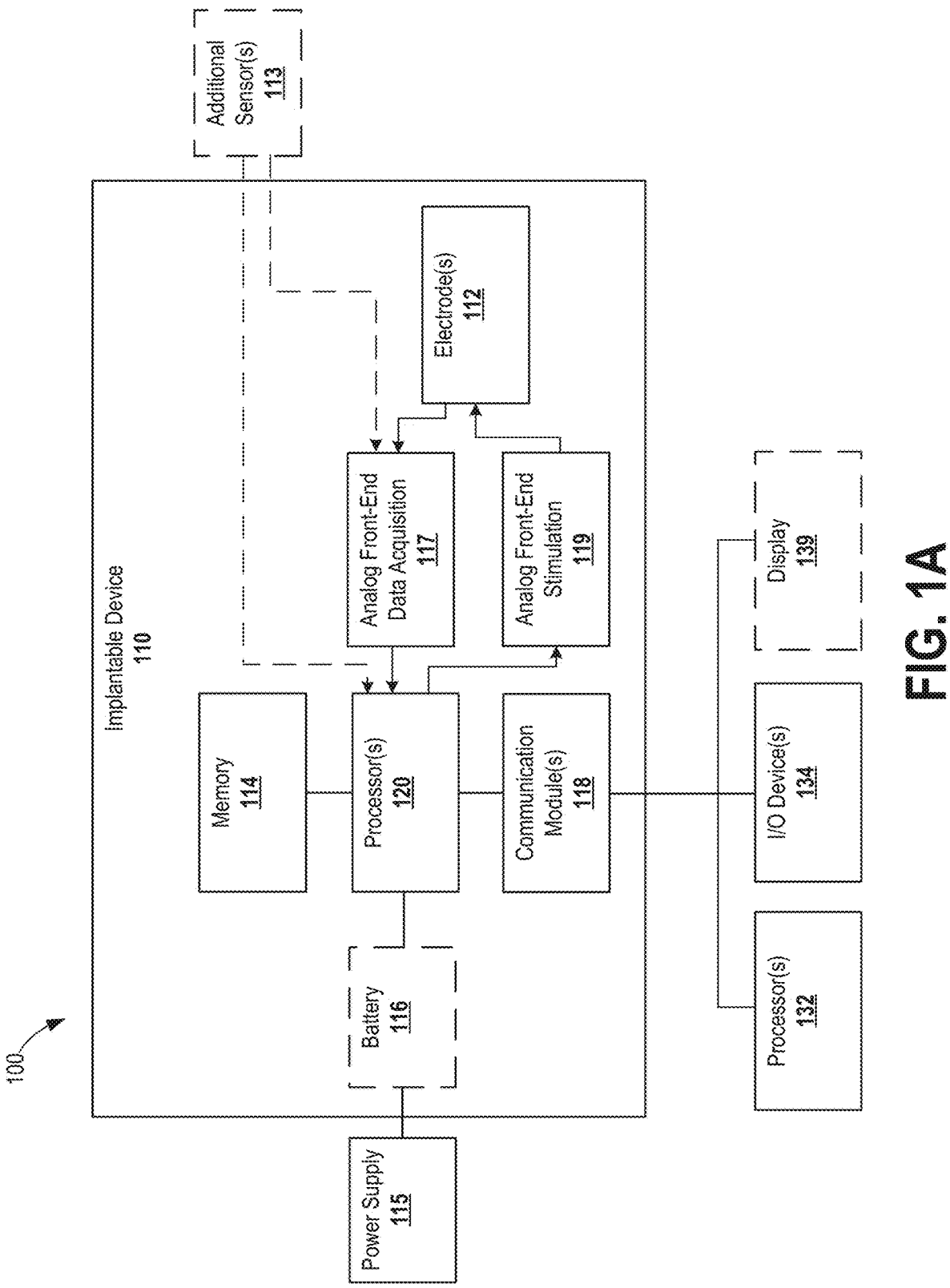
FIG. 1A is a schematic block diagram of a system for monitoring brain activity and delivery electrical brain stimulation, according to an embodiment.

Known seizure detection algorithms running on embedded systems can exhibit undesirable detection delays and high false alarm rates, with inadequate speed, sensitivity, and specificity, such that use of the known systems can lead to unnecessary brain stimulation and inconvenience to patients. Systems and methods set forth herein, by contrast, and according to one or more embodiments, address the foregoing issues by delivering responsive electrical brain stimulation (e.g., in response to detecting seizure onset), in a closed-loop manner, and can offer real-time or near real-time monitoring of induced neurophysiological effects, as discussed further below.

1. Closed-Loop Neurostimulation in Epilepsy
1.1 Context

Neuropsychiatric disorders are highly prevalent and disabling illnesses, affecting ~20% of Americans, and these disorders cause 18.7% of total years lost to disability and mortality, according to some estimates. Studies show that current therapies fail to control between 15-30% of patients with epilepsy, anxiety, post-traumatic stress, and major depression. Advances in medication therapy are unlikely to dramatically improve these statistics, reflected in decreased pharmaceutical research budgets for neuropsychiatric disorders. Moreover, medications cannot adapt to fine-scale temporal dynamics of the brain disease state and can cause adverse effects during asymptomatic and symptomatic periods.

1.2 Device-Based Neuromodulation

The goal of therapeutic brain stimulation by a device is spatiotemporal specificity, i.e., the ability to modulate brain activity at specific locations and times. Non-invasive brain stimulation methods offer an unprecedented opportunity to probe and modify the brain in health and disease. These methods have led to novel insights of brain function and are widely used in clinical practice. High intensity neurostimulation can be used to terminate epileptic seizures, for example, if delivered in a closed-loop fashion with adequate intensity.

Most human experimental studies and clinical trials of non-invasive neuromodulation use Transcranial Magnetic Stimulation (TMS) and Transcranial Electrical Stimulation (TES) as either direct current (TDCS) or alternating current (TACS) stimulation. Recently, several groups have explored Transcranial Focused Ultrasound Stimulation (TFUS) to affect cortical targets.

Transcranial Electrical Stimulation (TES) embodies several features including non-invasiveness, convenience, and low cost, that make it an ideal candidate for a wearable or implantable, closed-loop neurostimulation therapy. While known non-invasive TES typically stimulates large diffuse brain areas (mostly superficial neocortex), there are methods for improving spatial resolution. Feasibility studies demonstrating that TES can be applied in a closed-loop manner to instantaneously modulate single unit firing and terminate epileptic seizures in rodents are provided in Ozen, S., Sirota, A., Belluscio, M. A., Anastassiou, C. A., Stark, E., Koch, C., Buzsaki, G., & Buzsaki, G. (2010). Transcranial electric stimulation entrains cortical neuronal populations in rats. J Neurosci, 30(34), 11476-11485, (hereinafter "Ozen et al."); and Berenyi, A., Belluscio, M., Mao, D., & Buzsaki, G. (2012). Closed-Loop Control of Epilepsy by Transcranial Electrical Stimulation. Science, 337(6095), 735-737, (hereinafter, "Berenyi et al."), the disclosure of each of which is hereby incorporated by reference in its entirety.

Epilepsy is a disorder of brain dynamics where neural networks, acting like multistable oscillators, abruptly switch from normal to hyperactive, seizure states. In a healthy brain, these networks balance sensory, cognitive, and motor functions, but epilepsy triggers a rapid, disruptive transition to excessive neuronal activity-a network-level phenomenon leading to seizures. In studying epilepsy, mathematical models describe how neurons shift between resting, active, and seizure states-changes resembling phase transitions in physics. Neuromodulation targets these transitions, either by preventing the brain from nearing seizure thresholds or by reversing a seizure after an onset of the seizure. Prevention involves stabilizing the brain's normal state, creating an 'energy barrier' against the transition to a seizure. Conversely, stopping a seizure involves precise, energy-intensive stimulation to navigate the brain back to normalcy, following a careful trajectory to avoid further issues. Thus, while preventing seizures is about keeping the brain within safe operational boundaries, termination demands complex, strategic intervention to revert from an established pathological state to normal function. The latter is particularly challenging, as it involves directing the brain along a fine, specific path to ensure a safe return to equilibrium, and it is important that neuromodulation is targeted, precise and driven by the brain activity itself.

1.3 Automated Seizure Onset Detection for Closed-Loop Stimulation

Automated seizure onset detection for closed-loop stimulation merges neurology, computational neuroscience, control theory, and machine learning to monitor and control brain activity. The brain is viewed as a complex system that can transition between normal and seizure states. The objective is to continuously monitor brain patterns, detect the early signs of a seizure, and promptly deliver neuromodulation to revert the brain to its normal state. Using control theory, this process is managed by a feedback loop that reacts to deviations from normal brain function, employing algorithms to detect seizures and initiate countermeasures, like electrical stimulation, to maintain neural stability.

1.3.1 Example Seizure Detection Pipeline

Advanced signal processing techniques form the scientific basis for effective seizure detection. Most techniques are developed and validated using publicly available curated seizure EEG datasets. Time-series data of electroencephalogram (EEG) readings can be continuously monitored to identify unique patterns indicative of seizure onset. Various transforms can be employed to convert raw EEG signals into a set of characteristics that can be classified into 'normal' or 'seizure' states.

The first step in a seizure detection algorithm may be feature extraction, where salient characteristics of the raw data are identified and used for further analysis. The most common methods to extract seizure-predictive features from EEG Data are:

1. Time-Domain Analysis: In this approach, the raw EEG data may be directly analyzed to identify patterns or characteristics indicative of seizure onset. Amplitude thresholds may be used, or more complex features like zero-crossing rates and entropy may be extracted.
2. Frequency-Domain Analysis: Fast Fourier Transform (FFT) or other spectral analysis techniques may be employed to convert EEG signals into the frequency domain. The energy distribution across different frequency bands can be used to identify seizure activity.
3. Wavelet Transform: Wavelet transforms may be particularly useful for non-stationary signals like EEG. Wavelet transforms allow the decomposition of EEG data into both time and frequency components, facilitating the identification of transient seizure-related features. Short Time FFT or Wigner-Ville distribution may be alternatives to wavelet analysis.
4. Nonlinear Dynamic Methods: Measures like Lyapunov exponents, correlation dimension, or Hurst exponent are used to identify chaotic behaviors associated with seizures.

Some non-neuronal biological signals such as heart rate variability (HRV) or changes in respiratory rate may also be predictive to seizures. Wrist-worn or body-fixed accelerometry sensors can detect the convulsive movements often associated with certain types of seizures. Multimodal approaches can combine multiple features and multiple types of biodata (e.g., EEG, electrocorticography (ECoG), HRV, accelerometry) for a more reliable seizure detection. Data fusion techniques, including feature-level fusion and decision-level fusion, can be employed. Methods like Support Vector Machines, Decision Trees, and Neural Networks can be employed to classify extracted features into 'seizure' or 'non-seizure' categories.

In summary, seizure detection may focus on extracting meaningful features from raw data and then using various classification techniques to identify seizure events. While EEG can be used as a data source, other forms of biodata can be incorporated for more reliable and comprehensive seizure detection.

1.3.2 Offline Vs. Real-Time Seizure Detection

Offline seizure detection is used for research and diagnosis, focusing on high accuracy using complex algorithms, without time constraints, allowing for thorough tuning and validation. Real-time online seizure detection, however, aims for immediate intervention, such as in closed-loop neuromodulation systems, requiring low-latency, efficient algorithms that balance accuracy and computational speed to avoid short battery life in wearable or implantable devices. Real-time detection faces the challenge of making decisions based on incomplete data, without the benefit of seeing the entire time course of the seizure event, increasing the risk of false positives or negatives. Real-time systems may have to detect seizures with limited contextual information, differentiating true seizures from normal brain activity and from movement artifacts quickly to avoid inappropriate interventions. To overcome these challenges, adaptive systems that learn from individual brain activity patterns are key, aiming to increase accuracy and reliability while reducing errors and minimizing power consumption.

1.3.3 Concepts of Hardware and Firmware Embodiments

Real-time online seizure detectors could leverage specialized hardware, such as Application-Specific Integrated Circuits (ASICs), to perform low-latency, high-efficiency computations essential for immediate intervention. ASICs could be designed to run specific algorithms that are optimized for feature extraction and classification tasks, balancing between computational speed and power consumption-a crucial factor for implantable or wearable devices, however they usually have limited adaptivity and due to their hardcoded nature they lack algorithmic flexibility.

On the firmware side, concepts like real-time operating systems (RTOS) come into play, offering the scheduling precision and task prioritization required for such critical applications. Field-programmable gate arrays (FPGA) may offer additional computational efficacy in stages which employ repetitive steps, which can be executed simultaneously in time in parallelized fashion. The firmware could be programmed to adaptively update its detection algorithms based on a continuous learning model, thereby increasing the detector's accuracy over time. This adaptability could be crucial for accommodating the inter-patient and intra-patient variability often observed in seizure characteristics.

Both hardware and firmware components would ideally be built with redundancy and fail-safe mechanisms to ensure reliability, given the life-critical nature of seizure detection and intervention. This would entail concepts from fault-tolerant computing to ensure system robustness under various conditions, including hardware failure, signal noise, or unexpected power loss.

1.3.4 Energy Efficiency Considerations

In real-time online seizure detection, ASICs, RTOS, and FPGAs present different compromises between energy efficiency and flexibility. ASICs are energy-optimized for specific tasks, ideal for power-sensitive devices but lack flexibility for updates. RTOS-based solutions provide easy updates and flexible operation at a higher energy cost, as they run on general-purpose processors and are not primarily designed for energy savings. FPGAs strike a balance, offering ability to be reprogrammed with better energy efficiency than RTOS solutions.

Algorithm design also affects energy use; simpler algorithms consume less power than complex machine learning models. Thus, hardware and algorithm optimization are key for a balance in efficiency and accuracy. Machine learning algorithms have varied energy profiles. Support Vector Machines (SVMs) and Decision Trees are less demanding, suitable for low-power devices. In contrast, Deep Neural Networks (DNNs), particularly multi-layered ones, require more power for training and inference, potentially unsuitable for devices with stringent energy constraints. Ensemble methods may balance accuracy and energy but increase complexity and power needs. Hence, the choice of classification method is critical for the energy management of seizure detection systems.

1.3.5 Patient-Specific Vs Universal (Cross-Patient) Seizure Detectors

Patient-specific methods in real-time seizure detection tailor algorithms to an individual's unique seizure traits using custom thresholds and features, and adaptive models that learn from the patient's changing physiology. These yield high accuracy but need substantial individual data and frequent retraining, which can reduce energy efficiency and generalizability.

In contrast, general approaches use population-wide data to create broadly applicable models, which are less computationally intensive and more energy-efficient, but they may have higher false positives and miss unique individual seizure patterns.

Choosing between these methods depends on available computational power, the necessity for immediacy in seizure response, and tolerance for error rates. Also, devices may have an initial configuration for non-patient specific seizure detection with acceptable performance ('cold start'), which can be further refined based on the patient specific data as they become available.

1.4 Merits and Challenges of Non- or Minimal-Invasive Stimulation Methods

The debate between non-invasive transcranial electrical stimulation and invasive Deep Brain Stimulation (DBS) for seizure control is a balance of safety and effectiveness.

Transcranial stimulation is safer, with less surgical risk and complications, but its efficacy is lessened by the skull filtering out EEG signals and electrical stimuli, leading to potential noise, missed detections, and the risk of unintended effects. Moreover, targeting deep brain areas is difficult through non-invasive means due to multiple interfering layers, as opposed to DBS's direct electrode implantation that allows precise targeting. Addressing these challenges demands advancements in technology and methodology.

1.4.1 Monitoring Phases of Seizure Oscillation

Efficacy of neuromodulation depends on the timing of the stimulation relative to the ongoing rhythmic neural activity. Volume conduction of electrical fields in the tissues is instantaneous, thus informing tES timing relative to the rhythmicity of the target neuronal networks is critical. Using EEG to monitor deep brain seizures is challenging due to its limitations in directly capturing deep neuronal activity. Issues include the difficulty in interpreting EEG rhythms in relation to actual neuronal group activity, particularly with multiple seizure foci. Biological tissues may attenuate electrical signals, often leading to dampening low amplitude higher-frequency components below detection limit, which can mislead clinicians about a seizure's severity or location.

To tackle these challenges, approaches such as computational models can be employed to infer deep brain activity from surface EEG data. These models use forward and inverse problem-solving to simulate and deduce the origin of brain activity. Moreover, integrating EEG with other techniques like MEG or fMRI helps create a more complete view of brain activity. Additionally, machine learning algorithms can be developed to detect specific seizure patterns in EEG data, tailored to individual neurophysiological patterns. These methods collectively aim to enhance the accuracy of detecting and classifying deep brain seizures.

1.4.2 Side-Effect Profile of Transcranial Brain Stimulation

Targeting specific brain regions with transcranial stimulation involves complex challenges in neuroscience and medicine. For superficial areas, pinpointing the exact neural circuits without affecting neighboring ones is difficult due to spatial resolution limitations. Signal attenuation through the skin, skull, and cerebrospinal fluid also complicates the process, sometimes requiring increased stimulation intensity, which introduces additional risks. Individual differences in anatomy, like skull thickness, further impede the creation of standard protocols, highlighting the need for customized treatment strategies.

1.4.2.1 Stimulation Methodology

When addressing deep brain structures, the challenges intensify. Deep Brain Stimulation (DBS) is highly effective but carries significant risks like infection and hemorrhage due to its invasive nature. Non-invasive alternatives like transcranial magnetic stimulation (TMS) and focused ultrasound struggle with accuracy in deep tissue targeting without affecting other areas, and also face technical hurdles regarding the safe power levels needed for deep tissue stimulation. Transcranial electrical stimulation (tES) particularly faces difficulties due to the weakening of electrical fields as they travel deeper into the brain.

Despite these challenges, for superficial brain regions, tES has shown promise due to its non-invasive nature and the possibility of using electrode arrays to focus the electric field. Computational models can help customize treatments to individual anatomical variances. For deeper structures, techniques such as temporally interfering electrical fields (Temporal Interference—TI) or Intersectional Short Pulse stimulation (ISP) can target deep brain areas non-invasively.

The possibility of integrating tES with other techniques like imaging or focused ultrasound can be used to enhance precision and efficacy in stimulating deep brain areas. These approaches aim to bridge the gap between non-invasive flexibility and the precision of invasive methods like DBS.

1.4.2.2 Modeling

The development of effective neuromodulation strategies faces numerous challenges, with various approaches being explored to overcome them. Personalized stimulation protocols that consider individual anatomy and physiological biomarkers utilize pre-stimulation imaging to guide stimulus application and computational models to simulate stimulus propagation and optimize parameters. However, there are obstacles in this process. To properly estimate neuronal readout, the brain's complexity requires non-linear models to consider its diverse cell types and tissues, each with unique electrical properties, necessitating extensive computational resources and precise data from techniques like MRI. Moreover, the brain's dynamic nature, influenced by states like sleep and attention, makes static models insufficient and calls for adaptive, more complex modeling that adds computational demands Validating these models is another challenge, often requiring invasive methods such as intracranial electrode placement for empirical data, which is risky and limits the development process. Therefore, methods that harness advances in computational methods, such as machine learning, and utilize more powerful computing systems are needed to address these issues.

1.4.2.3 Safety Considerations of Stimulus Dose and Intensity

The safety considerations for transcranial electrical stimulation (tES), including techniques like transcranial direct current stimulation (tDCS) and transcranial alternating current stimulation (tACS), are primarily centered on determining the optimal stimulus dose and intensity to minimize risks and avoid adverse effects. Precise dosing is crucial as excessive stimulation can lead to skin irritation under the electrodes, discomfort, and in rare cases, more serious neural effects such as seizures or unwanted changes in brain plasticity. On the other end of the spectrum, insufficient stimulation may result in no therapeutic gain.

Safety guidelines for tES advocate for limits on current intensity, duration of stimulation, and electrode size and placement to manage the risk of adverse effects. These recommendations are informed by clinical trials and experimental data that consider factors like individual sensitivity, the electrical properties of the skull and tissues, and the potential for long-term effects from repeated stimulation sessions. As mentioned above, there is an emphasis on personalizing tES protocols to accommodate inter-individual anatomical and physiological differences that influence the electric field distribution in the brain. However, there is a need for further refining these guidelines by exploring the mechanisms of action in tES and developing technologies for real-time monitoring of brain responses, which can guide the adjustment of stimulation parameters during treatment. Such advancements have potential to maximize both the efficacy and safety of tES applications.

2. Limitations of Existing Seizure Detection & Neuromodulation in Epilepsy

Compared to drug treatment, device therapies (i.e., stimulation) can be delivered on demand, only when neural circuits display pathological patterns, thereby avoiding side effects during quiescent periods, which may represent >99% of a person's life, according to some estimates.

An ideal device therapy for neuromodulation should be 1) on demand; 2) spatially and temporally precisely targeted; 3) non- or minimal invasive; 4) should have high therapeutic efficacy, preferably instantaneously; 5) should lack side effects and should not cause discomfort to the patients; and 6) wearable and aesthetically acceptable. None of the modalities of the currently used neuromodulation approaches meet all of these criteria, each neuromodulation approach has advantages and drawbacks.

2.1 General Limitations of Seizure Detector Embodiments

State-of-the-art seizure detectors have made significant strides in monitoring and responding to epileptic seizures. However, they face considerable limitations, particularly in the precise detection of seizure rhythmicity. While they can often detect the onset of seizures, deciphering the nuanced rhythms and patterns that unfold during the transition from interictal to ictal states eludes current technologies. This gap limits the potential for proactive and finely-tuned therapeutic interventions.

A further challenge lies in the inherent data imbalance characteristic of seizure events. Ictal (seizure) episodes are much less frequent than interictal (non-seizure) episodes, leading to a training data set that is skewed and often biases algorithms towards predicting the more common interictal state. This discrepancy can inflate the rate of false negatives, as detectors become overly cautious to avoid false positives, making it challenging to maintain a delicate balance between sensitivity and specificity.

The complexity of the algorithms themselves presents another layer of difficulty. They might excel within controlled training environments but struggle to generalize to new patient data due to the highly individualized nature of seizure expressions. The dynamic and non-stationary nature of brain signals adds to this complexity, as it demands the algorithms to adjust and maintain accuracy consistently over time.

Hardware constraints also impede the efficacy of current seizure detectors. The EEG signals that non-invasive systems rely on can be marred by noise and external interferences, leading to inaccurate detections. Furthermore, the limited spatial resolution of EEG complicates the precise localization of seizure origins, particularly when they arise from deep brain structures.

Integrating these detectors into clinical practice brings its own set of challenges. Real-time processing of EEG data requires substantial computational resources, which may not always be available in a wearable or implantable device in clinical settings. Moreover, the systems must provide clear, actionable feedback to both patients and healthcare providers, which necessitates the development of intuitive interfaces suitable for individuals without specialized training.

2.2 General Limitations of Neurostimulation Solutions

TMS is a well-tested method: its power can be calibrated for each individual, it can deliver focal stimulation, and it has efficacy in major depression. Yet, TMS requires complex instrumentation, delivers only pulses, produces loud noise, and its penetration is limited to superficial brain areas. TFUS uses mechanical energy to focal brain regions in humans and experimental animals, however the mechanical vibration and bubble formation carries the risk of tissue damage.

Electrical stimulation methods can be either non-invasive or invasive. Amongst the invasive approaches, the Responsive Neurostimulation System (RNS, Neuropace) delivers patterned electrical stimulation directly to the epileptogenic focus upon detecting an electrographic seizure. However, RNS requires an invasive brain surgery, increasing risk and cost and can only target a limited number of epileptic focuses. ANT DBS (anterior nucleus of the thalamus deep brain stimulation) and VNS (vagal nerve stimulation) share some disadvantages with RNS including surgical risks and incomplete seizure control and lack the desired temporal precision. Preventing epileptic seizures and terminating them at their emergence both employ neuromodulation but differ in their approach, timing, and sometimes in technology. While preventive neuromodulation aims for sustained control of neural activity to minimize the occurrence of seizures, termination at emergence aims for rapid, on-demand intervention. VNS, DBS, and RNS are key technologies in the preventive approach, whereas RNS aligns with the approach of terminating seizures at their onset. Both strategies have limitations and are the subject of ongoing research to improve their efficacy and minimize their drawbacks. Therefore, a non-invasive or minimally-invasive, closed-loop stimulation system would represent a major advancement.

Non-invasive known TES is popular because of its convenience and potential as a chronic therapy. The advantages of TES include low cost, portability, and potential in-home applications, which have fueled a proliferation of human trials. A major disadvantage of known TES is that it stimulates the skin, subcutaneous nerves, the retina and cochlea/vestibular organs more effectively than the brain parenchyma and produces weak, diffuse fields.

There are critical barriers to overcome in translating TES to human use. In humans, existing TES protocols are limited to low-intensity currents (typically $\leq$2 mA) due to stimulation of scalp nerves, the retina and the vestibular apparatus. Since stronger currents induce peripheral side effects and confound experimental protocols, known TES methods (e.g., two sponge electrodes to deliver current to the scalp) result in weak, diffuse fields reaching the cortical surface ($\leq$0.8 V/m). Previous experiments demonstrated that such electric fields are usually ineffective at entraining ongoing neural oscillations or consistently bringing neurons to firing threshold. Further, individual differences in human head anatomy result in variable intensities of the induced electrical field. The attenuated fields induced by known TES methods, variability in human head anatomy, and confounding effects of peripheral sensation likely explain the small effect sizes and challenges in replicating behavioral results.

The next generation of TES technology should implement 3 advancements: 1) delivery of stronger currents to the brain while minimizing peripheral and indirect effects, (2) simultaneous stimulation and recording of brain activity for quantitative measurements of acute TES-induced neurophysiological effects; and (3) improved spatial and temporal targeting.

2.3 General Limitations of Automated Seizure Onset Detection 2.3.1 Offline Seizure Detectors Offline seizure detectors analyze recorded EEG data to pinpoint seizures, primarily for research and diagnostics. Machine learning models, including neural networks and support vector machines, can be used, which providing high accuracy but demand significant computational power and extensive, well-annotated datasets which can be challenging to procure due to data privacy concerns. Frequency-domain analysis is another method used to dissect EEG signals into constituent frequencies to detect anomalies. However, its effectiveness can be hampered by noisy data, necessitating meticulous pre-processing to avoid false positives. The high cost of quality EEG recording equipment and the trade-off between affordability and data fidelity with portable devices pose additional obstacles. Moreover, the voluminous data generated by high-quality EEGs present storage challenges. One of the main hurdles in creating effective offline seizure detectors is the individual variability in seizure expression, which impedes the development of a one-size-fits-all solution and personalizing these systems can be cost and resource intensive.

Some offline seizure detectors employ machine learning algorithms to predict seizure onset zones based on pre-surgical MRI and EEG data. However, the resource-intensive nature of the machine learning algorithms used has limitations for on-the-go diagnosis or monitoring. Other systems utilize advanced digital signal processing, but are high sensitivity to noise and artifacts. Portable systems are more accessible; however, these systems have lower data quality compared to clinical EEG systems meaning that detection algorithms may need further tuning to account for noise and artifacts.

2.3.2 Implantable and Wearable EEG Monitoring and Data Collection Units

Analog Front-Ends (AFEs) are often used in EEG systems for seizure detection, handling signal amplification, preconditioning, and digitization with energy efficiency in a compact design. Some current areas for improvement in EEG systems are balance accuracy, power consumption, and signal fidelity in AFEs, optimizing amplifiers, filters, and converters to enhance signal-to-noise ratios and reduce noise. Some areas for improvement include low-power designs, programmable filters, and compressed sensing to extend device battery life and adapt to individual signal variations. Challenges to implementing these improvements include interference, noise management, and regulatory compliance.

Wearable EEG devices offer consumer-level brain data collection but fall short in clinical precision and signal quality, prone to motion artifacts and external noise. Maintaining quality data alongside long battery life is challenging, and real-world application often reveals performance drops due to uncontrolled interferences. Additionally, data security concerns and stringent medical device regulations make market entry for clinical use both costly and time-consuming.

2.3.3 Online Seizure Detectors—Firmware and Hardware EEG Detectors

The technological frontier of seizure management has increasingly moved toward online, real-time solutions that not only identify but also potentially mitigate epileptic episodes as they occur. Firmware-based seizure detectors form a crucial part of this paradigm, and their embodiments have been diversifying with advances in hardware and software.

Existing seizure detection devices configured to be implanted in the brain (e.g., Neuropace RNS) provide seizure management, but the surgical implantation poses risks, such as infection or hemorrhage, and necessitates periodic battery replacement surgeries, typically every few years. Furthermore, the clinicians often undertake an iterative customization process to ensure the device's settings maintain optimal performance. Additionally, while designed for efficient power usage, battery life remains a constraint, as does the need for systematic data uploads to clinical databases for review. Ultimately, these systems are predominantly reserved for patients with intractable epilepsy, where the invasive nature and intensive management of the device may be justified. Some Deep Brain Stimulation (DBS) devices for epilepsy (e.g., Medtronic DBS device) provide continuous stimulation to the thalamus and are not adaptive like closed-loop systems. Adaptive DBS systems require customization to individual patient physiology to maximize effectiveness and minimize false positives and face challenges include patient variability, the need for frequent clinical adjustments, and the complexity of implantable device management, with specific concerns about accurately isolating seizure activity and managing power consumption for patient compliance. Wearable devices for seizure detection (e.g., ASICs, Empatica) face significant challenges. Customizing these devices for individual seizure patterns is difficult, and integrating complex machine learning algorithms requires significant design changes. Regulatory approval processes for medical devices add to the complexity and slow down updates and adaptability.

Additionally, wearable devices cannot provide the comprehensive monitoring that scalp or intracranial EEGs offer. Furthermore, they are limited in the type of seizures they can detect and have shown some susceptibility to false positives due to activities like exercise or stress that can also elevate electrodermal activity (EDA) and heart rate.

Responsive Vagus Nerve Stimulation (VNS), faces challenges of non-specificity of heart rate spikes which can lead to false positives and unintended stimulations. Implantation risks, limited seizure-type effectiveness, and maintenance costs, including battery replacement, are also concerns. Balancing detection accuracy and minimizing false positives is critical for these devices, which are more costly than non-responsive VNS systems.

The systems, devices, and methods described herein address the drawbacks of the current systems by providing benefits including: (1) providing minimally invasive seizure detection and neuromodulation; (2) employing accurate, real-time seizure detection protocols; (3) implementing power conscious algorithms and hardware; (4) easy to maintain (e.g., easy to supply power, provide software updates, etc.), (5) supplying spatially targeted neurostimulation; (6) providing precise detection of patterned brain activity and rhythmicity of brain signals; and (7) delivering phase-aligned neurostimulation based on the rhythmicity of brain signals.

3. Overview of System

FIG. 1A shows a schematic block diagram of a system 100 for monitoring and modulating brain activity, according to an embodiment. System 100 can deliver responsive electrical stimulation in a closed-loop manner and can offer real-time or near real-time monitoring of induced neurophysiological effects. After detecting a targeted brain pattern (e.g., an epileptic seizure), the system may deliver high-intensity ultra-short electrical stimulation impulses non-invasively or minimal-invasively to diminish or stop the neural oscillations underlying the epileptic seizure. The stimuli are delivered in time and space, relative to the emerging seizure rhythm patterns, such that they diminish or terminate the seizure. System 100 may include an implantable device 110 including one or more electrodes 112 electrically coupled to one or more processors 120 via an Analog Front-End Data Acquisition module 117 and an Analog Front-End Stimulation module 119. The processor(s) 120 may be operatively coupled to a memory 114, one or more communication interfaces or communication modules 118, and may optionally be coupled to a battery 116. In some embodiments, the processor(s) 120 may optionally be coupled to one or more additional sensor(s) 113 either directly or via the Analog Front-End Data Acquisition module 117 and/or an Analog Auxiliary Data Acquisition Module. In some embodiments, the battery 116 may be connected to an external power supply 115. In some embodiments, the battery 116 may not be included in the implantable device 110, and instead the implantable device 110 may be powered by the power supply 115 positioned external to a body of the patient. The communication module(s) 118 may be coupled to one or more components external to the body of the patient such as one or more processor(s) 132, one or more input/output (I/O) devices, and optionally a display 139. In some embodiments, the processor(s) 132, the I/O device(s), and/or the display 139 may be onboard a compute device used by a clinician, e.g., to program the device, monitor functioning of the device, and/or control operation of the device.

In some embodiments, the electrodes 112 may be implanted in a body of the patient (e.g., the head). The electrodes 112 may be implanted for practical, wearability, and/or aesthetic reasons. In some embodiments, the electrodes 112 may be placed in the subgaleal space under the scalp, above the skull. In some embodiments, the electrodes 112 may be positioned in other locations such as, but not limited to, in the brain, in the subdural space, or in the epidural space of the patient. In some embodiments, at least a subset of electrodes from the plurality of electrodes is implanted in one of the subgaleal space, the subdural space, the epidural space, or the brain. In some embodiments, the electrodes 112 may not be implanted (e.g., may be placed external to the patient). For example, the electrodes 112 may be non-invasive scalp electrodes or optical sensors or magnetic sensors placed on or close to the scalp. In some embodiments, the electrodes 112 may be configured to measure a brain activity of the patient. For example, the electrodes 112 may be configured to measure EEG signals. EEG signals may include any brain activity data recorded either by scalp EEG, subgaleal or subdermal EEG, ECoG (Electrocorticogram) recorded by subdural electrodes, optical or magnetic acquisition, and/or penetrating electrodes, such as DBS or stereoEEG leads. In some embodiments, the implantable device 110 includes between 1 electrode and 256 electrode contacts, inclusive of all ranges and subranges therebetween. In some embodiments, the implantable device 110 may include one or more recording and/or stimulation electrodes. In some embodiments, the implantable device 110 may include 30 recording and/or stimulation electrodes, one ground electrode, and one reference electrode. In some embodiments, the electrodes 112 may be arranged on one or more electrode leads (e.g., columns, strips, etc.). In some embodiments, the electrodes 112 may be arranged on one electrode lead to 10 electrode leads, inclusive of all ranges and subranges therebetween. In some embodiments, the electrodes may be arranged on four electrode leads with each electrode lead including eight electrodes 112. The electrode(s) 112 may be coupled to the processor(s) 120 and/or any component of the implantable device 110 via one or more electrode cables.

In some embodiments, the Analog Front-End Data Acquisition module 117 and/or Analog Front-End Stimulation module 119 may be implemented in hardware and/or software. In some embodiments, the Analog Front-End Data Acquisition module 117 and/or Analog Front-End Stimulation module 119 may include any suitable circuitry to acquire data and generate electrical output, respectively. In some embodiments, the Analog Front-End Data Acquisition module 117 and/or Analog Front-End Stimulation module 119 may include any suitable code to cause the implantable device 110 to acquire data and generate electrical output, respectively. In some embodiments, the Analog Front-End Data Acquisition module 117 and/or the Analog Front-End Stimulation module 119 may include one or more analog-to-digital converters (ADC) and/or digital-to-analog converters (DAC).

In some embodiments, the additional sensor(s) 113 may be configured to record one or more additional biosignals, device-related parameters, behavioral parameters, wearable sensor parameters, and/or environmental parameters, and these measurements may be stored for further analysis. In some embodiments, the additional sensor(s) 113 may be used to collect information related to the functionality of the system 100. In some embodiments, the additional sensor(s) 113 may be used to measure biosignals, and the biosignals may be used to aid in seizure detection. In some embodiments, the additional sensor(s) 113 may be configured to be implanted in the patient. For example, the additional sensor(s) 113 may include sensors located in or on the implantable device 110 and configured to take measurements related to functionality of the implantable device 110 (e.g., power consumption, temperature, movement of the device and/or electrodes, etc.). In some embodiments, the additional sensor(s) 113 may be wearable sensors (e.g., placed on a skin of the patient). In some embodiments, the additional sensor(s) 113 may be configured to measure biosignals including, but not limited to, electromyography (EMG) data, electrocardiogram (ECG) data, respiratory rate, heart rate or variability in heart rate, and/or body temperature. In some embodiments, the additional sensor(s) 113 may be configured to measure environmental signals and/or behavioral signals such as, for example, acceleration, time, video data, input from wearable devices, user input, etc.

The brain activity data (e.g., the EEG signal) is analyzed (e.g., by the processor 120) in real-time or in near real-time to decipher whether the EEG pattern is indicative of an epileptic seizure. For example, the processor 120 may be configured to detect a precursor activity leading to a seizure, an onset of the seizure, or a presence of the seizure. During seizure periods the highly synchronous neuronal discharges (sharp rhythmic deflections on the EEG channels) can be detected in real time or near real-time. In some embodiments, the electrodes 112 may be configured to deliver electrical stimulation (e.g., deliver charge or current) to a tissue (e.g., brain tissue or nearby tissue) of the patient based on the brain activity measured. For example, once a seizure pattern is detected, electrical pulses may be delivered through one or more of the electrodes 112 in order to interfere with the development and continuation of the seizure. In some embodiments, the electrodes 112 may be configured to deliver Intersectional Short-Pulse (ISP) Stimulation. ISP stimulation involves delivery of brief electrical pulses in a distributed manner across the scalp (or subgaleal space), resulting in stronger, more spatially focused electric fields reaching the brain compared to known TES. ISP stimulation exploits the temporal integration property of the cell membranes to reach a spatially restricted effect on targeted brain regions. In some embodiments, the system 100 may be configured to deliver high intensity ISP stimulation (e.g., up to about 80 milliamps (mA)) by distributing current entry as ultra-short pulses across multiple electrodes over the scalp (or subgaleal space). Neurons located in a target brain region integrate the effects of discrete, high intensity bursts, due to relatively short integration time constants of their cell membranes. In some embodiments, the system 100 may be configured to deliver current pulses (e.g., via the electrodes 112) having an amplitude of about 0.1 mA to about 80 mA, inclusive of all ranges and sub-ranges therebetween. In some embodiments, the system 100 may be configured to deliver current pulses (e.g., via the electrodes 112) having an amplitude of about 0.1 mA to about 80 mA. In some embodiments, the current pulses (e.g., the ISP stimulation) may be configured to disrupt or interfere with at least one oscillation in brain activity contributing to the seizure. Experiments show ISP stimulation has can instantaneously modulate brain activity in healthy volunteers, with only mild to moderate side effects. Further information on experiments related to timing of electrical stimulation is described in Vöröslakos, M., Takeuchi, Y., Brinyiczki, K., Zombori, T., Oliva, A., Fernández-Ruiz, A., Kozák, G., Kincses, Z. T., Iványi, B., Buzsáki, G., & Berényi, A. (2018). Direct effects of transcranial electric stimulation on brain circuits in rats and humans. Nat Commun, 9(1), 483 (hereinafter, "Vöröslakos et al."); Jirsa, V. K., Stacey, W. C., Quilichini, P. P., Ivanov, A. I., & Bernard, C. (2014). On the nature of seizure dynamics. Brain, 137(8), 2210-2230 (hereinafter, "Jirsa et al."); and Kozák, G., & Berényi, A. (2017). Sustained efficacy of closed loop electrical stimulation for long-term treatment of absence epilepsy in rats. Scientific Reports, 7(1), 1-10, (hereinafter, "Kozák & Berényi") the disclosures of each of which is hereby incorporated by reference in its entirety.

Properly timed ictal stimulation can generate instantaneous (or near instantaneous) and deterministic extracellular electric fields, which can interfere with rhythmic neuronal network oscillations, as described in Berenyi et al., Ozen et al., and Vöröslakos et al. These rhythmic oscillations and other oscillatory patterns (e.g., from seizure to desynchronized physiological patterns) can be altered with the delivered current (e.g., via the electrodes 112) by creating a destructive interference, as described in Jirsa et al. Some research has shown properly timed transcranial electrical pulses can stop seizures in rodents (as described in Berenyi et al. and Kozák & Berényi) and in human patients, with negligible side effects.

In some embodiments, the system 100 may include processor(s) 132, I/O device(s) 134, and may optionally include a display 139 all of which may be configured to be operatively coupled to the implantable device 110 via the communication module(s) 118. In some embodiments, the processor(s) 132, the I/O device(s) 134, and the display 139 may be onboard a compute device operated by the clinician (e.g., a desktop computer, a laptop, a tablet, a phone, etc.). In some embodiments, the system 100 may communicate with other compute devices such as a patient device, a server, and/or other devices. In some embodiments, the other compute devices may be configured to collect data from the implantable device 110, process and/or analyze some or all of the data from the implantable device 110, store the data for later analysis, train and/or refine a detection model, train and/or refine a stimulation generation model, enable programming of the implantable device 110, allow control of the implantable device 110, and/or relay data or information to the implantable device 110.

In some embodiments, the processors 120, 132 can be any suitable processing device(s) configured to run and/or execute a set of instructions or code. For example, the processors 120, 132 can be and/or can include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data and/or power transfer), and/or the like. The processors 120, 132 can be, for example, a general-purpose processor, central processing unit (CPU), microprocessor, microcontroller, Field Programmable Gate Array (FPGA), an Application Specific Integrated Circuit (ASIC), a processor board, a virtual processor, and/or the like. In some embodiments, computations are shared between a field-programmable gate array (FPGA) chip and a microcontroller to optimize for real-time or near real-time operations. The processors 120, 132 can be configured to run and/or execute application processes and/or other modules, processes and/or functions associated with the system 100. The underlying device technologies may be provided in a variety of component types, for example, metal-oxide semiconductor field-effect transistor (MOSFET) technologies like complementary metal-oxide semiconductor (CMOS), bipolar technologies like generative adversarial network (GAN), polymer technologies (e.g., silicon-conjugated polymer and metal-conjugated polymer-metal structures), mixed analog and digital, and/or the like.

In some embodiments, the processors 120, 132 can be configured to receive data from the electrodes 112 and optionally the additional sensor(s) 113 and to process that data (e.g., to determine a pattern of brain activity in the patient, to detect seizure activity, etc.). Alternatively or additionally, the processors 120, 132 can be configured to send the data from the electrode(s) 112 and/or the additional sensor(s) 113 to one or more remote devices (e.g., via a network or the cloud) for further processing and/or analysis. In some embodiments, the processor(s) 132 may be configured to receive data from the electrodes 112 and/or additional sensor(s) 113, train and/or optimize a seizure detection model or algorithm, train and/or optimize a stimulation generation algorithm, and send instructions related to the seizure detection model or algorithm and stimulation generation algorithm to the processor(s) 120 embedded in the implantable device 110. In some embodiments, the processor 120 may be configured to receive brain activity data from the electrodes; to detect a precursor activity leading to a seizure, an onset of the seizure, or a presence of the seizure; to determine (e.g., based on a pattern in the brain activity) a timing with which to deliver current pulses to a brain of the patient to disrupt at least on oscillation in brain activity contributing to the seizure; and/or activate a subset of electrodes to deliver the current pulses to a target region of the brain of the patient according to the timing.

In some embodiments, the processor(s) 120, 132 may be configured to quantify the pattern in the brain activity data by calculating a measure of rhythmicity at predetermined frequency components of the brain activity data. In some embodiments, the measure of rhythmicity may include phase values of the signal crossing a threshold, detection of peaks in the signal, detection of the signal crossing a threshold, etc. In some embodiments, the one or more processors may be configured to determine the timing to stimulate based on at least one of a phase of broadband brain activity data, a phase of a frequency band component of the brain activity data, or a frequency of the brain activity data. In some embodiments, the processor(s) 120, 132 is configured to determine the timing based on a phase of the brain activity data, and to active the subset of electrodes 112 to deliver the current pulses one of immediately or after a predetermined delay, and with a predetermined frequency (e.g., "Responsive Closed-Loop" mode). In some embodiments, the processor(s) 120, 132 may be configured to recognize the pattern of brain activity and to activate the subset of electrodes 112 to deliver the current pulses one of immediately or after a predetermined delay, the one or more current pulses configured to align with an inherent rhythmicity of the brain activity data (e.g., "Adaptive Closed-Loop" mode). In some embodiments, the processor(s) 120 may be configured to execute one or more functions to receive measurements from the electrode(s) 112 and/or additional sensor(s) 113, analyze the measurements, and generate an electrical stimulation to be delivered via the electrodes 112 based on the analysis, explained in further detail below with respect to FIG. 1B.

In some embodiments, the memory 114 can be any suitable memory device(s) configured to store data, information, computer code or instructions (such as those described herein), and/or the like. In some embodiments, the memory 114 can be and/or can include one or more of a random access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some embodiments, the memory 114 can store instructions to cause the processor(s) 120 to execute modules, processes, and/or functions associated with the system 100, such as models, calculations, or other algorithms to analyze brain activity captured by the system 100. In some embodiments, the memory 114 may have both volatile and non-volatiles storage elements to ensure proper device operation even after a system shutdown or restart due to battery depletion. In some embodiments, the memory 114 may also be configured to at least temporarily store data collected by the implantable device 110, until the data is transmitted to a user device, a clinician device, and/or a remote server.

In some embodiments, the communication module(s) 118 can be any suitable device(s) and/or module(s) that can communicate with the implantable device 110 (e.g., electrodes 112, additional sensor(s) 113, etc.), a network (e.g., a local area network (LAN), a wide area network (WAN), or the cloud), or external devices (e.g., a patient device, a clinician device, etc.). In some embodiments, the communication module(s) 118 can be configured to communicate information between the implantable device 110 and the processor(s) 132, I/O device(s) 134, and/or display 139. Moreover, the communication module(s) 118 can include one or more wired and/or wireless interfaces, such as, for example, Ethernet interfaces, optical carrier (OC) interfaces, and/or asynchronous transfer mode (ATM) interfaces. In some embodiments, the communication module(s) 118 can be, for example, a network interface card and/or the like that can include at least an Ethernet port and/or a wireless radio (e.g., a WI-FI® radio (Wifi), a BLUETOOTH® radio (Bluetooth), cellular such as 3G, 4G, 5G, etc., 802.11X Zigbee, etc.). In some embodiments, the communication module(s) 118 include one or more satellite, Wifi, Bluetooth, or cellular antenna. In some embodiments, the communication module(s) 118 can be communicably coupled to an external device (e.g., an external processor 130) that includes one or more satellite, Wifi, Bluetooth, or cellular antenna, or a power source such as a battery or a solar panel. In some embodiments, the communication module(s) 118 may include a dual transformer communication interface.

In some embodiments, the communication module(s) 118 can be configured to receive signals from the electrodes 112 and/or the additional sensors 113 and to send these signals to the processor(s) 132. In some embodiments, the communication module(s) 118 may also be configured to communicate signals to the implantable device 110, for example, instructions for the seizure detection model or algorithm and/or instructions for stimulation generation.

In some embodiments, the battery 116 may include a rechargeable battery (e.g., Li-ion, Lithium Iodine (LiI), Lithium/Silver Vanadium Oxide (Li/SVO), Lithium/Carbon Monofluoride (Li/CFx), QMR® cells, etc.) and is configured to provide electrical power to the electrodes 112, the additional sensor(s) 113, the memory 114, the communication module(s) 118, and/or the processor 120. In some embodiments, in which the battery 116 is a rechargeable battery, the system 100 may by coupled to the external power supply 115 to recharge the battery 116. In some embodiments, the battery 116 may be configured to be implanted in the patient. For example, the battery 116 may be implanted in a chest of the patient or a head of the patient. In some embodiments, the battery 116 may be implanted under skin of the chest of the patient and/or under muscle in the chest of the patient. In some embodiments, the battery 116 may be configured to be positioned external to the patient. In some embodiments, the battery 116 may be disposed on a head of the patient. For example, the battery 116 may be worn over or around an ear of the patient. In some embodiments, the battery is implanted along with the implantable device 110, but may form a standalone unit, connected to the implantable device 110 through one or more battery cables, to allow end-of-life-cycle replacement without the need of replacing the implantable device 110. The battery cable(s) establish not only power-line connections but may also establish a communication channel between the implantable device 110, the battery, and the related supplementary electronics, if any (e.g., battery charger).

In some embodiments, the I/O device(s) 134 may be configured to receive input from a user (e.g., a clinician) to program and/or monitor the functionality of the device. In some embodiments, the display 139 may be configured to display information to the user (e.g., the clinician), the information including raw and/or processed brain activity signals collected with the electrodes 112, patient history, data relating to performance of the detection algorithm, stimulation parameters used by the implantable device 110, imaging data of the brain of the patient (e.g., MRI images), or any other information that may be useful in programming and/or monitoring functionality and usage of the system 100.

Figure 1B:
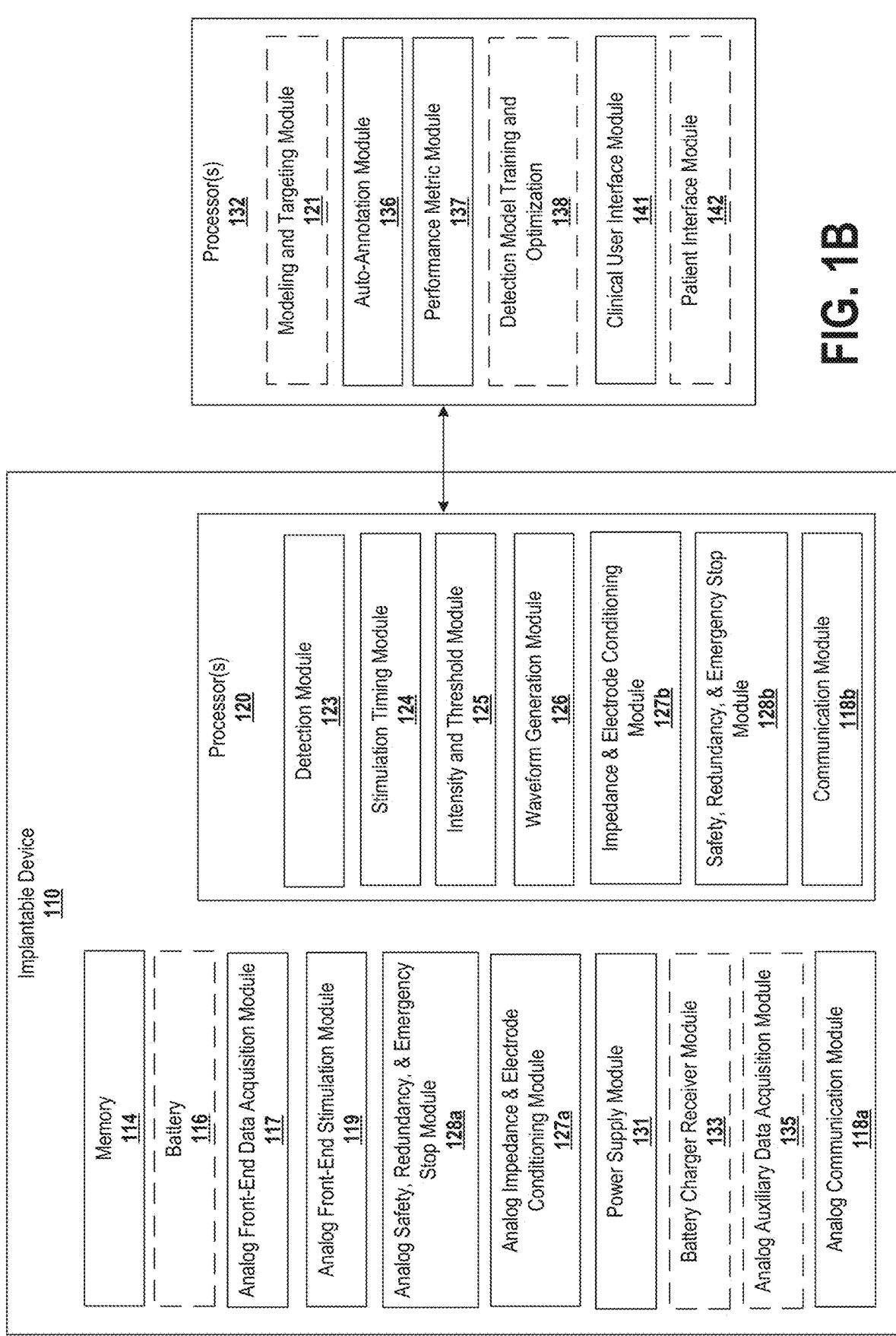
FIG. 1B is a schematic block diagram of processors of the system including modules that when executed allow the system to monitor brain activity and deliver electrical brain stimulation, according to an embodiment.

FIG. 1B shows software and/or hardware modules associated with the system 100. The system 100 is configured to acquire and record neuronal activity by electrical means and to detect specific patterns in the acquired signal in real-time or near real-time. The system 100 acquires the electrical correlates of the neuronal activity (either of the brain, spinal cord or peripheral nerves) through the electrodes 112. In some embodiments, the processor(s) 120 may include modules that cause the processor (120) to acquire signals (e.g., signals associated with brain activity of the patient), process and/or analyze the signals, and deliver electrical stimulation based on the processing and/or analysis. In some embodiments, the modules may store instructions for performing one or more functions. In some embodiments, the modules may be associated with hardware (e.g., analog-to-digital converter (ADC), current source, etc.) that may facilitate the processor(s) 120 in performing the one or more functions. In some embodiments, one or more hardware components may be integrated into the processor(s) 120. In some embodiments, one or more hardware components may alternatively and/or additionally be in the implantable device 110 and connected to the processor(s) 120. In some embodiments, the processor(s) 120 may include one or more functional modules that correspond to an analog module in the implantable device 110.

The implantable device 110 may include any one or all of the following modules. In some embodiments, modules that include code may be executed in a predetermined order such that the system 100 may perform closed-loop neurostimulation for seizure prevention or termination.

The Analog front-end and data acquisition module ('AF-DAQ') 117 may be configured to acquire electrical signals captured by the electrodes 112. In some embodiments, the Analog Front-End Stimulation Module 119 may be configured to deliver current through the one or more electrodes 112 of the implantable device 110. In some embodiments, the Auxiliary Data Acquisition Module ('AUXDAQ') 135 may be configured to capture signals from auxiliary sources (e.g., the additional sensor(s) 113). In some embodiments the AUXDAQ can capture signals from auxiliary sources simultaneously and synchronously with the neuronal data acquisition. In some embodiments, the signals captured from the auxiliary sources may either be biosignals (e.g., EMG, ECG or hearth rate), or environmental and behavioral signals such as for example acceleration, time, video data, input from wearable devices, user input, etc. In some embodiments, the Analog Front-End Stimulation Module 119, the Analog Front-end Data Acquisition Module 117, and the Auxiliary Data Acquisition Module 135 may be implemented by hardware and/or software.

The acquired data of various modalities, the device performance and status related metrics, and the patient specific device settings may be stored in the memory 114. The memory 114 may have both volatile and non-volatiles storage elements to ensure proper device operation even after a system shutdown or restart due to battery depletion.

The implantable device 110 may be configured to deliver electrical stimulation to the human body through similar or the same electrodes 112 as those used for signal acquisition. The stimuli can be delivered either manually by the operator via a user module (e.g., the I/O device(s) 134 and/or the display 139) or automatically. When the system 100 is set to automatic, the stimuli can be delivered in several modes:

In an "Open-loop" mode, where the timing of the stimuli delivery is not contingent upon any aspects of the signals acquired.

In a "Responsive Closed Loop" mode, whereby the stimuli are delivered upon the real-time detection of a specific pattern within the acquired signals, either immediately or following a predetermined delay, and if repeated, occur with a preset frequency and pattern.

In an "Adaptive Closed-loop" mode, meaning the stimuli are administered upon recognition of a certain pattern within the acquired signals, either immediately or after a predetermined delay, and if repeated, the pattern of delivery aligns with the inherent rhythmicity of the acquired signal (e.g., the stimuli pattern is adapted based on the brain activity).

The Detection Module 123 may include various complex feature extraction and decision-making algorithms the detect in real-time or near real-time the presence of certain patterns and/or features in the acquired signals, for example typical landmarks of epileptic seizures. The detected onset of these patterns, either transient or rhythmic, may be used to trigger the stimulus delivery in Responsive Closed-loop mode and/or Adaptive Closed-loop stimulation mode. In some embodiments, the implantable device 110 may be configured to be switched (e.g., manually or automatically) between the one or more modes of stimulation delivery. The decision-making model of the Detection Module 123 is parameterized (e.g., trained) by a Detection Model Training and Optimization Algorithm 138 (described in further detail below), using previously recorded and properly annotated ground truth data. This data may originate from either the same patient (i.e., patient-specific detector) or from other patient(s) (i.e., cross-patient detector).

The Stimulation Timing Module 124 may be configured to cause the processor 120 to further analyze the fine structure and rhythmicity of the acquired signal. The Stimulation Timing Module 124 may include code and/or instructions for detecting the instantaneous phase values of preset frequency components of either transient or permanent oscillations. The crossings of preset phase values (e.g., occurrence of a peak, a trough or crossing of a preset phase or amplitude value) may then trigger stimulus delivery when the implantable stimulation system 110 is in the "Adaptive Closed-loop" stimulation mode, aligning this way each repeat of the stimulus to the same phase of a selected ongoing oscillation.

The peak intensity of the applied stimulus waveform can be set either manually or based on a semi-automatically titrated patient-, target-, and stimulus waveform-specific sensation and tolerance thresholds. The Intensity and Threshold Module 125 may provide code and/or instructions for measuring the maximum intensity (i.e., amplitude) of a selected stimulus waveform delivered to a selected target area (e.g., of the brain of the patient) that is non-sensible (e.g., not perceived by the patient), and also measures the maximally tolerated stimulus intensity by the patient. The module can set up a sequence of ramping intensities, in which the first stimulus is delivered at a lower intensity (e.g., at or below the perception level), and if the stimulation is repeated again within a certain time window (i.e., as part of a stimulation train), the intensity may be gradually increased repeat by repeat to a maximum intensity level (e.g., to the maximum tolerable level).

The Waveform Generation Module 126 may be configured to set up the desired digital stimulation waveform, generate the analog stimuli, and transmit the analog stimuli through selected electrodes 112 (e.g., a subset of the electrodes). Depending on the desired stimulation mode, it may rely on timing and stimulus parameter data of the Detection 123, Stimulation Timing 124, and Intensity & Threshold Modules 125.

To ensure safe and stable operation, the impedances of the electrode-tissue interfaces are regularly verified by the Impedance & Electrode Conditioning Module 127b and the Analog Impedance & Electrode Conditioning Module 127a. In some embodiments, the Impedance & Electrode Conditioning Modules 127a, 127b may be configured to deliver current and/or to sink (e.g., via active counterbalancing) or remove charge (e.g., passively, via grounding) through electrodes 112 in order to improve contact impedance and signal quality or lessen any direct current bias originating from electrochemical reactions at the electrode-tissue surfaces. In some embodiments, the Impedance & Electrode Conditioning Modules 127a, 127b may be implemented in hardware and/or software. In some embodiments, this module may include one or more hardware components to deliver current and/or to sink or remove charge through the electrodes 112. Patient safety is further secured by the Safety, Redundancy and Emergency Stop Module 128b and the Analog Safety, Redundancy, and Emergency Stop Module 128a. In some embodiments, the Safety, Redundancy, and Emergency Stop Modules 128a, 128b may (1) measure the load on each electrode 112 and ensure the load does not to exceed established tissue safety limits, (2) supervise the proper functioning of the critical system components preventing excessive stimulation due to Hardware or Firmware failure, and/or (3) establish a mechanism to intentionally abrupt stimulation by user intervention.

The Communication Module 118b and the Analog Communication Module 118a may be implemented in hardware and/or software to facilitate communication between components in the implantable device 110 as well as communication between the implantable device 110 and external devices. In some embodiments, the Communication Module 118b provides various communication pipelines towards the outer world. The Analog Communication Module 118a may include hardware components associated with establishing communication between components and/or devices. The Communication Modules 118a, 118b may be configured to maintain an encrypted low-energy wireless connection (e.g., Bluetooth, WiFi) with a device allowing interfacing with the user/patient (e.g., via a cell phone, smart-watch, etc.). The Communication Modules 118a, 118b may also communicate with one or more wearable devices acquiring environmental and/or biosignal data and provide a data connection to perform device performance monitoring and parameterization by an authorized clinician. The Communication modules 118a, 118b may also be configured to build up an encrypted high-speed data connection to fetch the acquired biometric and biosignal data from the memory 114 for transmission to the appropriate centralized data storage space in a deidentified format. The Communication modules 118a, 118b may also be configured for authentication of new data connections initiated either by the patient or the authorized clinician e.g., via Near Field Communication (NFC), and to provide a safe way for emergency interruption of the device operations e.g., via NFC.

Energy for operation of the implantable device 110 is provided by the battery 116. The battery 116 may be rechargeable if implanted. The Power Supply Module 131 may be coupled to the power supply 115 (e.g., a power supply unit 'PSU') or battery 116 and is responsible for stabilizing the power of the implantable device 110 and generating power lines with adequate stability. The power for the high intensity stimulation (>10 V) is also generated by the Power Supply Module 131. The battery 116, if rechargeable, is recharged by a Battery Charger Receiver Module ('BCRM') 133. Particularly if the battery is implanted, the BCRM may include a wireless charging receiver.

The system 100 may consist of the following additional hardware elements. In some embodiments, the power supply 115 may include a Battery Charger Transmitter Module ('BCTM') for providing wired or wireless charging to the implantable device 110 and the battery 116.

The system may further include an external Data Relay Device that may be used to relay the stored biometric, biosignal and device data, fetched through the Communication Module 118 of the implantable device 110, to a secured distal database (e.g., called Digital Biobank) and/or a server, in a deidentified and encrypted way. The uploaded cumulating patient-specific data of the database and/or server may be processed through automatized Backend Data Processing algorithms and software. In some embodiments, one or more processors external to the implantable device 110 (e.g., the processor(s) 132) may be configured to execute one or more modules for processing the uploaded data.

In some embodiments, one or more analog components or modules (e.g., the Analog Front-End and Data Acquisition module 117, the Analog Front-End Stimulation Module 119, the battery, the Power Supply Module, the Battery Charger Receiver Module, etc.) may be directly connected to the processor(s) 120. In some embodiments, one or more analog components or modules (e.g., analog radio of Wifi, analog radio of Bluetooth, etc.) may be connected to the Communication Module 118b of the processor(s) 120.

Placement of the electrodes 112 can be optimized for detection of specific neuronal activity patterns and/or for targeting a specified area. In some embodiments, the Modeling and Targeting Module 121 may be configured to analyze information related to patient specific geometry and anatomy of the head and determine a placement of the electrodes 112 based on the information. In case of an invasive placement, the electrodes 112 are implanted by using specific implantation tools and procedure.

In some embodiments, the processor(s) 132 may be configured to execute an Auto-Annotation Module 136. In some embodiments the Auto-Annotation Module 136 may be a semiautomatic process, in which the Auto-Annotation Module 136 may output labels to various segments of the acquired and stored data. These labels may then be checked and confirmed by trained personnel to generate ground truth labels. In some embodiments, the Auto-Annotation Module 136 may pre-label the recorded brain activity of epileptic seizures to ictal, interictal, and stereotypic artifact (e.g., chewing, walking, etc.) segments based on the characteristic patterns of the brain signals supported by the ancillary biosignal and environmental data (e.g., accelerometric signal, user input, heart rate, etc.) It should be appreciated that the Auto-annotation module 136 may be capable of reaching higher performance and more precise predictions compared to the embedded Detection module 123 of the implantable device 110, since the Auto-annotation module 136 is not constrained by computational capacity, and has the advantage of access to the whole duration of the recorded sessions for analysis, not only the current and past data points.

In some embodiments, A Performance-Metric Module 137 may compare the performance of the embedded Detection module 123 to the Ground Truth data to measure the actual patient-specific performance of the implantable stimulation system 110. The Performance-Metric Module 137 may also compare ideal predictions with the decision-making architecture of the embedded Detection Module 123, estimated by an iterative optimization of the real-time detector's parameter space in the Backend Data Processing environment. In some embodiments, this parameter optimization may be done in a dedicated Detection Model Training and Optimization Algorithm 138 using the patient specific (or cross-patient) stored data of the database and/or server and its Ground Truth Labels. In case of a high discrepancy in the actual and the ideal performance, or in case of a de novo parameterization, the Performance Metric Module 137 may recommend uploading an updated parameter-set to the Detection Module 123 in order to improve real-time performance. This parameter update, as well as the manual readout of the device parameters, service data, etc. may be done by an authorized trained clinician or technician using a dedicated Clinical User Interface Module 141. The Clinical Interface Module 141 allows access to the functions and data stored in the implantable device 110 in a user-friendly way, including setting up, modifying or reading out all patient specific settings; downloading recorded data; reading out device specific technical data and to perform device tests to confirm proper device functioning.

The System may optionally contain a Patient Interface Module 142, that may be configured to allow limited, read only access to some of the device information (e.g., battery status, memory status, event log), and may allow the user to turn the device in a "high-alert" mode for a limited amount of time. One practical use-case of this high alert mode is the use of the system 100 in epileptic patients with long prodromal syndromes, when the patients can predict in advance their imminent seizure. In this case the patient may increase the sensitivity of the system 100 at the expense of a temporary higher false alarm rate.

Figure 2:
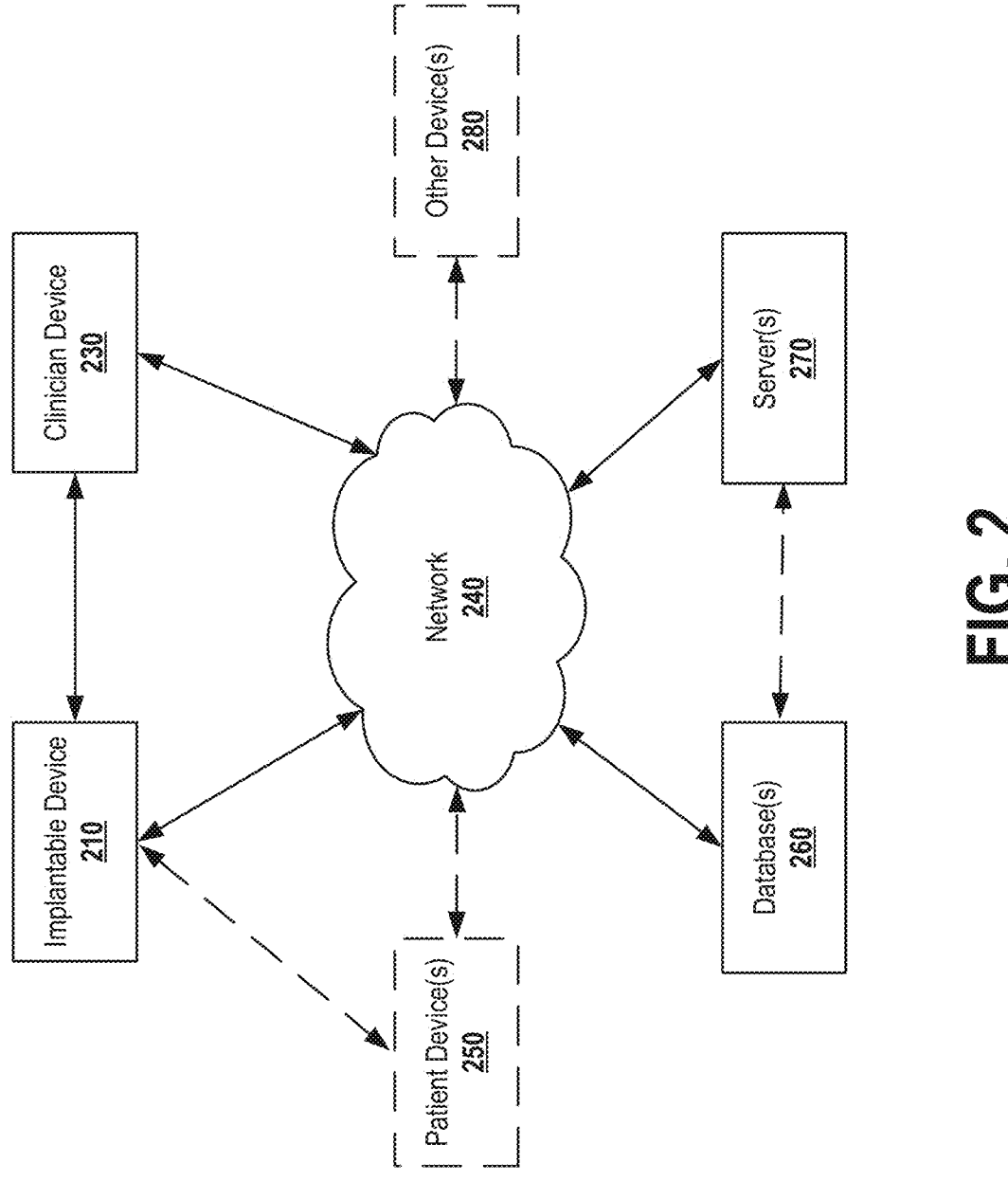
FIG. 2 is a schematic block diagram of a network through which the system interacts, according to an embodiment.

FIG. 2 depicts a network of devices for monitoring and modulating brain activity of the patient, according to an embodiment. As shown in FIG. 2, the implantable device 210 (e.g., similar to the implantable device 110) can be configured to communicate with other devices, such as a clinician device 230, one or more databases 260, one or more servers 270, and optionally one or more patient device(s) 250 and/or one or more other device(s) 280 (e.g., a researcher device, a backup device, etc.). The implantable device 210 can be configured to communicate with such devices via the network 240. The network 240 can include one or more network(s) that may be any type of network (e.g., a local area network (LAN), a wide area network (WAN), a virtual network, a telecommunications network) implemented as a wired network and/or wireless network and used to operatively couple to any device, including implantable device 210, patient device(s) 250, server 270, database 260, and/or other device(s) 280. In some embodiments, the implantable device 210 may be configured to communicate directly with the clinician device 230 and/or the patient device(s) (250) (e.g., via a communication interface or communication module embedded in the implantable device 210). In some embodiments, the Server(s) 270 may be configured to communicate directly with the Database(s) 260.

In some embodiments, the implantable device 210 can be configured to send data (e.g., biosignal data including brain activity data measured by the electrodes and/or additional sensor(s)) to the clinician device 230, patient device(s) 250, database(s) 260, server(s) 270, and/or one or other device(s) 280. In some embodiments, the implantable device 210 can include onboard processing (e.g., processor 120) to process sensor data (e.g., filter, convert, etc.) prior to sending the sensor data to the clinician device 230, the patient device(s) 250, database(s) 260, server(s) 270, and/or one or other device(s) 280. Alternatively or additionally, the implantable device 210 can be configured to send biosignal data (raw or processed) to the clinician device 230, the user device(s) 250, database(s) 260, server(s) 270, and/or one or other device(s) 280, for such devices to perform further processing and/or analysis of the data. In some embodiments, the implantable device 210 can include a communication interface (e.g., communication module 118) that is configured to allow one-way or two-way communication with an external device. The communication interface may be configured to transfer information between one or more processors and an external device such that the external device can train a model for detecting seizures (e.g., detect a precursor activity leading to a seizure, detect the onset of the seizure, or detect the presence of the seizure). In some embodiments, the model may be configured to be executed by the one or more processors of the implantable device 210.

The patient device(s) 250 can be any compute device(s) that are associated with a user to which the implantable device 210 is coupled. Examples of patient device(s) 250 can include a mobile phone (or other portable device, such as, for example, a tablet, a laptop, a personal computer, a smart device, etc.). In some embodiments, the patient device 250 may be configured to present (e.g., via a display) information relating to the functioning of system 100.

The server(s) 270 can include compute devices for running one or more processes and/or software for monitoring brain activity, detecting seizure activity, modulating brain activity, and/or training algorithms of seizure detection. Server(s) 270 can be in a location that is the same as or different from the implantable device 210 and/or clinician device 230. For example, server(s) 270 can be located in the same building as the clinician device 230 (e.g., a clinic, a hospital, a research center, etc.). Alternatively, server(s) 230 can be located at a remote location (e.g., such as with a cloud-based server).

The database(s) 260 can store information that can be accessible to implantable device 210, clinician device 230, patient device(s) 250, server(s) 270, and/or other device(s) 280. In some embodiments, a database 260 can be a hard drive, a database, a cloud storage, a network-attached storage device, or other data storage device. In some embodiments, database(s) 260 can store sensor data, historical patient data, data relating to other patients, etc. In some embodiments, the implantable device 210 and/or the clinician device 230 can send data to database(s) 260 and/or server(s) 270. The other device(s) 280 can be compute device(s) associated with other individuals or entities that have requested and/or been provided access to a user's data. For example, other healthcare professionals (e.g., specialists, physicians, nurses, researchers).

While not depicted in FIG. 2, it can be appreciated that the implantable device 210, the clinician device 230, the patient device(s) 250, the server(s) 270, the database(s) 260, and/or other device(s) 280 each can include components (e.g., a memory, a processor, a I/O device, etc.) that enable it to perform functions such as, for example, processing and/or analyzing the biosignal data, or using the biosignal to detect seizure activity in the patient.

FIG. 3 is a flow chart diagram of a method for detecting seizure activity and delivering electrical brain stimulation to inhibit the seizure activity, according to an embodiment. The method 300 can be performed by any of the systems described herein, including, for example, system 100. Method 300 includes measuring brain activity data associated with a brain of a patient using a plurality of electrodes implanted in the patient, at step 302. In some embodiments, method 300 may optionally include measuring additional biosignal data from one or more additional sensors, at 303. At 304, method 300 includes detecting a precursor activity leading to a seizure, an onset of the seizure, or a presence of the seizure based on the brain activity data. In some embodiments, the precursor activity leading to the seizure may be detected and stimulation may be applied to prevent the seizure from occurring. In some embodiments, the onset of the seizure may be detected, and stimulation may be applied to inhibit the seizure from progressing. In some embodiments, the presence of the seizure may be detected, and stimulation may be applied to terminate, reverse, or decrease the seizure activity. In some embodiments, detection of the onset of the seizure may occur when the detection output from the seizure detection model or algorithm (e.g., executed by the Detection Module) crosses an adaptive threshold. At 305, method 300 may include determining a timing with which to deliver electrical stimulation to the brain of the patient to disrupt oscillations in brain activity contributing to the seizure by analyzing oscillations in the brain activity. In response to detecting the precursor activity leading to a seizure, the onset of the seizure, or the presence of the seizure, causing delivery of electrical stimulation to the brain of the patient via at least a subset of electrodes from the plurality of electrodes according to the timing.

Figure 4:
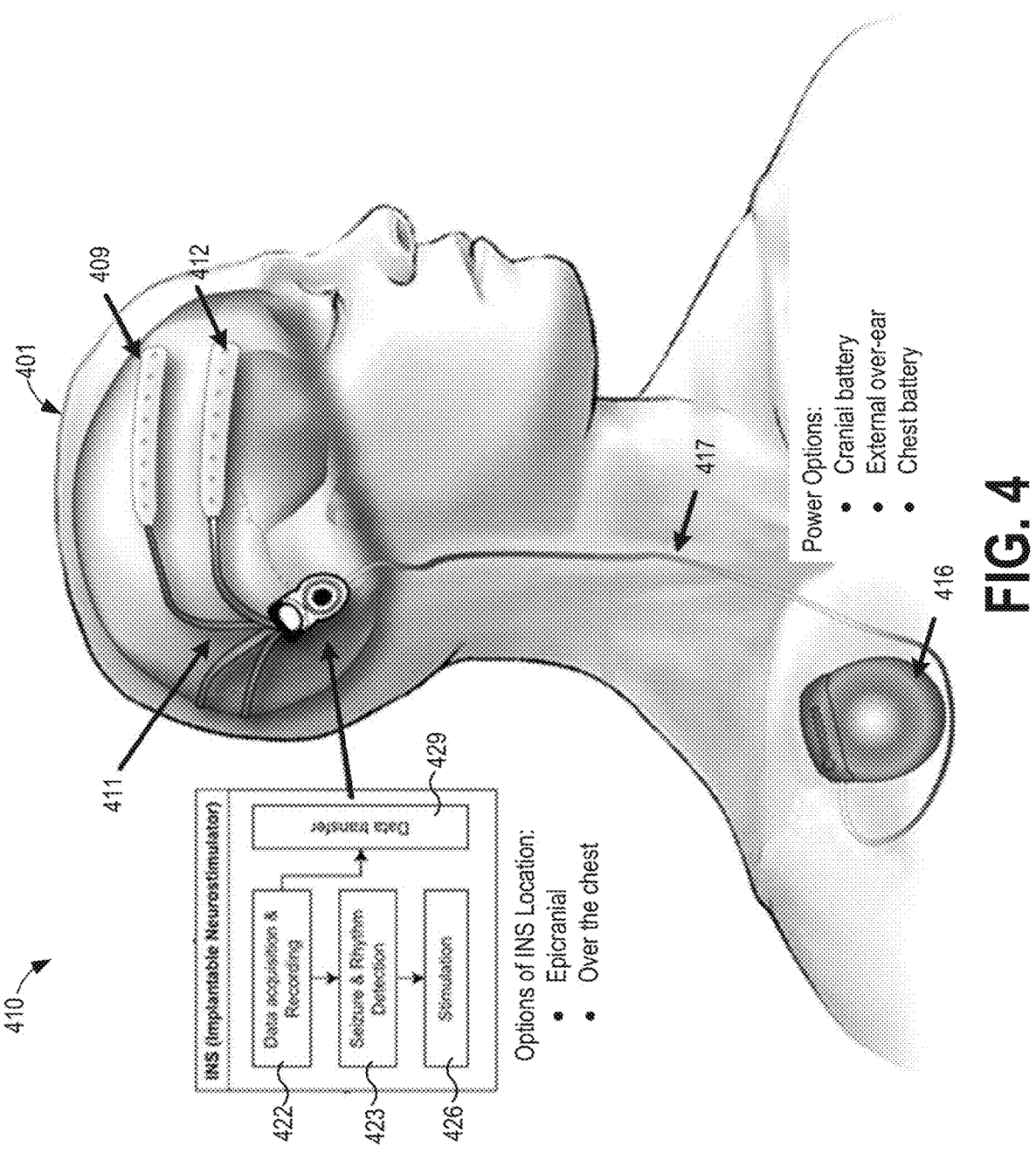
FIG. 4 illustrates an implantable device for monitoring brain activity to detect seizures and delivering electrical brain stimulation to inhibit the seizure, according to an embodiment.

FIG. 4 is an illustration of an implantable device 410 from monitoring and modulating brain activity of a patient 401, according to an embodiment. As shown, the implantable device 410 includes an implantable neurostimulator (INS) coupled to a plurality of electrodes 412 and a power supply 416. The INS is connected to a battery 415 via power cables 417 and provide power to the INS to perform the functions described. The battery may include a cranial battery, an external over-ear battery, or a chest battery. The implantable device 410 may be structurally and/or functionally similar to the implantable device 110, 210, therefore, certain details of the implantable device 410 are not described herein with respect to FIG. 4. The implantable device 410 includes electrodes 412 disposed on one or more electrode leads implanted in the subgaleal space. The electrodes 412 are connected to the INS via electrode cables 411. The INS is implanted in the head of the patient 401 (e.g., epicranially) or over the chest of the patient 401 (not shown) and is configured to perform any or all of the following functions: data acquisition and recording 422, seizure and rhythm detection 423, stimulation 236, and/or data transfer 429. For example, the INS may be configured to first record brain activity data at 422. The recorded brain activity may then either be analyzed onboard the INS to detect seizure activity and a rhythmicity in the brain activity at 423 or transferred to another device at 429. The INS may then generate a stimulation protocol at 426 based at least in part on the analysis of the brain activity data.

Figure 5:
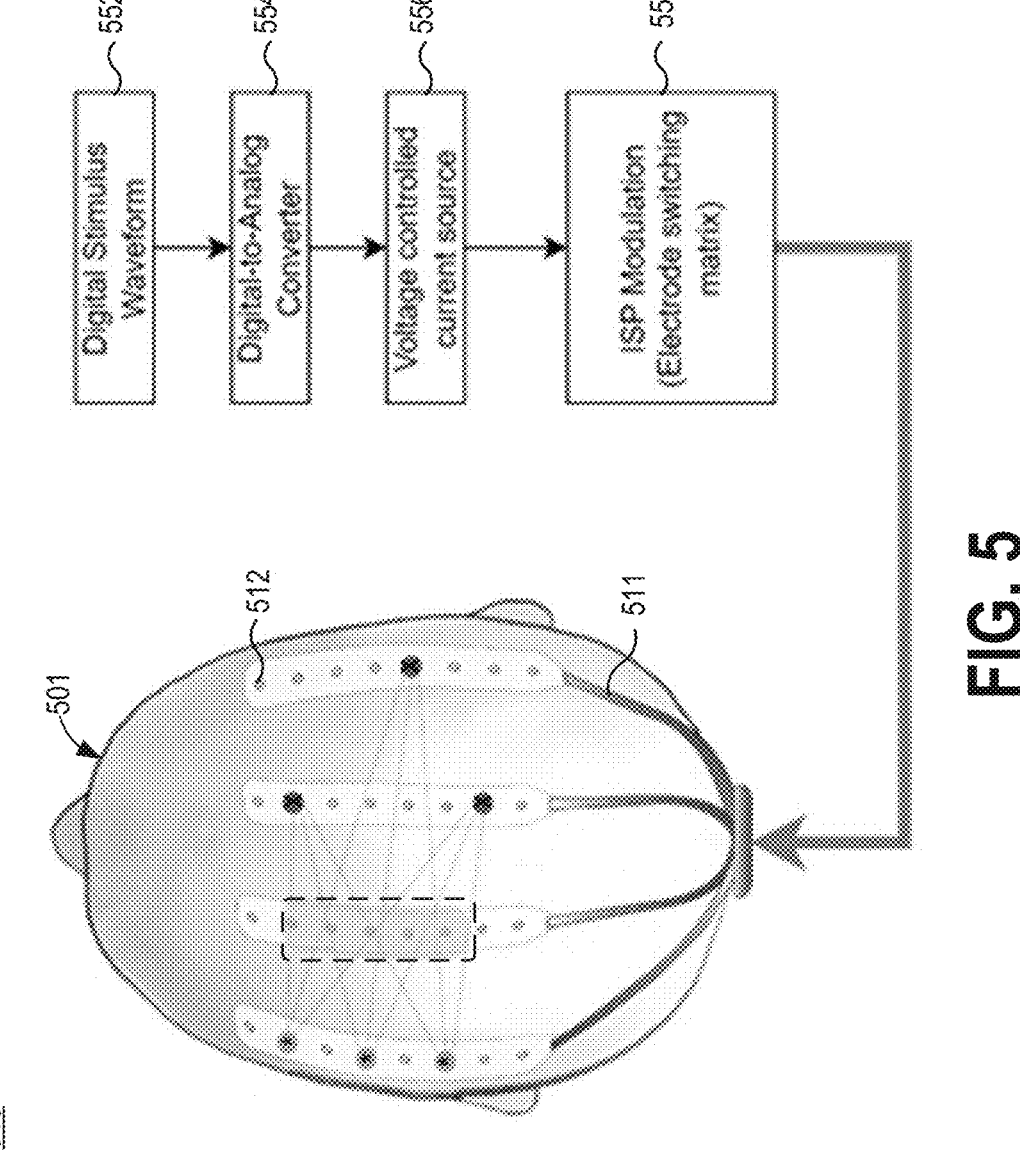
FIG. 5 shows a flow chart of an example method of stimulation generation and an illustration of activation of the electrodes of the implantable device of FIG. 4, according to an embodiment.

FIG. 5 shows a flow chart of example steps to generate stimulation and an illustration of the electrodes 512 relative to the head of the patient 501, according to an embodiment. As shown, the electrodes 512 are arranged on four electrode leads, with 8 electrodes 512 on each electrode lead. The electrode leads may be positioned in any suitable arrangement to record and/or stimulate the patient. In some embodiments, the electrode leads may be positioned such that each electrode lead extends in the dorso-ventral direction (e.g., such that a length of the electrode lead extends along a sagittal plane of the head). The electrodes leads may be distributed across a width of the head of the patient. The electrodes are electrically coupled to the processor(s) of the implantable device 510 (not shown) via the electrode cables 511. In order to deliver electrical stimulation via the electrodes 512, the implantable device 510 (e.g., the processor(s) included in the implantable device 510) may determine and generate a digital stimulus waveform, at 552. The digital stimulus waveform may be based on the brain activity measured by the electrodes 512. At 554, the digital stimulus waveform may then be moved through a digital-to-analog converter (ADC) to convert the signal to an analog signal. The implantable device 510 may include a current source configured to generate current corresponding to the analog signal, at 556. Alternatively or in addition, in some embodiments, the current source may include a voltage controlled current source, a current controlled current source, a pulse-width modulation (PWM) source (e.g., with subsequent capacitors), etc. At 558, the current generated by the voltage controlled current source may be passed through an electrode switching matrix (e.g., ISP Modulation component) to control allocation of the current through at least a subset of the electrodes 512, accordingly. For example, as shown, six of the electrodes 512 are connected to the stimulator such that three electrodes (marked with "X") are configured as cathodes, three electrodes (marked with asterisk "*") are configured as anodes, and the current is guided through the brain region indicated with a dashed box.

Figure 6:
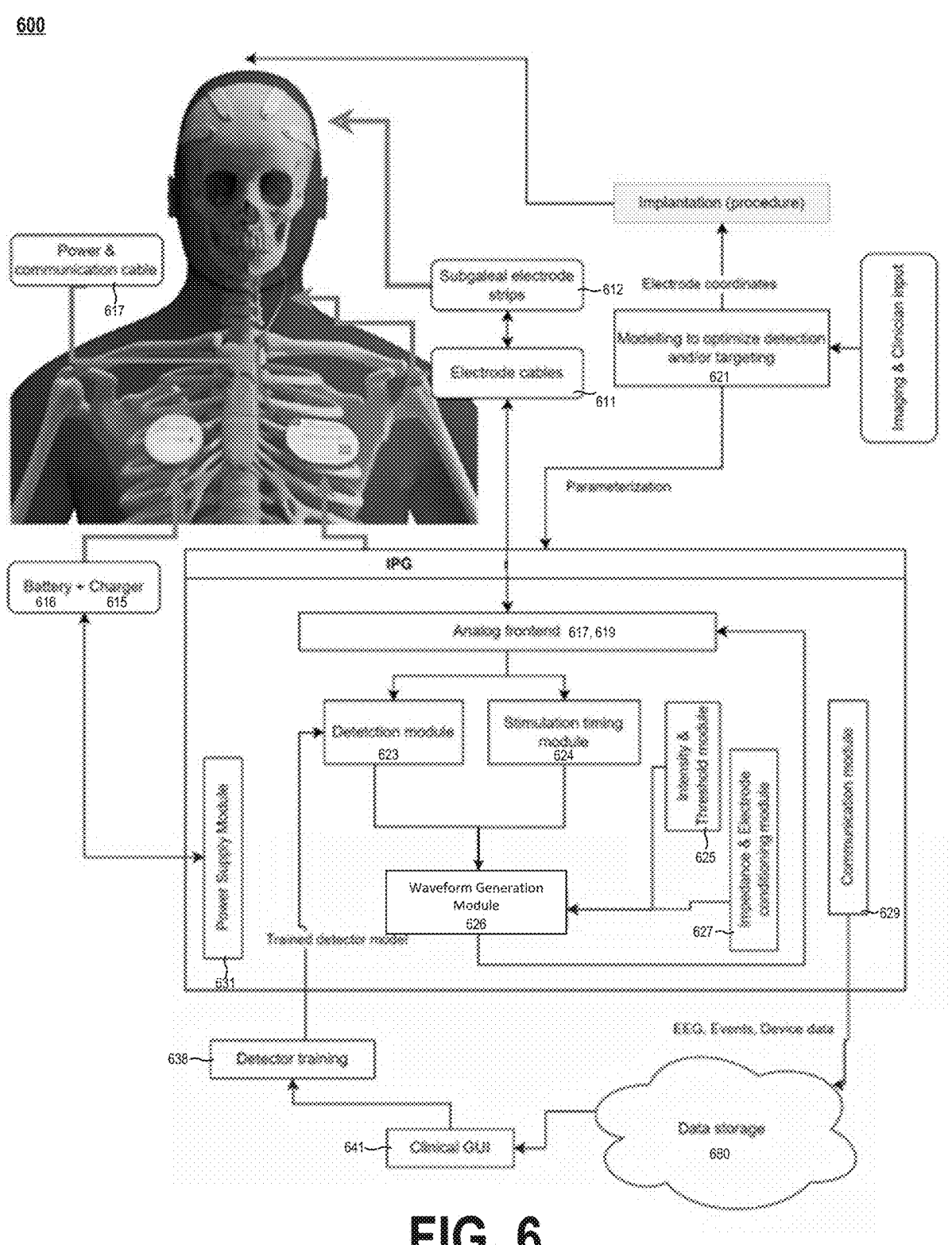
FIG. 6 is a schematic diagram of a system for monitoring brain activity to detect seizures and delivering electrical brain stimulation to inhibit the seizure, according to an embodiment.

FIG. 6 is a schematic diagram of a system 600 for monitoring brain activity to detect seizures and delivering electrical brain stimulation, according to an embodiment. In some embodiments, one or more electrode leads or strips 612 including a plurality of electrodes disposed thereon are configured to be implanted in the subgaleal space between the skull and the scalp and configured to measure brain activity of the patient. The electrode leads 612 are each connected to an implantable pulse generator (IPG) (similar to the INS) via electrode cables 611. While the IPG is shown as being implanted in a chest of the patient, it should be appreciated that the IPG may be implanted in any suitable location of the body in which the IPG can be connected to the electrodes. For example, the IPG may be implanted in a head of the patient (e.g., near a base of the skull). The IPG includes a processor configured to execute a plurality of functional modules. The brain activity signal first goes through the Analog Front End Module 622 where the analog signal is converted to a digital signal. In some embodiments, the digital signal representative of the brain activity at a given point is then sent through the Detection Module 623, where the digital signal is analyzed to detect a precursor activity to a seizure, an onset of the seizure, and/or a presence of the seizure. In some embodiments, the Detection Module 623 may be programmed to execute a trained detector model (e.g., the seizure detection algorithm), the settings of which are generated on an external device (e.g., the server, the clinician device, etc.). As shown, data is transferred from the server and/or database 680 onto the clinician device configured to run the clinician graphical user interface (GUI) 641 (e.g., via the display). In some embodiments, the clinician device (or any other suitable compute device) may be configured to train the detector model, the trained detector model may be configured to be saved on the memory of the IPG and executed by the Detection Module 623. In some embodiments, the Detection Module 623 may be pre-programmed. In some embodiments, the Detection Module 623 may be updated periodically (e.g., due to model improvements, new data, patient changes, etc.). In some embodiments, data from the IPG can be transmitted to the database and/or server 680 via the communication module 629. In some embodiments, the data transmitted from the IPG may be used to update the detector model.

In some embodiments, the digital signal may be simultaneously sent to the Stimulation Timing Module 624 where a pattern of the brain activity is analyzed to determine a timing with which to deliver electrical stimulation to disrupt at least on brain oscillation underlying the seizure. In some embodiments, the outputs of the Detection Module 623 and the Stimulation Timing Module 624 are sent to the Waveform Generation Module 626, where a digital stimulation waveform is generated. In some embodiments, the digital stimulation waveform is transmitted to the Analog Front End Module 622 and converted to an analog signal before being sent through the electrode cables, through the electrodes, and to the tissue of the patient.

In some embodiments, the IPG is coupled to a battery 616 and a charger 615. In some embodiments, the battery 616 may be implanted in the body of the patient. As shown, the battery 616 may be implanted in the chest of the patient and coupled to the IPG via power and communication cables 617. In some embodiments, the Power Supply Module 631 in the IPG is configured to receive power and/or signals from the battery.

In some embodiments, imaging data and/or other clinician inputs may be input into the Modeling and Targeting Module 621 during an implantation procedure of the device, and the Modeling and Targeting Module 621 may analyze a spatial geometry of the patient to inform placement of the electrodes. In some embodiments, the Modeling and Targeting Module 621 may output coordinates at which the electrodes 612 should be placed. In some embodiments, parameterization may occur in which data related to the placement of the electrodes 612 may be communicated to the IPG (e.g., a memory) to inform one or more modules executed by the processor of the IPG.

Figure 7:
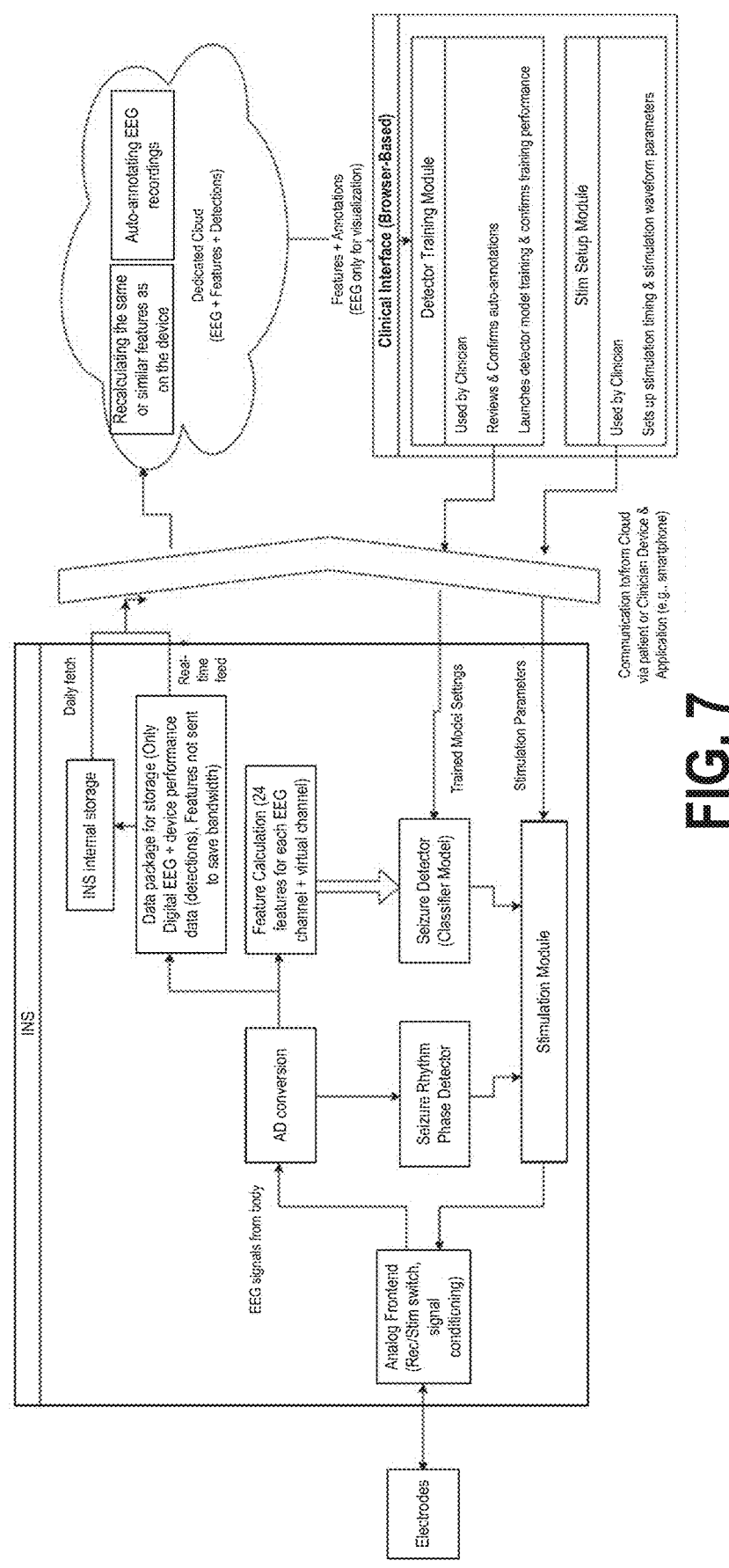
FIG. 7 is a schematic diagram of a brain activity feature calculation and detector teaching workflow of a system for monitoring brain activity and delivering brain stimulation, according to an embodiment.

FIG. 7 is a schematic diagram of a brain activity feature calculation and detector teaching workflow of a system for monitoring brain activity and delivering brain stimulation, according to an embodiment. Features (e.g., 24 features for each EEG channel and a virtual channel) are calculated on the implantable device for real-time or near real-time decision making, however for saving bandwidth in data streaming, only the digitalized raw EEG signal is transmitted to the server (e.g., cloud storage), where the exact same features are recalculated by server-side scripts (e.g., by processor(s) 132). These cloud-stored EEG sessions and their corresponding features are then annotated by an auto-annotation algorithm to depict putative ictal sections and artifacts. Auto-annotations are confirmed and validated by trained clinicians. The annotated cloud-stored sessions are used for training the detector model, which is then downloaded to the implantable device after its performance is confirmed by the clinicians. This cloud-based training can be repeated iteratively, as the cloud-stored patient-specific EEG database is growing, enabling gradually increasing detector performance.

Figure 8:
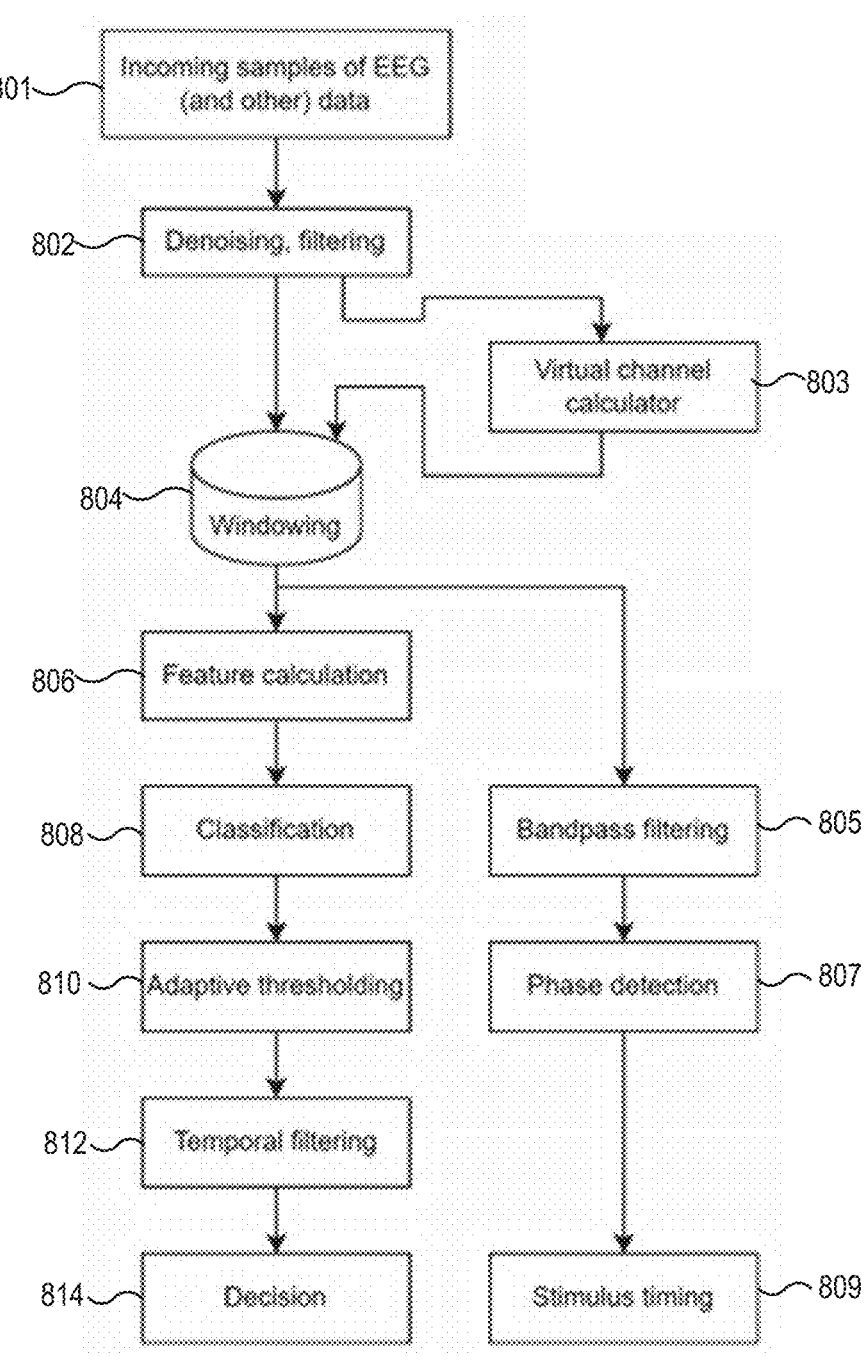
FIG. 8 shows a schematic diagram of a seizure detection stimulation-timing determination according to an embodiment.

3.1 Description of the Seizure Detection Algorithm:

FIG. 8 shows a schematic diagram of the seizure detection and stimulation pipeline, according to an embodiment. In some embodiments, epileptic seizures are detected using one or more learning algorithms (e.g., deep learning algorithm, regression algorithm, support vector machine, decision-making algorithm, random forest, etc.). In some embodiments, a regressive decision tree detection algorithm can be used for seizure detection. In some embodiments, the algorithm extracts one or more EEG features for each EEG channel within a sliding window. In some embodiments, the algorithm may extract one or more EEG features for each EEG channel and a derived virtual channel. In some embodiments, the algorithm extracts between 10 and 30 EEG features for each EEG channel and/or one or more derived virtual channels within a 1-second-long sliding window. In some embodiments, 24 EEG features are extracted. Then the data set is classified using a classification model built from regressive decision trees (i.e., the features can be input into the regressive decision tree). In some embodiments, the data set is a 24×33 dimensional data set. In some embodiments, the forest may be trained using patient-specific EEG data. In some cases, the forest may be trained and enriched using homologous prerecorded seizure samples to increase robustness. To generate a binary decision, the decision value is then thresholded using a dynamically changing adaptive threshold and with positive reinforcement from past decision experience. During recognized seizures, the stimulation timing is determined by a secondary phase-detection algorithm on a selected band passed EEG channel, with a preset refractory period and maximal stimulation number, to avoid over-stimulation. In some implementations, one or more aspects of the seizure detection and stimulation pipeline of FIG. 8 may be performed in combination with one or more other machine learning algorithms (e.g., artificial neural network based algorithm(s)), and the raw or band-pass filtered EEG channels, or their subset, and/or a virtual channel calculated from the former, can be fed/input directly into the model.

As shown in FIG. 8, samples of EEG (and additional data) are received by the processor of the implantable device at 801. The signals are denoised and filtered, at 802. In some embodiments, a bandpass filter is applied to the EEG signals. In addition to the original, band-pass filtered EEG channels (e.g., 1 to 256 EEG channels), the detection module may calculate one or more virtual channels as the weighted average of the real EEG channels in real-time (or real near-time), at 803. In some embodiments, signals may be collected from 30 EEG channels with the virtual channel being the 31$^{st}$ channel. The weights of the virtual channel may be calculated offline on already recorded EEG segments, by applying dimension reduction or source analysis techniques (e.g., principal component analysis (PCA) or independent component analysis (ICA)). The idea is to isolate seizure related activity in a single channel that is originally distributed/spread across multiple channels. Then, the signals of the 31 channels are windowed with a sliding window, at 804. In some embodiments, the sliding window can have a duration in a range of about 0.1 second and about 5 seconds, inclusive of all ranges and subranges therebetween. In some embodiments, the sliding window can have a duration about 1 second.

In some embodiments, after applying the sliding window, a filter (e.g., bandpass filter) is applied to the data sources used for the phase detection (e.g., EEG channel, virtual channel, other biosignal channel) to constrain the detection only to oscillations in a specific frequency band, at 805. At 807, phases of the signal are detected. At 809, a timing of applying each stimulus is determined based on the phase detection.

At a preset frequency (i.e., 'time-step'), various features are calculated for each of the windowed channels, at 806. In some embodiments, the preset frequency can be in a range between about 0.1 Hz and about 20000 Hz, inclusive of all ranges and subranges therebetween. In some embodiments, the preset frequency can be in a range between about 1 Hz and about 50 Hz, inclusive of all ranges and subranges therebetween. In some embodiments, the preset frequency is about 10 Hz. In some embodiments, a frequency of about 10 Hz is used with a sliding window of 1 second and can provide 90% overlap of the 1 second long sliding windows between each consecutive calculation.

The detection pipeline uses 1) time-domain, 2) frequency-domain, 3) spatial (across channel), and 4) temporal dynamic features of real EEG channels and derived signals to evaluate the acquired signals in real-time.

In some embodiment, any one of or all of the features for each channel may be calculated, including the virtual channel:

1. Root mean square (RMS)
2. Line Length (sum of differences) (LINE)
3. Variance (VAR)
4. Kurtosis (KURT)
5. Skewness (SKEW)
6. Hjorth Mobility (HMOB)
7. Hjorth Complexity (HCOM)
8. Wavelet (DB4)—level 2 (L2)
9. Wavelet (DB4)—level 3 (L3)
10. Wavelet (DB4)—level 4 (L4)
11. Wavelet (DB4)—level 5 (L5)
12. Wavelet (DB4)—level 6 (L6)
13. Relative Power (REL_POWER) of L2 (HIGH-GAMMA)—64 . . . 127 Hz
14. Relative Power (REL_POWER) of L3 (GAMMA)—32 . . . 63 Hz 15. Relative Power (REL_POWER) of L4 (BETA)—16 . . . 31 Hz
16. Relative Power (REL_POWER) of L5 (ALPHA)—8 . . . 15 Hz
17. Relative Power (REL_POWER) of L6 (THETA)—4 . . . 8 Hz
18. Mutual Information (MUTU)
19. Mean Coherence (COHER)
20. Standard deviation of mean Phase Delay (MPHD)
21. Recurrence Quantification Analysis—Recurrence rate (RQA_RR)
22. Recurrence Quantification Analysis—Determinism (RQA_DET)
23. Recurrence Quantification Analysis—Entropy (RQA_ENTR)
24. Recurrence Quantification Analysis—Averaged diagonal line length (RQA_L)

The calculated feature set contains both within (single) channel metrics calculated in the time domain and/or in the frequency domain, as well as across channel (multichannel) metrics. In order to save resources in the current embodiment, cross-channel metrics (i.e., the MUTU, COHER and MPHD) for each channel are stored as the average of all pairwise metrics in which the given reference channel is participating in (e.g., the MUTU feature of channel #1 is the average of the mutual information between channel 1 and every other channels.) The math for calculating each feature implements numerical approximations and simplifications in order to make them resource efficient that can be calculated on embedded systems (e.g., the processor of the implantable device) in real time or near real-time, (see Sections 5-9).

At 808, the features of each time-step are classified (e.g., by a classification algorithm). In some embodiments, the features can be classified using a Random Forest and/or XGBoost method for classification. The nodes and branches of the decision trees can be stored in a proprietary format, that allows the quick evaluation of each tree in a computationally efficient manner, while keeping memory footprint low.

Output of the decision trees are averaged, and decision is made by thresholding of this average value, at 810. In some embodiments, adaptive thresholding is used in which the thresholding of the average (e.g., the 'consensus vote') of the decision trees is compared to a dynamic threshold. Additionally or alternatively, an output of the classification model may be compared to a static threshold. An adaptive threshold may be used because consecutive decisions of the classifier may not be independent from each other. For example, within a seizure, there is a higher likelihood of the classifier outputting a 'seizure' sample following a previous EEG sample already classified as 'seizure', while interictally it is the opposite: the likelihood of a non-seizure EEG sample following a non-seizure sample is higher. By other words, since a state change of the neuronal network is less common than not, there is a bias of the classifier toward keeping the previous state from sample-to-sample. This a priori knowledge is incorporated in the dynamic thresholding, where an actual threshold value is determined based on the previous decisions and classification, providing a sense of history and memory to the detection system (see section 10—"Adaptive Thresholding of Decision in Real-Time Seizure Detection"). Stated another way, and by way of example only, a "no seizure" decision may persist unless/until a sufficient number of subsequent classifications indicate that a "seizure" decision is warranted.

In some embodiments, the detection threshold may move between two extremes such that that every frame that is classified negative (i.e., non-seizure) increases the threshold value step-by-step until a ceiling value is reached; while every frame that is classified as positive (i.e., seizure) decreases the threshold until a floor value is reached. The increment and the decrement may be either constant or may follow any arbitrary dynamics (e.g., a second or a third identical classification causes larger steps than the first one, etc.). The floor and the ceiling may be optimized in an iterative process to maximize detector performance in terms of true negative and true positive detections versus false negatives and false positives. Resultingly, frames consecutively being classified as seizure around the onset of a seizure decreases the detection threshold and ensures that most frames of the seizure may be correctly classified, despite minor qualitative fluctuation of the seizure characteristics, that would otherwise result in a few mis-classified frames and fragmented detection. Once the seizure is over and a number of frames are classified non-seizure despite the low threshold, the threshold gradually increases to ceiling, ensuring that the random non-seizure related fluctuations of the classification output do not result in sporadic false positive detections. Lastly, the detector protocol also accounts for the temporal dynamics of the changes in the signal.

In some embodiments, the model may determine a range of effective prediction probability threshold values, and a threshold value may be selected from the range of effective prediction probability threshold values. In some embodiments, the range may be based on at least one of a desired level of specificity, a desired level of sensitivity, or a desired level of one or more event-related metrics. In some embodiments, the output of the model may be compared to the threshold value selected, and in response to determining that the output crosses (e.g., exceeds) the threshold value, a timing and/or subset of electrodes with which to deliver electrical pulses may be determined. Delivery of the electrical pulses to the brain of the patient via at least the subset of electrodes may be caused, according to the timing.

In some embodiments, the model may determine a range of effective prediction probability threshold values based on balancing between performance metrics from at least one pair of performance metrics, each pair of performance metrics from the at least one pair of performance metrics having the property that improving one performance metric from that pair of performance metrics results in a diminishing or degradation of the other. For example, the range of effective prediction probability threshold values can be determined based on balancing between at least one pair of performance metrics that exhibit an inverse or trade-off relationship, such as sensitivity and specificity, or one or more event-related metrics.

In some embodiments, temporal filtering of the thresholded decisions can be completed, at 812. For example, median filtering of the consecutive thresholded decisions can be used to eliminate the false positive alarms in case of sporadic positive decisions. By incorporating a kernel (e.g., tail heavy kernel) in this temporal filtering, this step can help detect preset temporal dynamics of the change in seizure-likelihood. Similarly, other embodiments may incorporate a short-term temporal "memory" for the calculated features themselves, and realize the detection of the temporal dynamics at the level of the classification. Embodying the detection of temporal dynamics post-classification only uses minimal computational resource, while still providing the required efficacy.

The training of the classification algorithm can be performed on a pre-labelled training dataset using either bootstrap aggregation (bagging), gradient boosting, or a similar method. In some embodiments, the training dataset consists of ictal and non-ictal EEG segments from at least one of the actual patients (i.e., patient specific training) or from other patients (i.e., cross-patient training). For cross patient training, the EEG segments from various patients are normalized/equalized to eliminate variance originating from factors other than the brain activity (e.g., different recording devices, different signal-to-noise ratio, etc.). To improve robustness of patient-specific training, the seizure samples of a given patient may be enriched with seizures originating from patient with similar feature-landmark profiles (e.g., 'digital seizure-siblings'), (see section 12—"Enriching Training Dataset with Xeno-Seizures to Improve Model Training").

The training set can be prepared such that the EEG signal is windowed (e.g., the same as or in a similar way as it is processed real-time or near real-time by the implantable device mentioned above), and the same or a similar set of features are calculated for all windows and channels as in the real-time or near real-time detection protocol. In some applications the windowed features calculated in real-time or near real-time during the data acquisition are stored along with the EEG data and are already available at the time of annotation.

Annotation of the dataset may be done either manually or assisted by automated offline seizure detectors by labeling every windowed feature-sets as seizure or non-seizure. Some stereotypic activity of the patients can result in EEG artifacts similar to seizure activity, and may therefore lead to false positive detections. Thus, samples of such artifacts are forcedly included in the training datasets as non-seizure samples. To this end, the data acquisition is appended with the dedicated recording of a set of typical artifacts (e.g., chewing, walking, clapping, etc.), and the annotation labels are also appended with a dedicated category for each artifact. The training algorithm may be designed to include samples from each type of artifact such that that all (or at least some) of the artifacts are represented in the non-seizure sample set along with the typical interictal brain activity patterns (see section 11—"Forced Artifact-Inclusion in Machine Learning").

The specificity of the training may be optimized by including (or training based on) only the initial periods of each seizure, which are the focus of the interest of the detection. The EEG pattern during the course of the seizures may change significantly, and including the whole seizure activity may increase the overlap of seizure patterns with non-seizure patterns, and therefore result in lower overall detector performance.

Known performance metrics evaluate the detection accuracy sample-by-sample (i.e., window-by-window), which in combination with the bias originating from the unbalanced underrepresentation of seizure samples versus non-seizure samples in the recorded datasets, do not realistically describe detector performance. Optimizing the detectors for such a window-based (i.e., sample-based) performance can be counterproductive. Seizure samples are not randomly distributed among non-seizure samples, but are grouped into intervals, and the goal of the model is to detect the beginning of these intervals. For example, missing the detection of a few samples within a seizure degrades sample-based performance metrics even though the seizure may be properly detected. Thus, methods described herein may train and determine a detection threshold using a compound metric focusing on the performance of seizure detection rather than a window-by-window based performance metric.

3.2 "Dual-Approach Detector"

In some embodiments, a dual-approach detector algorithm may be used for detecting a seizure from the EEG signals measured. In some embodiments, the first type of detector algorithm (e.g., cold start) includes a detector that receives a universal single channel signal, the detector being trained on 1-2 patient-specific seizures (e.g., the patient in which the implantable device is coupled) and data from other patients. In some embodiments, the second type of detector algorithm includes the patient-specific algorithm as described above with respect to FIG. 8, with growing database. In some embodiments, the decision is made by a manually set weighted average of the two detector algorithms that can be gradually shifted from the first to the second as more data is acquired. In some embodiments, a metamodel is built to do the final decision. The metamodel can also take into account the past outputs of the initial models by buffering them.

The detection performance of the detector module had been compared to other state-of-the-art seizure detection algorithms, as shown in FIG. 9. The performance of the algorithm has been tested on an open-source seizure dataset released by the Temple University Hospital (TUH EEG corpus). Specifically, comparison of the performance of the proposed detection algorithm with the math optimization and adaptive thresholding as described, estimated on the Temple University Hospital dataset, to other seizure detection algorithm performances reported in the literature. The current algorithm is superior or comparable to other available methods reported in the literature both in terms of sensitivity and specificity. In some embodiments, the algorithm is implemented on an embedded system, where computations are shared between a field-programmable gate array (FPGA) chip and a microcontroller to optimize for real-time operations.

Figure 10:
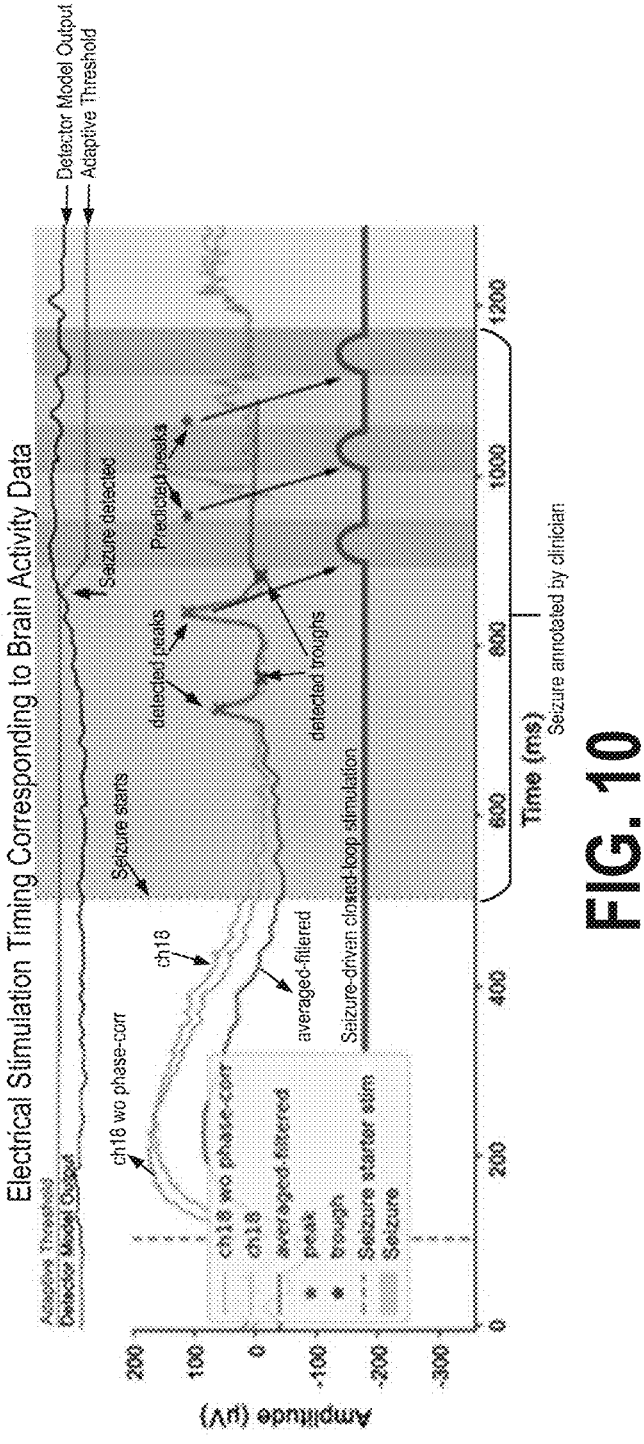
FIG. 10 shows example data of closed-loop, phase-aligned ictal stimulation delivery in a rat model.

FIG. 10 shows example data of closed-loop, phase-aligned ictal stimulation delivery. As shown, an induced seizure in a rat model of epilepsy is triggered at the vertical dashed line labeled "seizure starts". The start of the seizure is confirmed by clinicians and the seizure activity occurs within the bracket labeled "seizure annotated by clinician". The device detected the seizure approximately 2 seconds later marked by an upward arrow and a label. Note the elevating decision model output crossing the threshold at the detection point, triggering the lowering of the adaptive threshold level. Peaks and throughs of seizure oscillation are detected real-time by the device and marked by 'x'-es on the figure and labeled. Extrapolated future peaks are marked by asterixis and labeled based on applying the measured average interpeak distances. The detected and predicted peaks trigger stimulus delivery (denoted with a thick line at the bottom of the figure and labeled "Seizure-driven closed-loop stimulation") with a preset angular delay to precisely target a desired phase of the seizure rhythms.

4. Performance Evaluation

Performance of the detector algorithm using the feature calculation methods described herein was evaluated on the Children's Hospital Boston-Massachusetts Institute of Technology (CHB-MIT) Scalp EEG database, an epilepsy dataset commonly used for developing and comparing seizure detection algorithms. From the 24 patients of the CHB-MIT dataset, 9 contained less than 5 seizures in total and therefore they were excluded from the analysis. Another 5 patients were additionally discarded due to young age (between ages 1.5 and 5) because younger aged patients expressed largely different background/baseline activity and/or due to massively artifact contaminated seizure EEG compared to the rest of the subjects.

Two decision-tree based, patient-specific seizure detector models were used for evaluation (Random-Forest and XGBoost). A separate model has been trained for each patient, and the performance was evaluated only on EEG data from the same patient. Investigating the cross-patient performance of these detectors was out of the scope of this evaluation.

The following event-based, clinically relevant metrics were utilized for quantifying and evaluating detection performance. Event-Onset Detection Rate, which represents the percentage of seizures that are detected at their onset (i.e., the seizure is correctly detected, and the detection intersects with the first 5 seconds of the seizure). Event Detection Rate, which represents the ratio of seizures that are detected at any time during their duration (i.e., detection is accepted even if it is triggered in the last seconds of the seizure). False Alarm Rate, which represents the number of false detection segments from the joint prediction intervals per hour. False alarms within less than 2 seconds of temporal separation were merged together. False Alarm Duration Rate, which represents the duration of false alarm segments measured in seconds per hour. Average False Alarm Duration, which represents average length of false alarms in seconds. Average Detection Delay, which represents a mean detection delay of all detected seizures. Negative delays (early detections) are substituted with zeros. This flooring of values had negligible effect on the statistics since none of the models produced more than two detections with negative delay in total. Incorrectly detected seizures are dropped. Event Detection Quality (EDQ), which represents a mean of the detection qualities for all detected seizures. The larger the delay of the detection, the smaller the EDQ score is. The quality score follows an exponential decay with respect to the lengths of the detection delay, starting from 1 if the detection happens in the first 5 seconds of the seizure and reaching 0 at the end of the seizure.

To ensure that the feature sets are characteristic to the electrical/physiological artifacts and that the late parts of the evolving seizures do not bias the detector, a dedicated training annotation set was used to train the detector algorithm. The detector's performance was optimized based on two metrics: (i) avoiding false detections of artifacts that co-occurred with seizures and (ii) decreasing delays due to the detection bias of the later parts of seizures. Similarly, in clinical use, the detector may be trained only by the initial segments of the ictal activity.

Results

TABLE 1

|  | RandomForest | XGBoost |
|---|---|---|
| Event Detection Quality | 0.951 | 0.955 |
| Event Detection Rate | 0.944 | 0.944 |
| Average Delay [s] | 4.078 | 3.186 |
| False Alarm Rate [1/day] | 5.607 | 0.903 |
| Average False Alarm Duration [s] | 1.136 | 0.552 |
| Event Onset Detection Rate | 0.675 | 0.860 |
| False Alarm Duration Rate [s/h] | 0.265 | 0.021 |

Table 1 shows a summary of the performance metrics across the two models tested. As shown, both models perform similarly in event detection quality and event detection rate. The XGBoost algorithm has an average delay that is about 1.1 seconds less than RandomForest. The XGBoost algorithm shows a lower average false alarm duration and a lower false alarm duration rate.

5. Method 1A—Simplifying the Calculation of Mutual Information in Real-Time Seizure Detectors 5.1 State of the Art Mutual information (MI) quantifies the amount of information obtained about one random variable through observing another random variable. It's commonly used in information theory to measure the dependence between two variables. In EEG processing, MI can be used to determine the amount of shared information between different EEG channels. EEG signals during a seizure exhibit distinct patterns compared to normal brain activity. The mutual information between channels can change dramatically during a seizure. Calculating MI between EEG channels can help in identifying these patterns and can be used as a feature for seizure detection algorithms.

Traditional methods for computing MI are computationally expensive and not suitable for real-time applications. Recent advances have proposed approximate methods and algorithms that are more computationally efficient, allowing for real-time computation. Some employ histograms, kernel density estimation, or k-nearest neighbors. For real-time applications, the method should be computationally efficient. This is especially important for wearable and/or implantable EEG devices with limited computational resources.

The continuous nature of EEG signals means they often require a significant computational cost when computing MI. To manage this, these signals are converted into a more manageable, discrete format. This quantization can either be uniform, where each level has an equal range, or non-uniform, where levels might vary based on the data distribution.

Following discretization, probabilities are estimated using histograms or kernel density methods. In real-time applications, histograms are typically the method of choice due to their inherent computational efficiency. Mutual information is then computed as:

$$MI(X,Y) = \Sigma x \in X \Sigma yy \in Y\, p x, y) \log(p(x)p(y)p(x,y))$$

where, p(x,y) represents the joint probability, while p(x) and p(y) are the marginal probabilities.

Several approximate methods have been devised for a more efficient calculation on time series of discrete value:

1. Binning: One of the simplest approximation methods involves grouping continuous values into bins and estimating probabilities based on these bins.

2. k-Nearest Neighbors (k-NN): This method approximates MI by considering the distance to the k-th nearest neighbor in the joint space. It provides a balance between accuracy and computational complexity.

5.2 Problem Definition

Directly applying the joint probability-based formula of MI is computationally intensive and has a large memory footprint to store the joint probability matrices. Also, to avoid the numerical imprecisions (i.e., under-sampling) of word probabilities with sparse representation, a frequent problem in EEG datasets, usually very long EEG segments are required.

5.3 Description of Proposed Solution

The proposed alternative approach for measuring Mutual Information between EEG channels computes the covariances between channels and then transforms these through a logarithmic function. Theoretically, if the data is assumed to be Gaussian or near-Gaussian, the MI can be approximated using the covariances of the variables. In the context of EEG processing, the Gaussian assumption may simplify Mutual Information calculation because, under this assumption, Mutual Information between two Gaussian variables can be directly computed from their covariances.

While, in real-world EEG data, the Gaussian assumption might not always hold statistically, it is proposed that despite the mathematical imperfection, the Gaussian approximation can still provide an acceptable approximation of MI between two EEG channels. This may provide both computational efficiency and smaller memory footprint.

Gel'f and & Yaglom in 1957 highlighted that when the combined distribution of a first variable (X) and a second variable (Y) follows a bivariate normal distribution (ensuring that both X and Y have normal distributions individually), there's a precise connection between the Mutual Information I and the correlation coefficient ρ:

$$I = -\frac{1}{2}\log\left(1 - \rho^2\right)$$

The equation above can be derived as follows for a bivanate Gaussian:

$$\begin{pmatrix} X_1 \\ X_2 \end{pmatrix} \sim \mathcal{N}\left(\begin{pmatrix} \mu_1 \\ \mu_2 \end{pmatrix}, \sum\right), \quad \sum = \begin{pmatrix} \sigma_1^2 & \rho\sigma_1\sigma_2 \\ \rho\sigma_1\sigma_2 & \sigma_2^2 \end{pmatrix}$$

$$H(X_i) = \frac{1}{2}\log\left(2\pi e \sigma_i^2\right) = \frac{1}{2} + \frac{1}{2}\log(2\pi) + \log(\sigma_i), \; i \in \{1, 2\}$$

$$H(X_1, X_2) = \frac{1}{2}\log\left[(2\pi e)^2 |\sum|\right] = 1 + \log(2\pi) + \log(\sigma_1\sigma_2) + \frac{1}{2}\left(1 - \rho^2\right)$$

Therefore, $$I(X_1; X_2) = H(X_1) + H(X_2) - H(X_1, X_2) = -\frac{1}{2}\log\left(1 - \rho^2\right)$$

Information regarding this equation is described by Gel'f and I. M.; Yaglom, A. M. (1957). "Calculation of amount of information about a random function contained in another such function". American Mathematical Society Translations, (hereinafter, "Gelfand & Yaglom"), the disclosure of which is incorporated by reference in its entirety.

The detrended windowed EEG data to be compared approximates well the normal distribution, thus the simplification above provides an acceptable estimate of the mutual information.

In essence, the proposed method operates as follows. For two EEG channels, A and B, the method first computes the covariance between them. This is done by multiplying the deviation of each sample from the mean for both channels and summing the results. The square of this covariance is then normalized by the product of the variances of the two channels, resulting in a value denoted as $r_{sq}$. This value represents the squared correlation coefficient between channels A and B. Finally, the logarithm of the quantity $1-r_{sq}$ is computed, approximating the mutual information between the two signals. The process is repeated for all possible pairs of channels, excluding the comparison of a channel with itself. The final MUTU feature value for EEG channel A is the cumulative sum of these logarithmic values, representing the sum of all pairwise log values between EEG channel A and every other EEG channel. Example operation pseudocode is provided below:

```
function fx_MUTU:
MUTU is the sum of co-variances for every channel pair.
function co-variance for 1 channel pair A and B:
input: time_function_A, time_function_B, var_A, var_B, mean_A, mean_B
output: cov_A
cov_A = 0;
for each channel B{
   if ( A != B ) {
      cov1p = 0;
      diff_A = diff between sample_A and mean_A
      for all 512 samples {
         diff_B = diff between sample_B and mean_B
         cov1p = diff_A * diff_B;
      }
      r_sq = cov1p^2 / (var_A * var_B);
      cov_A += log(1 − r_sq);
   }
}
```

Known Mutual Information is computed using probabilities and entropy calculations, which can be computationally intensive. The Gaussian approximation offers a significant reduction in computational complexity compared to non-parametric methods, making it a simplified and efficient alternative to the traditional MI measure. Building on the near-gaussian distribution of input data, the proposed approach simplifies this by focusing on covariances between EEG channels, providing a straightforward and computationally efficient way to gauge their dependence. Another advantage is the reduced memory footprint, as there's no need to estimate and store detailed probability distributions or large histograms and avoids the drawbacks of binning the data needed because of the very sparse representation of discrete values in the datasets. This is particularly beneficial in real-time embedded systems, where computational efficiency is paramount.

5.4 Demonstration of Embodiment

Figure 11A:
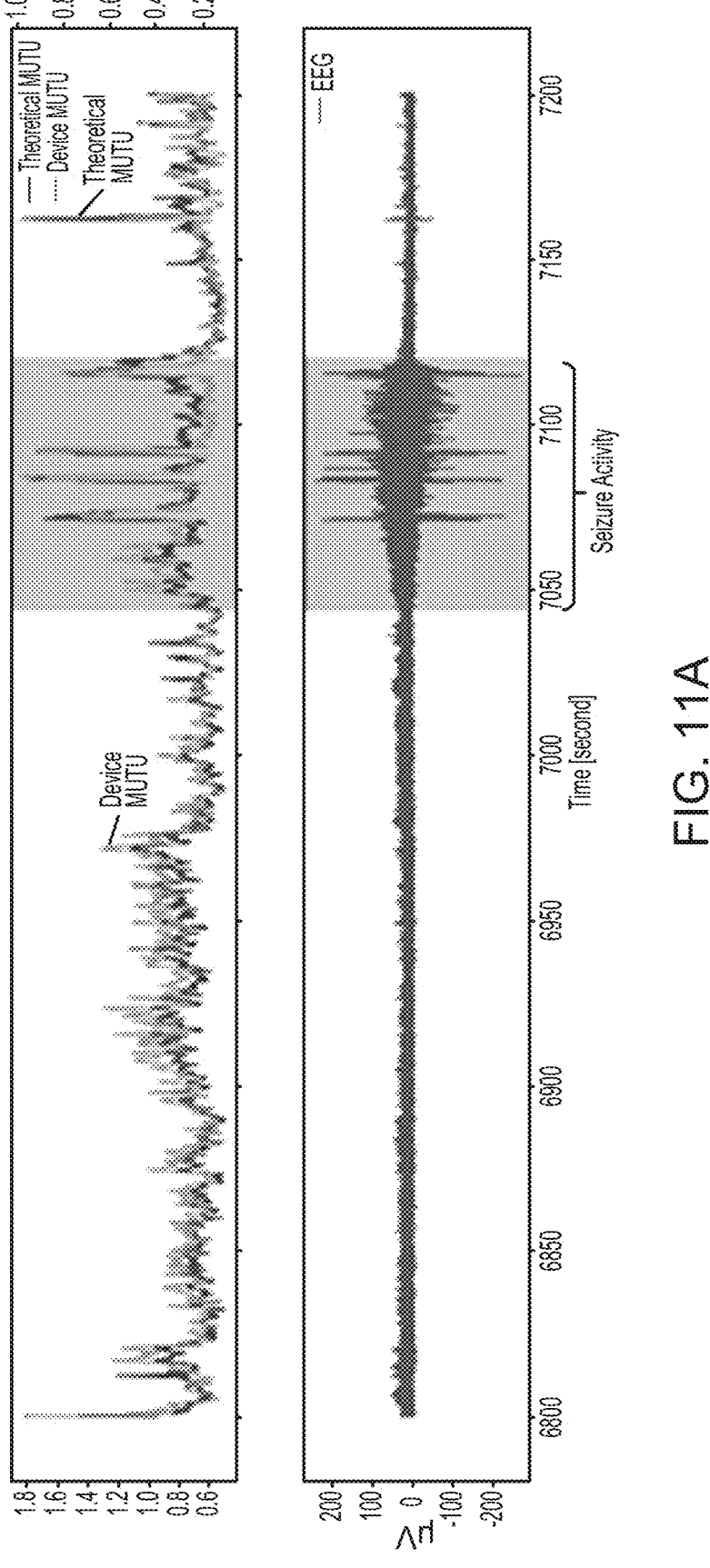
FIG. 11A shows a comparison of Mutual Information Values calculated from an EEG signal using two different techniques.

FIG. 11A shows a comparison of Mutual Information Values calculated using the known approach versus the proposed approach between an EEG channel shown on the bottom panel against other EEG channels (not shown). The EEG channel signal shown on the bottom panel contains both interictal and ictal activity (indicated by the bracket). The top panel shows the Mutual Information of the EEG channel calculated by the known approach (labeled "Theoretical MUTU") and the proposed novel method (labeled "Device MUTU").

Figure 11B:
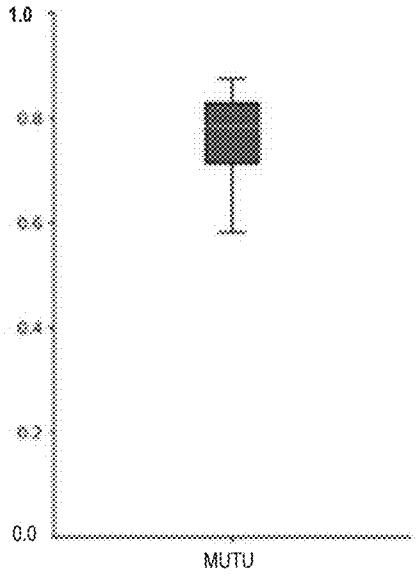
FIG. 11B shows a boxplot of correlation coefficients between Mutual Information Values calculated using the different techniques.

The similarity of simplified features and their known mathematical definition are further demonstrated in FIG. 11B and Table 2. FIG. 11B shows a boxplot comparing the correlation coefficients obtained from 32 EEG channels using the known implementation of the Mutual Information algorithm versus the proposed approach.

TABLE 2

| Description | Known vs. proposed approach |
| --- | --- |
| Average Correlation Across 32 EEG Channels | 0.74 |
| Median Correlation Across 32 EEG Channels | 0.784 |
| Standard Deviation of Correlation Across 32 EEG Channels | 0.137 |

Table 2 shows the comparative analysis of correlation metrics between the known and the proposed Mutual Information calculation method across 32 EEG channels. As shown in both FIG. 11B and Table 2, there is a high correlation between the known approach and the proposed approach, demonstrating that the proposed approach may be a computationally efficient alternative that can be used for real time or near real-time applications.

To see the proposed approach in operation and the effect of using the proposed approach on detection model performance, see section 9—"Demonstration of Embodiment of the Simplified Features"

5.5 Resource Economics

Known methods for calculating mutual information (MI) between EEG channels rely on the estimation of joint and marginal probabilities, often necessitating large 2D histograms. For example, considering one channel X against all other channels Y, joint probabilities p(x,y) are estimated over a sliding window of 512 samples, with symbol counts ranging up to 64 k. For example, the following equation may be used:

$$MI(X,Y) = \Sigma p(x,y) * \log(p(x)p(y)p(x,y))$$

for selected channel X, where p(x,y) represents the joint probability, while p(x) and p(y) are the marginal probabilities.

This approach demands a 2D histogram of size 512×512 to represent active combinations, coupled with an administrative matrix of the same dimensions to track active elements. Therefore, with known approaches, the memory requirements include histogram storage (512×512 entries, each 9 bits wide (log 2(512)) as well as an administrative matrix including 512×512 entries, each 32 bits wide (to store 16-bit identifiers for symbols in two dimensions). Known approaches use an administrative matrix with either content-addressable RAM or exhaustive iteration through 512×512 entries for updates, leading to a worst-case time complexity of 512 k clock cycles per channel pair.

The proposed approach leverages covariance-based approximations under Gaussian assumptions, significantly reducing computational and memory overhead. For example, for each channel X, mutual information can be derived by iteratively calculating: (i) Variance (varX) as the sum of squared deviations for the samples (e.g., 512 samples); (ii) Cross-product accumulations (cov1p) between deviations of channel X and each Y; (iii) Squared correlation coefficient ($r_{sq}$) using cov1p2/(varX·varY); (iv) Logarithmic transformation of ($1-r_{sq}$), summed across all pairs involving X (e.g., 32 pairs). Example operation pseudocode for calculating mutual information is provided below:

```
Note: 'diff' represents the distance between the sample and the mean value.
var_X = accumulate (diff_X ^2) for 512 samples;
mutu_X = 0;
for each channel Y{
   if ( X != Y ) {
var_Y = accumulate (diff_Y ^2)   for 512 samples;
cov1p = accumulate (diff_X * diff_Y) for 512 samples;
r_sq = cov1p^2 / (var_X * var_Y);
mutu_X += log(1 – r_sq);     use log lookup table
   }
}
```

To implement, mean and variance calculations can be completed for 33 channels, covariance computations can be completed for 32 channel pairs, and total accumulation can be performed for each channel. The proposed approach may enable resource saving. For example, for memory, a constant storage for a logarithmic lookup table and optional storage for 33×32 covariance values can be used, which is about 33 kbits. For computation, only 16 k cycles per channel X can be completed versus 512 k in the known method.

The proposed solution reduces memory requirements by up to 87% and computational time by 98%, enabling real-time implementation on embedded systems with limited resources. This efficiency ensures the feasibility of the method in portable seizure detection devices, demonstrating superior scalability and practicality over traditional mutual information calculations.

6. Method 1B—Simplifying the Calculation of ROA In Real-Time Seizure Detectors 6.1 State of the Art Recurrence Quantification Analysis (RQA) is a technique used for the analysis of non-linear and chaotic systems. It is used to quantify the patterns and structures present in a recurrent plot, which captures and displays the recurrence of states in a dynamical system. When applied to EEG signals, it can be a valuable tool for seizure detection due to the non-linear dynamics of brain activities. Traditionally, the recurrence plot matrix is constructed by comparing each point in a time series to every other point. If the distance between points is below a certain threshold, it's marked as 1 (indicating recurrence), otherwise, it's marked as 0. RQA metrics are then derived from patterns found in this Recurrence Plot matrix, such as the density of recurrent points or the distribution of diagonal line lengths.

The application of RQA on real-time embedded systems, particularly for EEG signals, is a challenging task due to the computational demands of RQA and the constraints of embedded platforms. Some studies report parametric version of RQA, pRQA, allowing a fast processing of spatial arrays of time series once each is modeled by an autoregressive stochastic process. This method relies on the analytical derivation of asymptotic expressions for five current RQA measures as a function of the model parameters. By avoiding the construction of the recurrence plot of the time series, pRQA is computationally efficient, however, this technique only provides a model-fitted approximation of the values derived from real-world data, the model-fitted approximation heavily depends on the quality of a priori model fitting.

6.2 Problem Definition

The application of RQA in real-time embedded systems, particularly for EEG signals, is a challenging task due to the computational demands of RQA and the constraints of embedded platforms. The existing resource-economic approaches provide only estimates of the RQA metrics.

6.3 Description of Proposed Solution

The RQA features are normally calculated based on the Recurrence Plot matrix. Rather than constructing the entire Recurrence Plot matrix, the proposed method instead calculates a subset of measurements (e.g., the most important measurements) on the fly. This method saves memory and time, while still providing precise measures in contrast to the prior approximation and model-fitting based approaches.

FIG. 12 shows an example calculation of the RQA using the proposed approach. When calculating RQA with the proposed method, x consecutive samples of a 512-element time function are compared to all other x consecutive samples in different positions. This means approximately 512×512/2 comparisons, the result of which is the same number of bits in half a matrix. The evaluation task simplified by the proposed method is to calculate a histogram (of about 512 elements) that shows the distribution of the lengths of chains of ones that are parallel to the main diagonal of this matrix. Therefore, the histogram shows how many chains are of length 1, how many are of length 2, etc. Naturally, these chains of ones are separated by one or more zeros diagonally. It is not necessary to store the matrix to calculate the histogram; instead, with the acquisition of a new row of the matrix, one can accumulate the results For simplicity, the rows of the matrix can be conceptually shifted to the left so that the original main diagonal becomes vertical, and thus the chains that were diagonal become vertical, and the newly vertical chains can be referred to by their horizontal position. The numbers to the left of the now-vertical main diagonal are irrelevant. When a new (boolean) element arrives, if it's a 1, the variable representing the chain length in that column can be increased. But if it's a 0 and the one above it was a 1, then a chain has ended there, so the appropriate column in the histogram that represents the final result can be increased and the length-counting variable can be reset. In some embodiments, the proposed solution provides memory reduction as the matrix is not stored. The known RQA calculation uses 15 BRAM (508×508 bit=258064 bit 1 BRAM=18 kbit–>508*508/18/1024=14.0008) per channel which is not required by using the proposed solution. Example operation pseudocode is provided below:

```
function fx_RQA:
inputs: time_function, variance
output: rqa_L, rqa_RR, rqa_ENTR, rqa_DET
{
   calculate 'r' from variance value
```

-continued

```
histogram array = 0
train length counter array = 0
for (i=0...510) {
    for (j=3...511) {
        compare triplets at positions 'i' and 'j':
        if (sum_of_squares_of_differences < r) {
            increment the train length-counter in the array
        }
        else {
            increment the corresponding column in the histogram
            length counter = 0
        } // if
    } // j
} // i
// calculate the recurrence rate (RR):
// accumulate the density of recurrence points based on the histogram
    for (i=1...508) {
        RR += i * histogram[i]
    }
    // calculate the determinism (DET):
// calculate the percentage of recurrence point which have a train length > 1
DET = (RR − histogram[0]) / RR
    // calculate the entropy (ENTR):
// calculate the Shannon entropy of the probability that a diagonal line has a given
exact length > 1
// Note: diagonal trains are translated into vertical in our implementation
    for (i=1..508) {
        pp = histogram[i] / sum(histogram)
        pplog = log(pp)
        ENTR += pp * ppl
    }
    // calculate average diagonal line length > 1 (L)
// Note: diagonal trains are translated into vertical in our implementation
    L = DET / sum(histogram)
```

The proposed method offers a matrix-free approach to RQA, focusing on memory and computational efficiency. By avoiding the explicit construction of the recurrence plot matrix, leveraging a histogram for diagonal chain lengths, and employing a dynamic accumulation process, this method provides a unique perspective and approach to RQA. To summarize, the proposed method can include the following benefits:

1. Matrix-Free Approach: The known RQA method, the entire recurrence plot matrix is constructed, which means that for a time series of length N, an N×N matrix is created. The matrix is statically constructed, and metrics are derived afterward. For example, identifying and measuring diagonal lines requires scanning the matrix.

The new approach is the avoiding the explicitly construction of the recurrence plot matrix. As each new row of the 'imagined' matrix becomes known, results are accumulated without needing to reference previous rows. This approach allows an incremental counting of chain lengths. As each new element arrives, the algorithm updates the current chain length or resets it based on the new data. These offer significant memory and potentially computational savings, especially for large time series.

2. Use of Histogram for Diagonal Chain Lengths: RQA metrics, such as the distribution of diagonal line lengths, are usually derived from the full matrix. The new method directly calculates a histogram showing the distribution of lengths of chains of ones parallel to the main diagonal. Shifting each new row of the imaginary matrix to the left, the originally diagonal chains become vertical. This altered perspective simplifies the process of identifying and counting chain lengths as it reduces the problem to a column-wise consideration. This direct calculation may reduce the number of steps or iterations usually required to obtain these metrics from the full matrix.

6.4 Demonstration of Embodiments

Figure 13A:
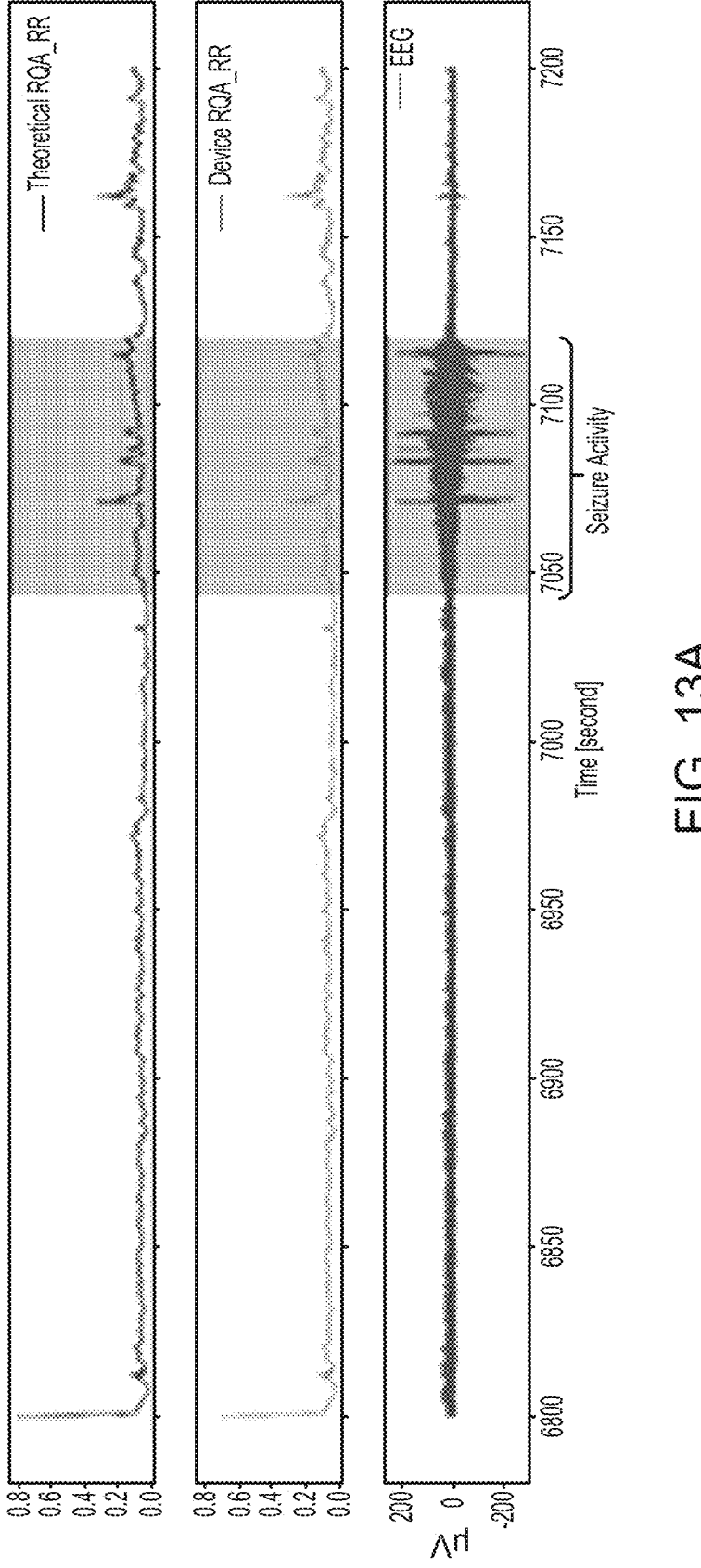
FIGS. 13A-13D show a comparison of Recurrence Quantification Analysis Values calculated from an EEG signal using two different techniques.
Figure 13B:
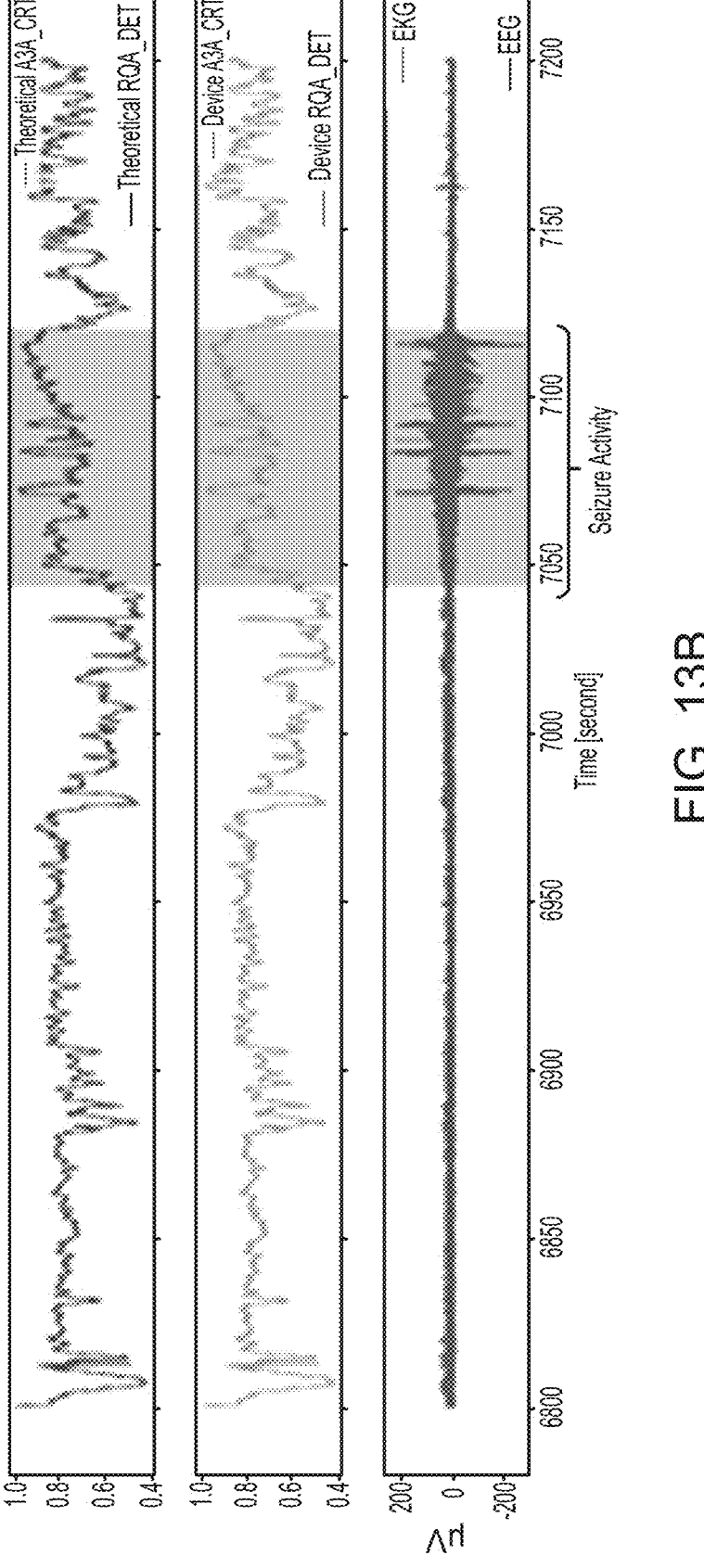
Figure 13C:
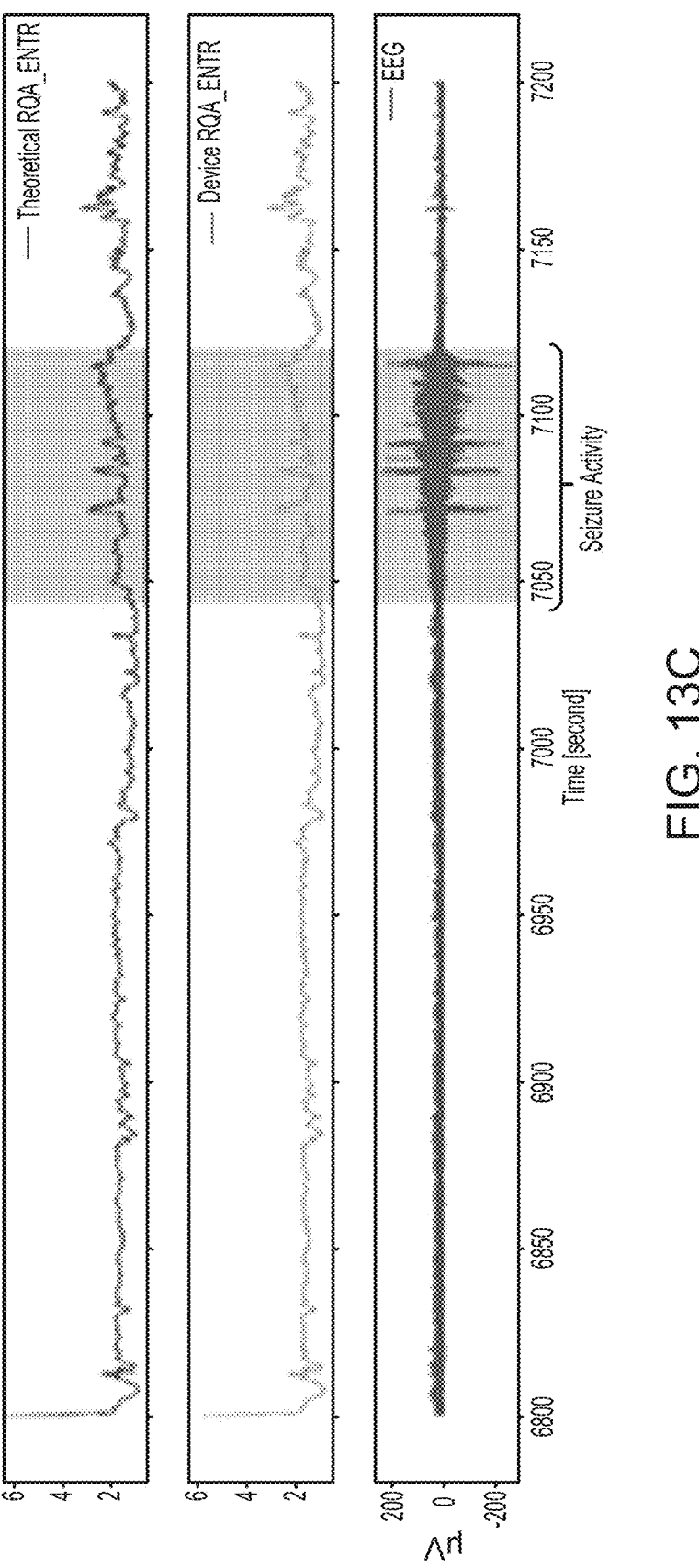
Figure 13D:
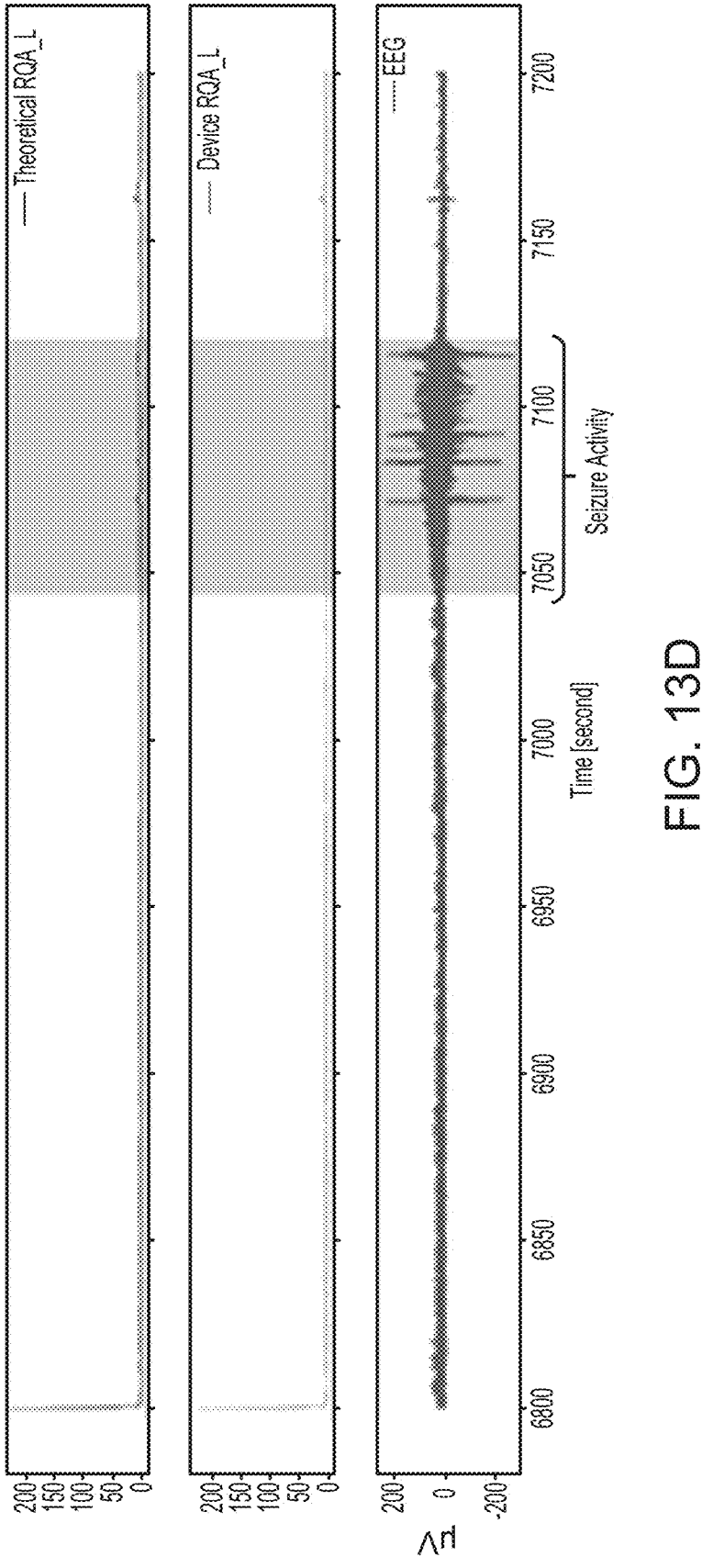

FIGS. 13A-13D show the comparison of Recurrence Quantification Analysis (RQA) Values using the known approach versus the proposed approach. Specifically, FIG. 13A shows the comparison for Recurrence Quantification Analysis Recurrence Rate (RQA_RR), FIG. 13B shows the comparison for Recurrence Quantification Analysis Determinism (RQA_DET), FIG. 13C shows the comparison for Recurrence Quantification Analysis Entropy (RQA_ENTR), and FIG. 13D shows the comparison for Recurrence Quantification Analysis Line Length (RQA_L) features. The bottom panels of each figure show an EEG recording in grey, with a seizure segment highlighted labeled. Top and Middle panels on each figure display the calculated RQA features by the known mathematics (labeled "theoretical RQA_-") and the proposed method (labeled "device RQA_-"). Note, that since the known and proposed methods result in identical values, they are displayed on separate panels to avoid full overlap.

Figure 13E:
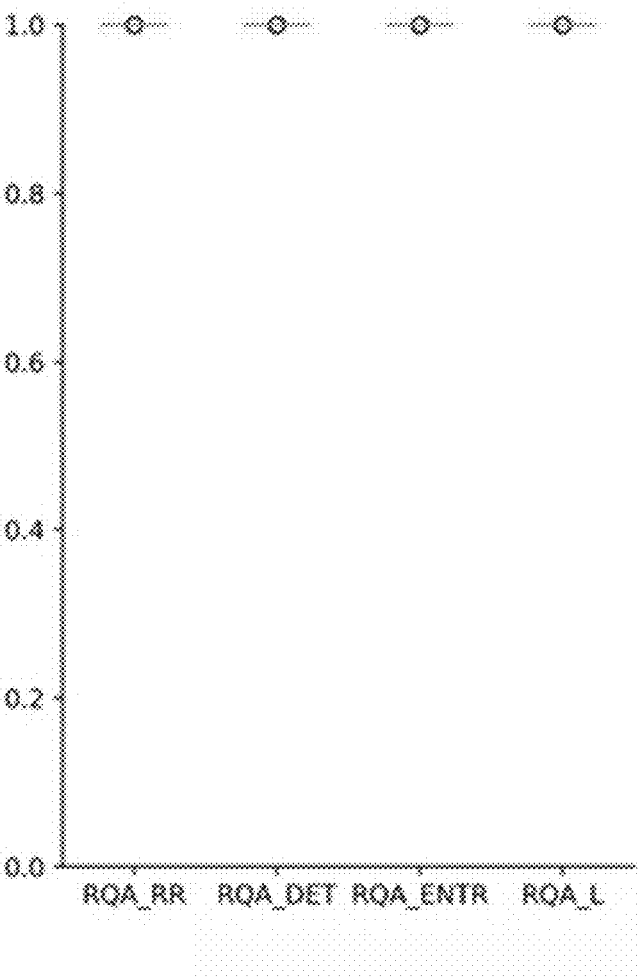
FIG. 13E is a boxplot of the correlation coefficients between the Recurrence Quantification Analysis calculated using the different techniques.

FIG. 13E and Table 3 show the similarity of simplified features (e.g., calculated using the proposed approach) and features calculated using the known mathematical definition. FIG. 13E is a boxplot comparing the correlation coefficients obtained from 32 channels using the known implementation of the Recurrence Quantification Analysis algorithm versus the proposed approach. Table 3 (below) shows comparative analysis of correlation metrics between Known and Novel Recurrence Quantification Analysis method across 32 EEG channels.

TABLE 3

| Description | Known vs. Proposed approach | | | |
| --- | --- | --- | --- | --- |
| | RQA_RR | RQA_DET | RQA_ENTR | RQA_L |
| Average Correlation Across 32 EEG Channels | 1 | 1 | 1 | 1 |
| Median Correlation Across 32 EEG Channels | 1 | 1 | 1 | 1 |
| Standard Deviation of Correlation Across 32 EEG Channels | 0 | 0 | 0 | 0 |

To see the proposed approach in operation and the effect of using the proposed approach on detection model performance, see section 9—"Demonstration of Embodiment of the Simplified Features".

6.5 Resource Economics

Traditional approaches to Recurrence Quantification Analysis (RQA) rely heavily on a comparison matrix to record pairwise similarities between data points, as well as histograms to summarize the recurrence structure. Therefore, known methods, while functional, impose significant demands on memory and computational resources, particularly in embedded systems.

In known approaches, memory requirements for the comparison matrix include 128 kbits, typically implemented as 8 instances of 18 kbit BRAMs. Memory requirements for histogram include 512 words, each 9 bits wide (1×18 kbit BRAM). The known approach has a time complexity per comparison of 3 clock cycles per pair (1 for the comparison, 1 to read the histogram column, 1 to write the updated column). Matrix storage and retrieval uses an additional cycle to store results in the comparison matrix. Therefore, a total time complexity is approximately 3×128 k clock cycles (e.g., 4 ms per channel).

In some embodiments, the methods described herein can eliminate the need for explicit storage of the comparison matrix by directly processing recurrence events. Key advantages include (i) using no comparison matrix, which can save 128 kbits of memory; and (ii) optimized clock cycles, which can avoid 1×128 k clock cycles required to write and read the comparison matrix, thereby reducing computational time by 1.3 ms per channel. Therefore, in some embodiments, resource savings of the methods described herein for memory include removing the need for a 128 kbit comparison matrix. In some embodiments, resource savings for time include achieving a 30% reduction in clock cycles per channel by bypassing matrix storage and retrieval.

In some embodiments, the proposed approach for RQA demonstrates a substantial improvement over the known method, achieving an 88% reduction in memory usage and a 30% reduction in computational time, which enhances the feasibility of implementing RQA in real-time, resource-constrained environments such as embedded systems for wearable biomedical devices.

7. Method 1C—Simplifying the Calculation of Coherence in Real-Time Seizure Detectors 7.1 State of the Art Cross-channel coherence in EEG measures the linear synchronization between signals of two different channels in the frequency domain. It provides insight into the functional connectivity between different brain regions represented by the channels. In some known methods, coherence of two EEG channels is calculated the following way: first, for each of the two EEG channels, the power spectral density is computed (usually by a variant of the Fourier Transform).

For example, many applications utilize Welch's overlapped averaged periodogram method (or a variant of it), which performs multiple Fourier transforms of the segmented data to obtain the spectra of non-stationary signals such as EEG. Then, the cross-spectral density between the EEG channels is calculated. The cross-spectral density between EEG channels represents the shared frequency content between the two channels. Lastly, the coherence is calculated using the formula:

$$\text{Coherence} = |\text{Cross−Spectral Density}|^2 /$$

$$(\text{Spectral Density (Channel 1)} \times \text{Spectral Density (Channel 2)})$$

The output of this equation gives a value between 0 (no coherence) and 1 (perfect coherence). For multiple EEG channels, each pairwise coherence is calculated iteratively.

7.2 Problem Definition

Storing the cross-spectra and auto-spectra of each EEG channel and each EEG channel pair in the current coherence embodiments are resource-intensive (large memory footprint), especially for long time series 7.3 Description of the Proposed Solution Example Pseudocode is as Follows:

```
function fx_COHER:
input: slw = 33 time functions
output: coher array of 33
coher array = 0
for all freq bins (n=0..64) {
    for each channel {
    divide time_function into 7 overlapping 128-long segments
    apply Hamming window to each segment
    calculate the n-th freq. component for all 7 segments
    calculate 'sum_of_7_magnitude_squares'
}
for each channel A {
    for each channel B {
        if (cha!=chb) {
        'cross_magnitude_square' = sum of 7 cross products of freq
components (chA * complex conjugate of chB)
        coher[cha]  +=  cross_magnitude_square  /
sum_of_7_magnitude_squares
        } // if (cha!=chb)
    } // for chb
} // for cha
} // for n
```

The proposed solution is to calculate the coherence using an optimized algorithm to reduce resource needs in real-time systems, which would be a bottleneck should the pairwise coherence of multiple channels be used. Instead of calculating the full cross-spectral density maps for each channel pair, the power of each frequency component is estimated one-by-one, and the frequency specific coherence is calculated. This is realized by the convolution of the signal by a frequency-specific sine kernel, as a form of a manually implemented partial Fourier transform. These frequency-specific coherence values are then cumulated to obtain the coherence of the full spectra. Since the approximation of the spectral density maps would be obtained iteratively frequency-by-frequency anyway, this does not increase computational costs significantly. In other words, for each specific frequency, the power of that frequency is calculated by a convolutional method for all channels, then the relevant frequency-specific cross-coherences are calculated. Then the actual powers and cross channel coherences can be discarded, freeing up significant memory before moving to the next frequency bin.

The proposed approach completes the calculation of cross-channel coherence without storing the memory intensive spectral density maps, by implementing nested loops in a non-trivial way, and by estimating the power of only a given frequency at a time. In coherence computations, Discrete Fourier Transform (DFT) is performed once for the time series, that delivers the full spectra of the signals and is stored for the pairwise coherence calculations. In the proposed approach, the entire spectral analysis is performed 65 times, once for each frequency component. This repeated analysis reduces memory need.

FIG. 14 shows an example calculation of the coherence using the proposed approach. Coherence is fundamentally calculated by taking two channel pairs (dividing them into segments, etc.), computing the cross-spectrum ($F_{xy}$) and the auto-spectra ($F_{xx}$, $F_{yy}$). These values are stored in a rather large 3-dimensional array of size [ch_num]×[section_num]×[FFT points/2 num], where the coherence of one particular channel with the other channel is stored. As iteration occurs over the channel pairs, the coherence is accumulated with the other currently active channel. The proposed algorithm requires only one [ch_num][section_num] sized, 2-dimensional array of complex values to be stored. So, in the current embodiment, instead of creating a matrix of [32]× [7]×[65] elements, which due to the required precision would not even fit in most FPGAs, the size of the array is only [32]×[7]. In conclusion, the essence of the coherence calculation is consistent with standard methods, the iterative spectral analysis for each frequency component differs from current approaches.

7.4 Demonstration of Embodiment

Figure 15A:
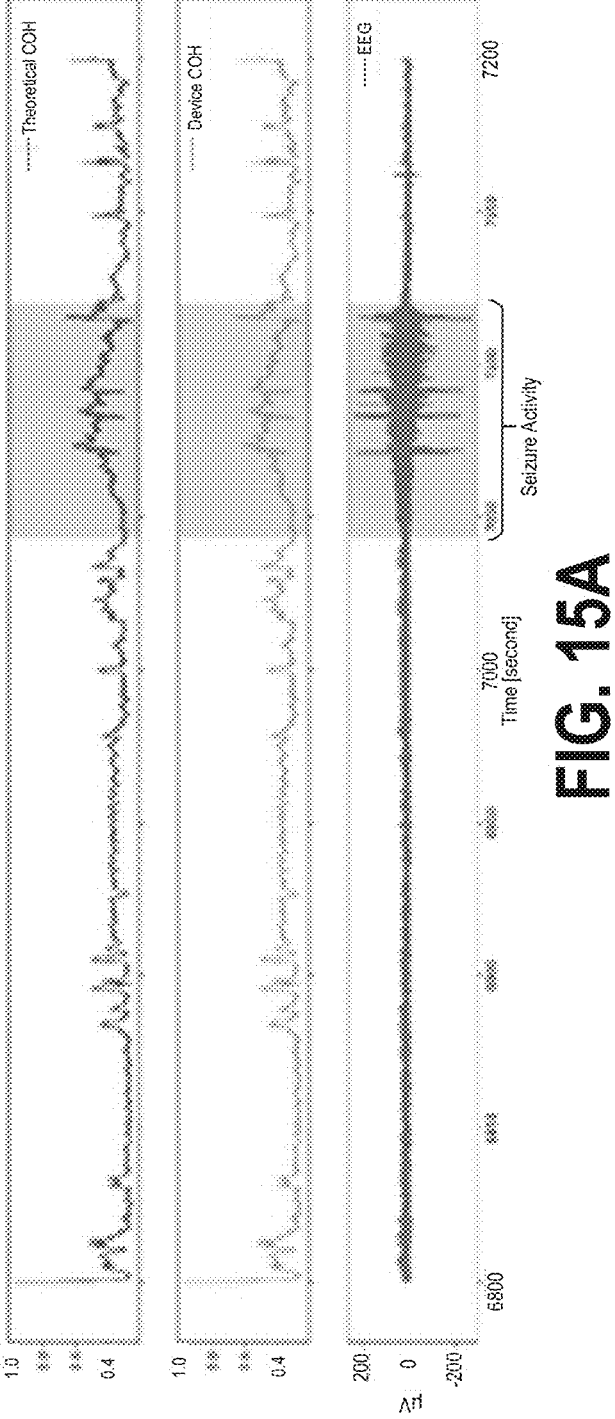
FIG. 15A-15B shows a comparison of Coherence Feature Values calculated from an EEG signal using two different techniques.

FIG. 15A shows the comparison of Coherence Values calculated using the known approach versus the proposed approach. The bottom panel shows an EEG recording in grey, with a seizure segment labeled. Top and Middle panels display the calculated coherence feature of the EEG channel against the other EEG channels (not shown) by the known mathematics (labeled "theoretical COH") and the proposed method (labeled "device COH"). Note, that since the known and novel methods result in identical values, they are displayed on separate panels to avoid complete overlap.

Figure 15B:
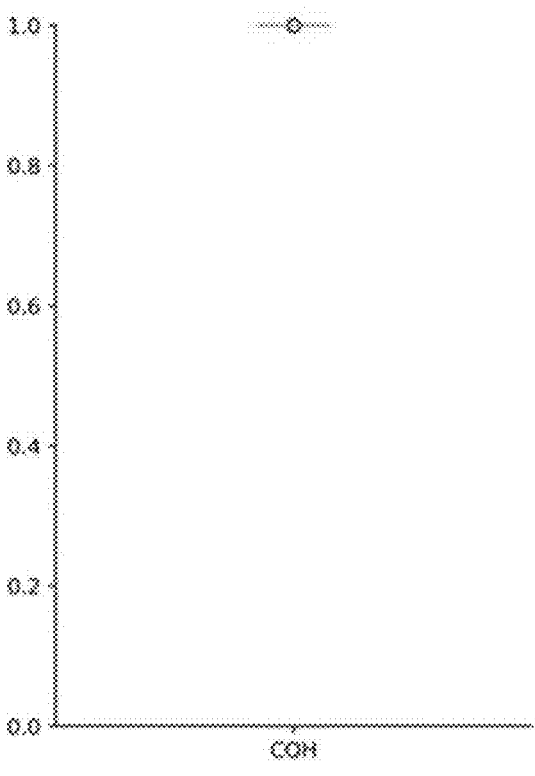

FIG. 15B and Table 4 show the similarity of simplified features (e.g., calculated using the proposed approach) and the features calculated using the known mathematical definition. FIG. 15B is a boxplot comparing the correlation coefficients obtained from 32 channels using the known implementation of the Coherence algorithm versus the proposed approach. Table 4 shows comparative analysis of correlation metrics between known and proposed Coherence calculation method across 32 EEG channels.

TABLE 4

| Description | Known vs. proposed approach |
| --- | --- |
| Average Correlation Across 32 EEG Channels | 1 |
| Median Correlation Across 32 EEG Channels | 1 |
| Standard Deviation of Correlation Across 32 EEG Channels | 0 |

To see the proposed approach in operation and the effect of using the proposed approach on detection model performance, see section 9—"Demonstration of Embodiment of the Simplified Features."

7.5 Resource Economics

In the known approach, memory requirements can include memory to accommodate 65×7×33 complex frequency components, with each component requiring 2×35 bits to represent real and imaginary parts. This results in a significant memory burden due to the need to store the entire frequency spectrum.

The proposed approach described herein optimizes coherence calculations by processing only one frequency component at a time. In some embodiments, the proposed approach reduces storage requirements to 7×33 complex frequency components (2×35 bits each) at any given time, as only the current frequency is processed. In some embodiments, the proposed approach achieves a 98.4% reduction in memory usage by avoiding the storage of the entire frequency spectrum.

8. Method 1D—Simplifying the Calculation of Frequency Band Powers Using Wavelets in Real-Time Seizure Detector

8.1 State of the Art

Figure 16A:
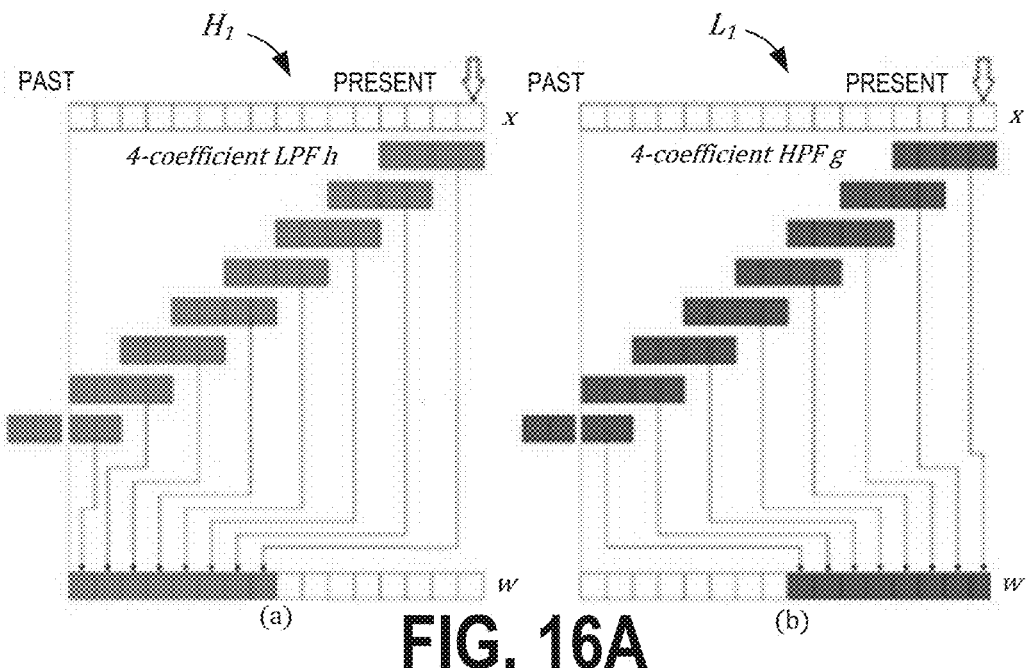
FIG. 16A-16B are diagrams depicting a known method for calculating a DB4 discrete wavelet transform.

EEG signals have many frequency-domain features proved to be useful in pattern (e.g., epileptic seizure) detection. Frequency domain features can be obtained by converting the time series of EEG signals into the frequency domain. In most cases this is done either by applying a form of Fourier transform, or by Wavelet transform, most commonly by Daubechies-4 Discrete Wavelet Transform. The DB4 Discrete Wavelet Transform does this conversion in a way that the N-element time function is decomposed into two N/2-element functions by a sweeping convolution of a 4-element scaling vector and a 4-element wavelet vector as shown in FIG. 16A.

The L1 and H1 (low-pass and high-pass, respectively) scaling filters are calculated recursively following the standard equations. The low-pass Scaling Filter vector coefficients for DB4 are:

$$c_0 = \frac{1+\sqrt{3}}{4\sqrt{2}}, \quad c_1 = \frac{3+\sqrt{3}}{4\sqrt{2}}, \quad c_2 = \frac{3-\sqrt{3}}{4\sqrt{2}}, \quad c_3 = \frac{1-\sqrt{3}}{4\sqrt{2}}.$$

$$appx. \quad 0.48 \quad 0.84 \quad 0.23 \quad -0.13$$

Figure 16B:
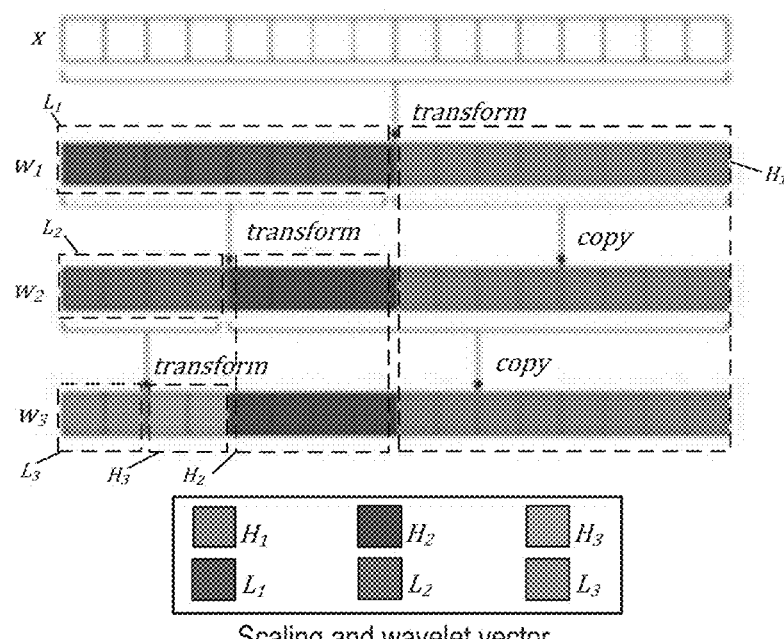

The high-pass Wavelet Filter vector coefficients are: {c3, −c2, c1, −c0}. The above-described process is repeated recursively for the Scaling side (see the L1, L2 and L3 halves in FIG. 16B). DB4 Feature output for levels 1 . . . 6 are the Sum of Squares of H1, H2, H3, H4, H5 and H6. Some works implement buffering solutions aiming to process data across the borders of the data segments without relying on traditional techniques like periodic convolution, mirror padding and function windowing in order to improve accuracy of online calculations. Some other works enhance the immediate availability of the subsequent levels of decomposition by implementing an approach that does not use a subsampling process.

8.2 Problem Definition:

Current DB4 solutions are based on a window frame of data samples, and data samples from the past are estimations only. As shown in FIG. 15A, both the L1 and the H1 (LP & HP) filters run out of real data (e.g., shown as protruding to the left on the figure) due to the edge effect, thus need to rely on estimates. The known methods also suffer from redundant calculations and consequent long run time. For every subsequent calculation of the wavelet power in a sliding window that has an overlap, one has to run thru the whole window of samples every time and make assumptions for the sample values in the past, while most of the content of the window does not change but only shifts within the window, but the oldest ones fall off, and a few new data points are added.

8.3 Description of Proposed Solution:

The proposed solution is to calculate DB4 on-the-fly. Every time two new samples enter the window, their effect is added to the final feature value, and the effect of the leaving two old samples is subtracted. Thus, no edge effect occurs, and runtime is about 10× times faster in the current embodiment. In detail, a DB4 Discrete Wavelet Transform performs the convolution of the data as the data is acquired instead of using windowed segments accumulated over time. All levels are calculated on-the-fly in a hierarchy, using only the latest and the oldest samples. The reason for this is that the calculation of the leftmost (first) element of the output (result) vectors requires two preceding values in the original vector, elements −1 and −2. This makes on-the-fly calculation more convenient and accurate, as opposed to sliding window-based calculation, because it alleviates edge-effects of windowed convolution, where the calculation of the initial samples of the result would require out-of-windows samples too, as the kernel overexpands the available dataset.

Known calculation of the DB4 transform on discrete sliding windows would involve running through the overlapping samples of the consecutive windows repeatedly, making part of the calculations redundant. Re-using the convolutions from the previous, overlapping window can reduce this overhead.

Overall, the proposed on-the-fly calculation may provide at least two benefits. First, adding the effect on the most recent incoming samples and subtracting the effect of the dropping data from the transform at each level, rather than recalculating the whole transform, thereby reducing redundant calculations. Second, the required actual out-of-window edge-samples can also be made available relatively simply. Lastly, the final sum of squares calculation used to approximate signal energy as the output of the function also takes less operations when performed on-the-fly. Example operation pseudocode is provided below:

The proposed DB4 wavelet transform method provides a real-time, on-the-fly approach to wavelet decomposition, focusing on computational efficiency and accurate handling of edge effects. The traditional DB4 DWT involves taking a discrete segment of data, performing the wavelet transform, and then moving the segment (often with overlap). The new method performs the convolution as data is acquired, without relying on windowed segments accumulated over time. This approach can better handle edge effects, which are typically present when convolution kernels extend beyond the available data in windowed methods. Moreover, standard DWT computation is typically applied on the entire dataset or segment. However, the proposed method calculates all levels on-the-fly in a hierarchical manner, leveraging only the latest and the oldest samples. This strategy is more efficient and avoids recalculations due to overlapping samples in windowed approaches.

8.4 Demonstration of Embodiment

Figure 17A:
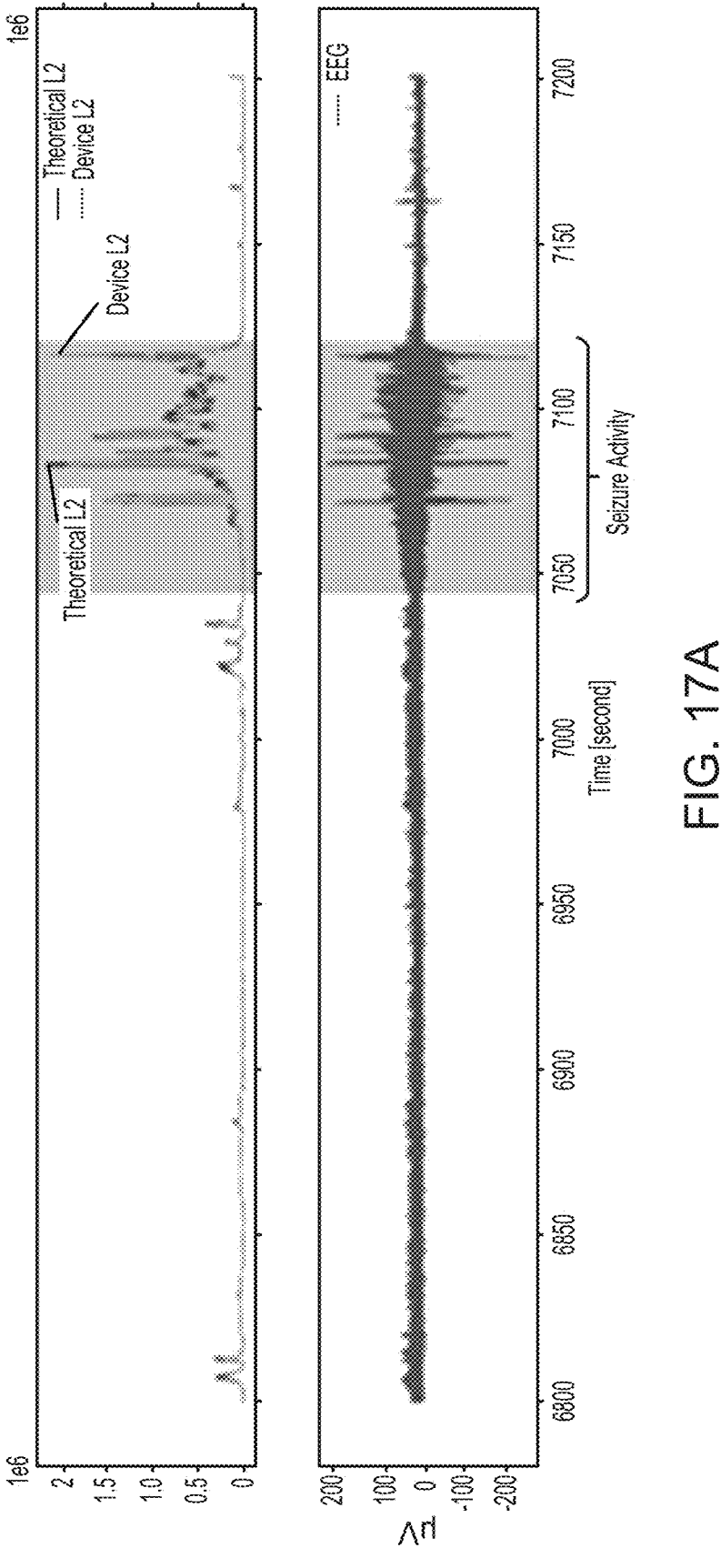
FIGS. 17A-17E show a comparison of Frequency Band Powers calculated from an EEG signal using two different discrete wavelet transform techniques.
Figure 17B:
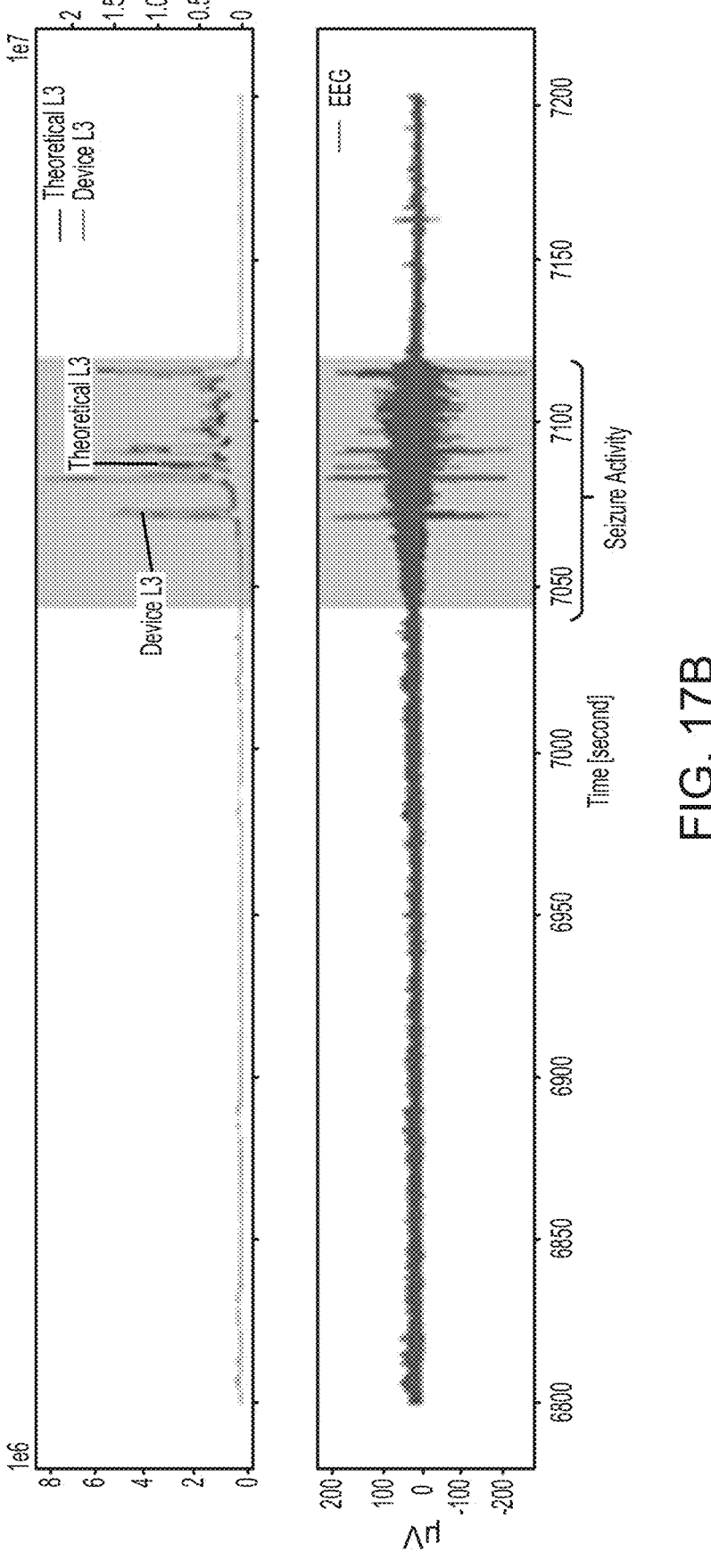
Figure 17C:
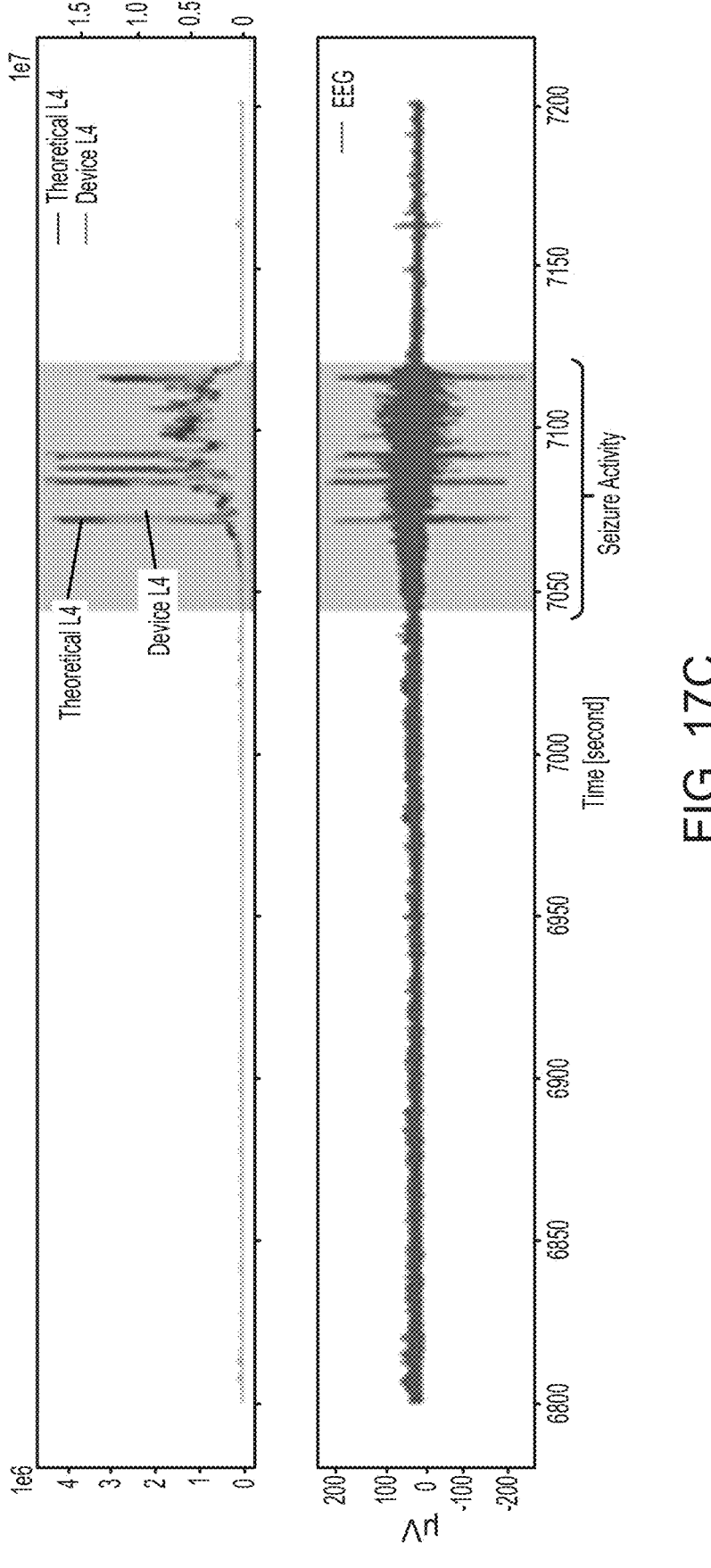
Figure 17D:
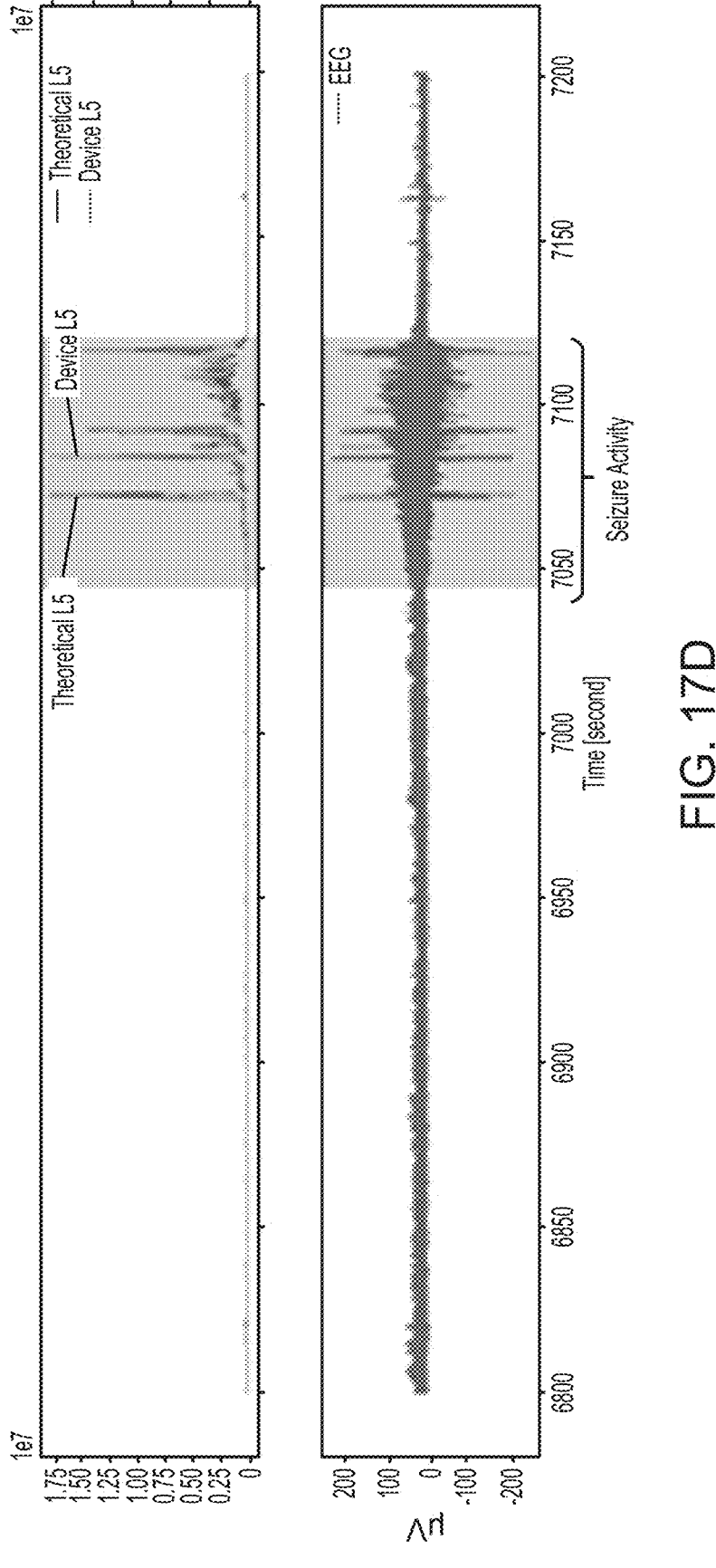
Figure 17E:
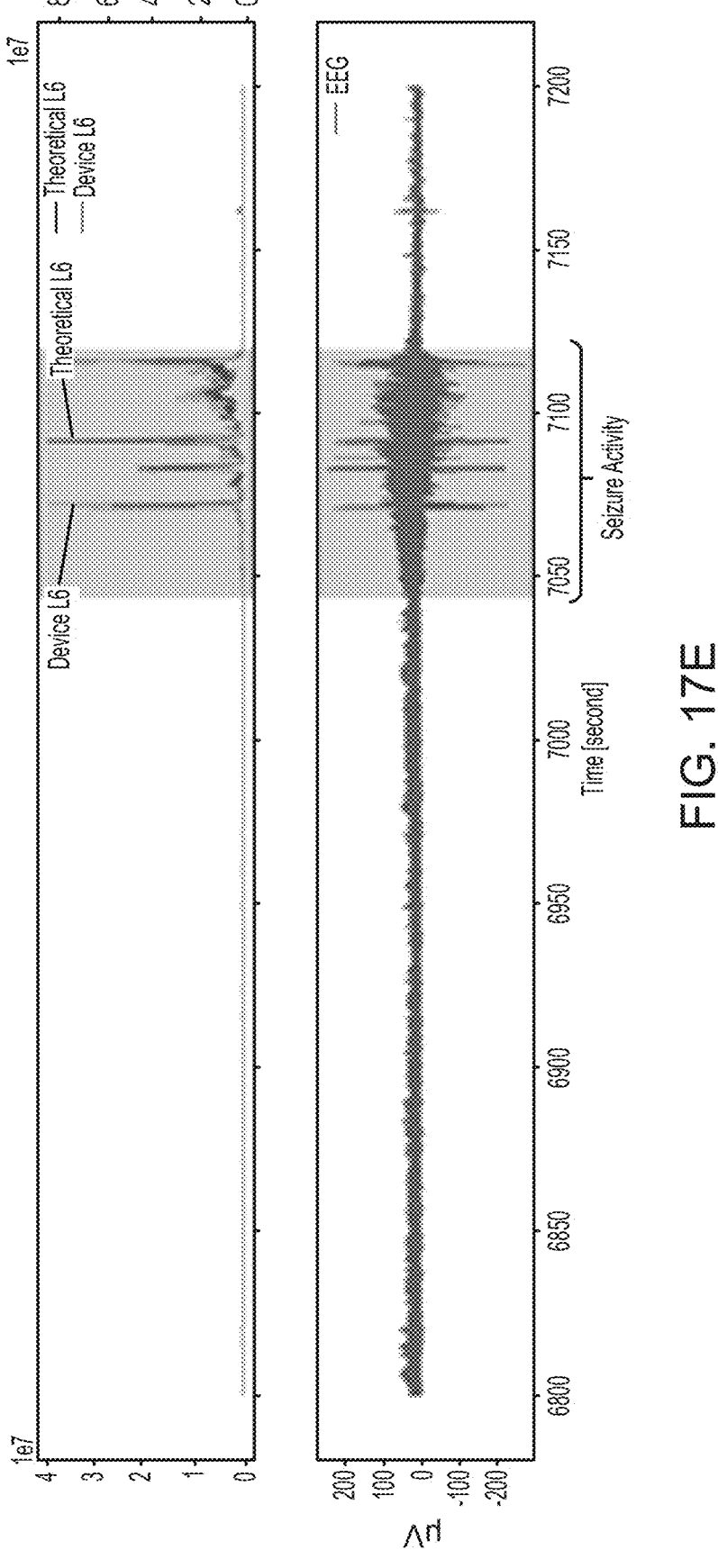

FIGS. 17A-17E show a comparison of Frequency Band Powers calculated using the known approach versus the proposed approach. FIG. 17A show the values of L2 (highest) wavelet band powers, FIG. 17B shows the values of L3, FIG. 17C shows the values of L4, FIG. 17D shows the values of L5, FIG. 17E shows the values of L6 (lowest). The bottom panels of each figure show an EEG recording in grey, with a seizure segment labeled. The top panel on each figure displays the calculated wavelet-band power feature by the known mathematics (labeled "Theoretical L-") and the proposed novel method (labeled "Device L-").

Figure 18:
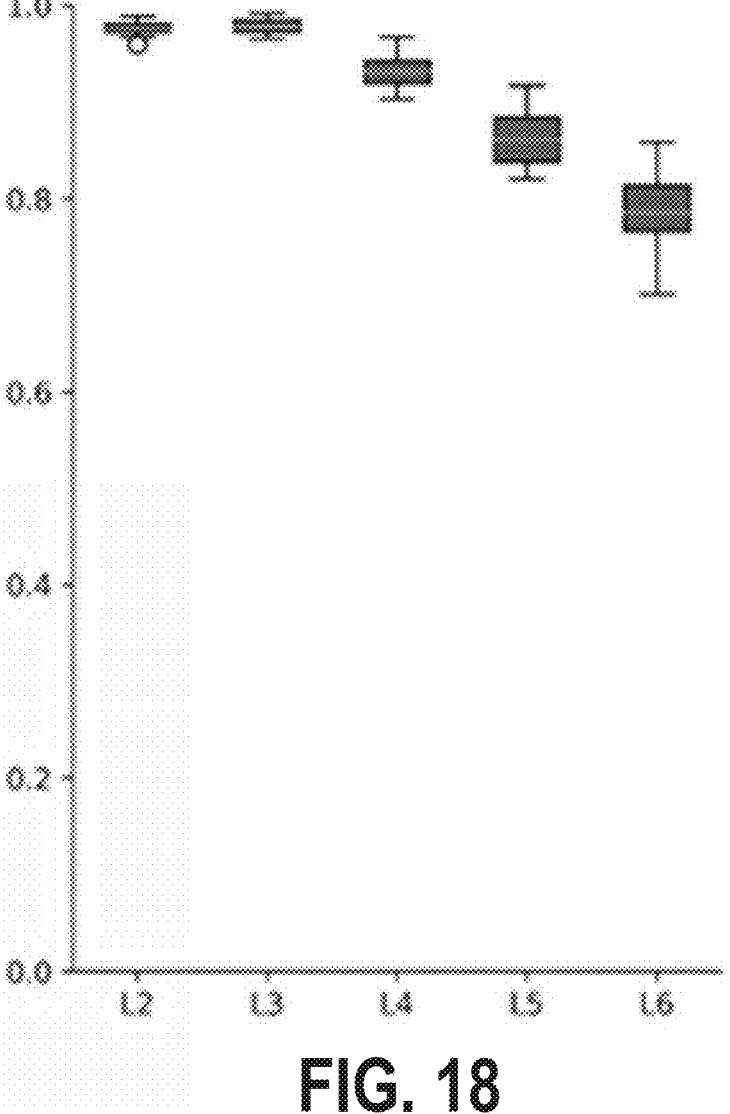
FIG. 18 is a boxplot comparing the correlation coefficients of Frequency Band Powers calculated by different approaches.

FIG. 18 and Table 5 show the similarity of simplified features (e.g., calculated using the proposed approach) and the features calculated using the known mathematical definition. FIG. 18 is a boxplot comparing the correlation coefficients obtained from 32 channels using the known implementation of the Frequency Band Powers versus our proposed approach using wavelets. Table 5 shows the comparative analysis of correlation metrics between the Frequency Band Powers versus our proposed Novel approach using wavelets across 32 EEG channels.

```
function fx_DB4:
input: time_function
output: Level 1..5
nL = sample new ( just entered the sliding window )
dL = sample old ( just left the sliding window )
create 6 accumulators for L0...L5 Levels of DB4
create 1 accumulator for L5_LPF
do this on every 2nd entering/leaving sample {
apply a 4-element high pass filter on the newest 4 nL samples,
add the 4 filtered samples,
square the sum and add to the accumulator of that Level.
Apply a 4-element high pass filter on the oldest 4 dL samples (2 from prev. window
and 2 from this window),
add the 4 filtered samples,
square the sum and subtract from the accumulator of that Level.
Apply a 4-element low pass filter on the newest 4 nL samples,
Next level nL = sum of the 4 filtered samples.
If (Level==5) square the sum and add to the accumulator of Level_5.
Apply a 4-element low pass filter on the oldest 4 dL samples (2 from prev. window
and 2 from this window)
Next level dL = sum of the 4 filtered samples.
If (Level==5) square the sum and subtract it from accumulator of Level_5.
}
Outputs are 5 accumulators (L1 ... L5).
Accumulator L5_LPF is used by the REL feature only.
```

TABLE 5

| Description | Known vs. Novel approach | | | | |
| --- | --- | --- | --- | --- | --- |
| | L2 | L3 | L4 | L5 | L6 |
| Average Correlation Across 32 EEG Channels | 0.976 | 0.978 | 0.933 | 0.863 | 0.787 |
| Median Correlation Across 32 EEG Channels | 0.975 | 0.977 | 0.932 | 0.861 | 0.785 |
| Standard Deviation of Correlation Across 32 EEG Channels | 0.006 | 0.007 | 0.017 | 0.028 | 0.031 |

To see the proposed approach in operation and the effect of using the proposed approach on detection model performance, see section 9—"Demonstration of Embodiment of the Simplified Features.

Figure 19A:
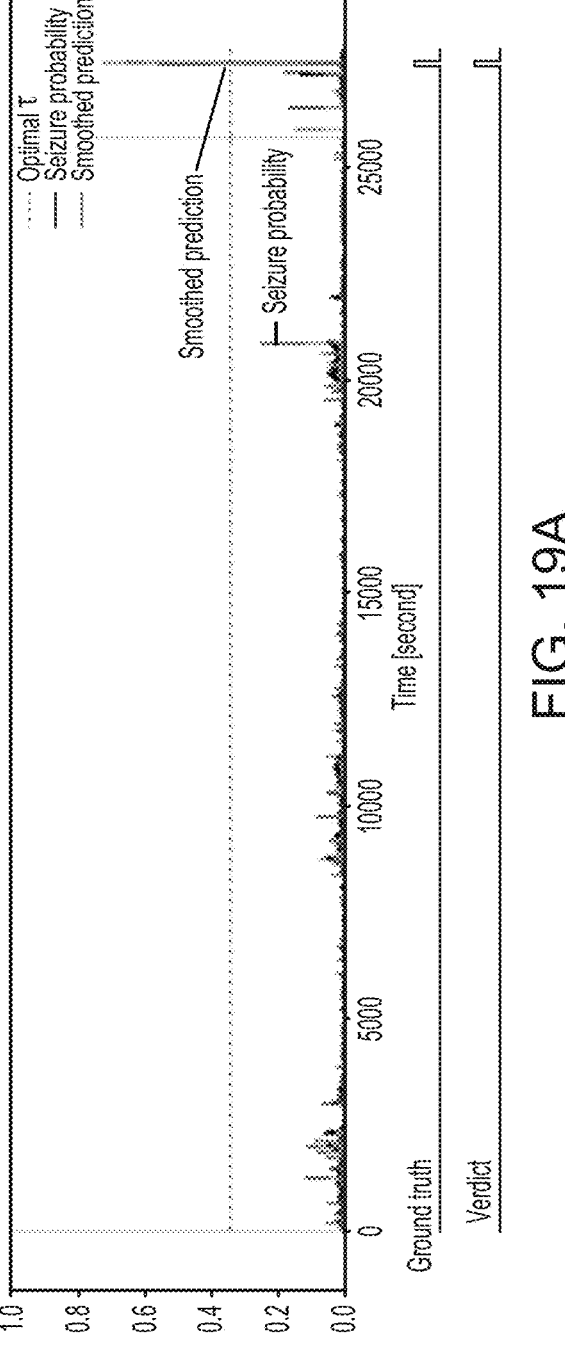
FIGS. 19A-19D show a comparison of efficacy of different detection algorithms that use different techniques for calculating features.
Figure 19B:
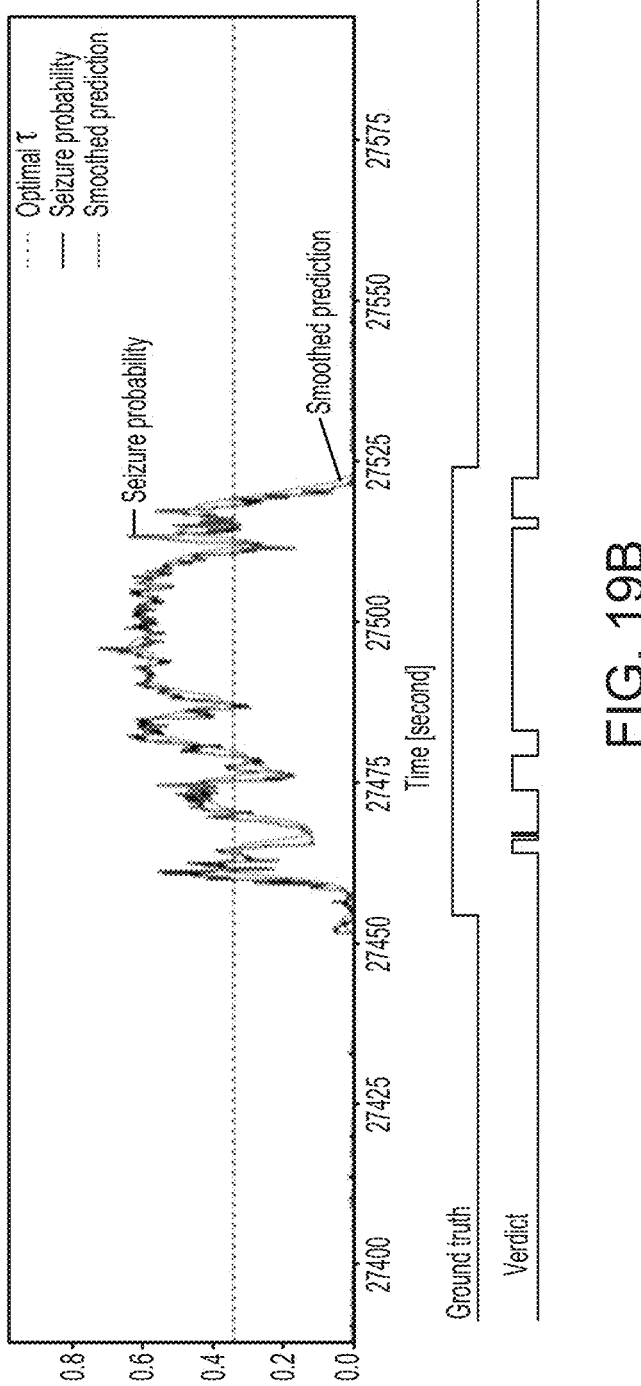
Figure 19C:
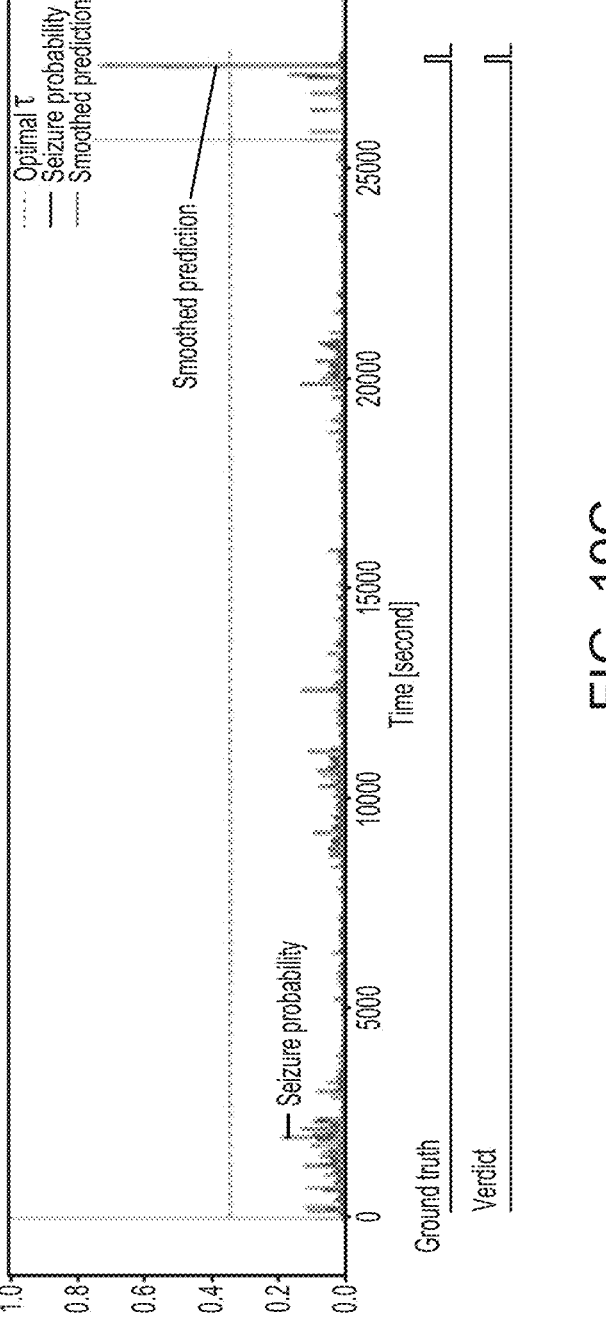
Figure 19D:

9. Methods 1A-1D—Demonstration of Embodiment of the Simplified Features:

FIGS. 19A-19D show a comparison of detection model efficacy based on the simplified features versus the original math (e.g., known method). FIG. 19A-19B show results for the proposed approach using simplified features, and FIG. 19C-19D show results for the known approach using original math features. As shown, the performance of the detector model on the original math features and on the simplified features are almost identical. The detector performance using the simplified features was: Area Under the Sensitivity-Specificity ROC curve (AUC): 0.9940; False Alarm Rate (FAR): 0.0; Event Detection Quality (EDQ): 0.7166, while the performance using the features calculated using the known math was: AUC: 0.9952; FAR: 0.0; EDQ: 0.7496 (T-test; P value=0.999; df=560).

10. Method 2—Adaptive Thresholding of Decisions in Real-Time Seizure Detection 10.1 State of the Art Most real-time systems, especially those designed for seizure detection using EEG signals, predominantly rely on static thresholds for decision-making. These thresholds, while static during the operation, can be fine-tuned to be patient-specific, ensuring that the system is tailored to the unique characteristics of individual patients' EEG signals. Some studies implemented patient-specific threshold-based accelerator suitable for long-term continuous monitoring of patients. Other studies emphasize the patient-specific nature of seizure detection, highlighting the challenges of developing a universal seizure detection algorithm due to EEG's non-stationarity. Some systems bypass the threshold-based approach entirely, opting instead for non-threshold-based decision-making methods. For instance, certain systems employ the K-Nearest Neighbors (KNN) method, which classifies data points based on how their neighbors are classified, rather than relying on a predefined threshold.

10.2 Problem Definition

As of now, no system embodies a mechanism that dynamically alters the decision threshold based on the outcomes of past decisions. Such a mechanism would recognize that subsequent windows of data are not independent. For example, if a window of EEG data is determined to represent a 'seizure', the likelihood that the following window also represents a 'seizure' is higher. This temporal clustering of decision outcomes is not currently addressed in existing systems.

10.3 Description of Proposed Solution

The proposed approach introduces dynamic thresholding to the decision-making process of a Random Forest classifier. By leveraging the inherent temporal dependencies in subsequent windowed EEG signals, the decision threshold dynamically adapts based on recent classifications. Specifically, each positive classification (indicating a seizure) reduces the threshold, while each negative classification incrementally increases it, within preset bounds. By adapting the threshold in this manner, the system ensures consistent classification even in the face of minor fluctuations in seizure characteristics, preventing fragmented detections. Conversely, as a seizure episode ends, the threshold is gradually raised, safeguarding against sporadic false positives due to random non-seizure-related fluctuations. Furthermore, by incorporating median filtering on the thresholded decisions, the proposed solution accounts for and even leverages the temporal dynamics of EEG signal changes, ensuring robust and consistent detection with minimal computational overhead. These approaches make the classifier tending to preserve its actual state, fostering a consistent and stable decision-making process without abrupt changes. In the proposed solution, outputs of a classifier (e.g., a decision tree) are averaged and a decision is made by the thresholding of this average value. The thresholding of the average (e.g., the 'consensus vote') of the decision trees is done by employing a dynamic threshold. Adaptive thresholding may be preferable because consecutive decisions of the classifier are not independent from each other. For example, within a seizure, there is a higher likelihood of a 'seizure' sample following the previous sample already classified as 'seizure'. Interictally an opposite trend occurs: the likelihood of a non-seizure segment following a non-seizure segment is higher. In other words, since the state change of the system is less common than not, there is a bias of the classifier toward keeping the previous state from sample-to-sample. This a priori knowledge is incorporated in the dynamic thresholding, where the actual threshold value is affected by the previous decisions, making the decisions more consistent and persistent in time, without abrupt changes. A simplified method to set limits of the dynamic threshold is also described.

Figure 20:
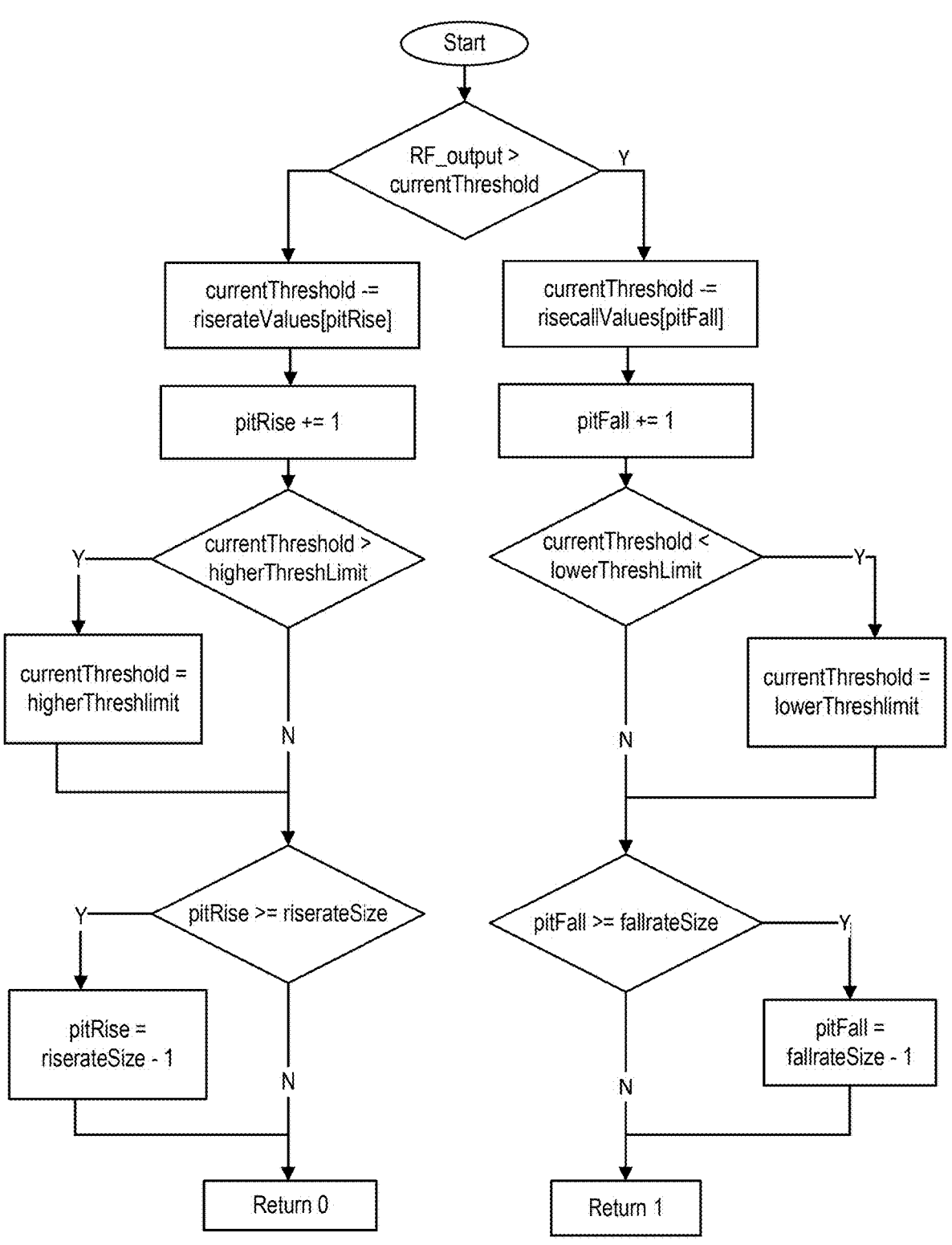
FIG. 20 is a block diagram of an example method of using dynamic thresholding for seizure detection.

FIG. 20 shows a block diagram of an example method of using dynamic thresholding. When the detector model is executed, the detection threshold moves between two extremes, in a way that every frame that is classified negative (i.e., non-seizure) increases the threshold value step-by-step until a ceiling value is reached; while every frame that is classified as positive (i.e., seizure) decreases the threshold until a floor value is reached. The increment and the decrement may be either constant or may follow any arbitrary dynamics (e.g., a second or a third identical classification causes larger steps than the first one, etc.). The floor and the ceiling is optimized in an iterative process to maximize detector performance in terms of true negative and true positive detections versus false negatives and false positives. Resultingly, frames consecutively being classified as seizure around the onset of a seizure decreases the detection threshold and ensures that most frames of the seizure are correctly classified, despite minor qualitative fluctuation of the seizure characteristics that would otherwise result in a few mis-classified frames and fragmented detection. Once the seizure is over and a number of frames are classified as non-seizure despite the low threshold, the threshold gradually increases to ceiling, ensuring that the random non-seizure related fluctuations of the classification output do not result in sporadic false positive detections.

In some embodiments, the values of the step-by-step increments and decrements used at phase transitions may not be constant. By defining an array of values to be used as 'steps' for the consecutive incremental or decremental steps, the dynamics of the shift can be adjusted. For example, defining small step values in the array followed by increasing step values makes the adaptive change 'lazy' or less likely to shift, while the inverse (e.g., large step values in the array followed by decreasing step values) makes the adaptive change aggressive (e.g., the first state-change detection immediately causes a large shift in the threshold that then slowdown in approaching the set limit.) The parameters of the current embodiment are as shown in Table 6:

TABLE 6

| Parameter name | Description |
|---|---|
| startThreshold | The initial value of the threshold |
| fallrateSize | The length of the fallrateValues array |
| lowerThresholdLimit | Lower limit, the threshold will be saturated on this level |
| riserateSize | The length of the riserateValues array |
| higherThresholdLimit | Higher limit, the threshold will be saturated on this level |
| fallrateValues | Contains the fall rate values (step-by-step decrements) of the threshold |

TABLE 6-continued

| Parameter name | Description |
|---|---|
| riserateValues | Contains the rise rate values (step-by-step decrements) of the threshold |

Lastly, the detector model also accounts for the temporal dynamics of the changes in the signal. For example, median filtering of the consecutive thresholded decisions can eliminate the false positive alarms in case of sporadic positive decisions. In some embodiments incorporating a (e.g., tail-heavy) kernel in this temporal filtering can detect preset temporal dynamics of the change in seizure-likelihood. Similarly, some embodiments may incorporate a short-term temporal "memory" for the calculated features themselves, and then account for the detection of the temporal dynamics at the level of the classification; however, this method may be more resource-intensive due to the high volume of data to store. Embodying the detection of temporal dynamics post-classification uses minimal computational resource, while still providing the desired efficacy.

The parameters of the dynamic thresholding (i.e., upper and lower limits, dynamics of threshold shift, kernel of temporal filtering) for the decision making can be automatically adjusted based on either the patient specific circadian prevalence pattern (e.g., setting the system more sensitive during periods with high chance of seizure prevalence), or on the circadian characteristics and artifact profile of the interictal EEG (e.g., setting the detector more sensitive during night-time when less artifacts are present, or during daytime when the patient performs more critical activities). Example operation pseudocode is provided below:

```
Given Parameters:
    riseRateValues: Array[Float32]
    fallRateValues: Array[Float32]
    riseRateSize: Int = length of riseRateValues
    fallRateSize: Int = length of fallRateValues
    startThreshold: Float32
    lowerThresholdLimit: Float32
    upperThresholdLimit: Float32
    decisionBufferSize: Int
    decisionBuffer = Deque[Int](maxsize=decisionBufferSize)
Algorithm:
    fallIndex: Int = 0
    riseIndex: Int = 0
    currentThreshold: Float32 = startThreshold
    for each probability value from model prediction:
        adaptiveThresholdVerdict: Int = if (probability >= currentThreshold then 1
else 0)
        insert adaptiveThresholdVerdict into decisionBuffer
        medianFilteredVerdict: Int = median of values in decisionBuffer
        # the median of the last 'decisionBufferSize' decisions
        output medianFilteredVerdict
        # Change the parameters that govern the parameter dynamics.
        if probability >= currentThreshold:
            # decrease current threshold
            currentThreshold = max(currentThreshold - fallRateValues[fallIndex],
lowerThresholdLimit)
            riseIndex = 0
            fallIndex = min(fallIndex + 1, fallRateSize - 1)
        else:
            # increase current threshold
            currentThreshold = min(currentThreshold + riseRateValues[riseIndex],
upperThresholdLimit)
            riseIndex = min(riseIndex + 1, riseRateSize - 1)
            fallIndex = 0
```

The incorporation of a priori knowledge about the temporal dependencies between consecutive EEG segments increases accuracy of the proposed method compared to traditional static thresholding techniques. Additionally, using median filtering to account for the inherent temporal dynamics of EEG signals is a pioneering step in EEG pattern detection. This multifaceted, temporally aware decision-making system provides a significant advancement in the realm of EEG-based seizure detection, optimizing detection efficacy while minimizing computational resources.

10.4 Demonstration of Embodiment

Figure 21A:
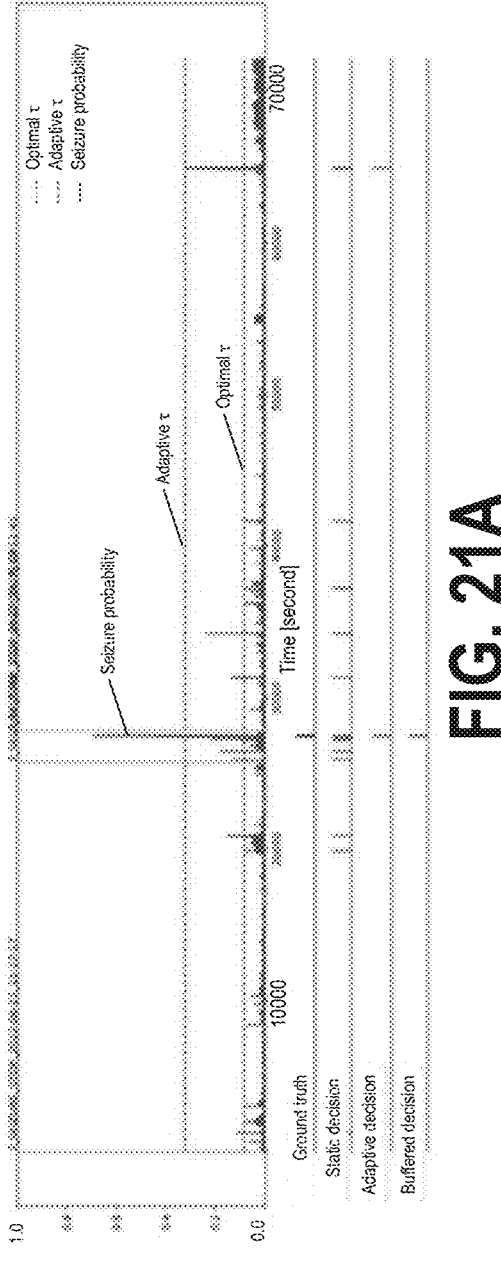
FIG. 21A-21C show a comparison of accuracy of detection algorithms that use different thresholding techniques.
Figure 21B:
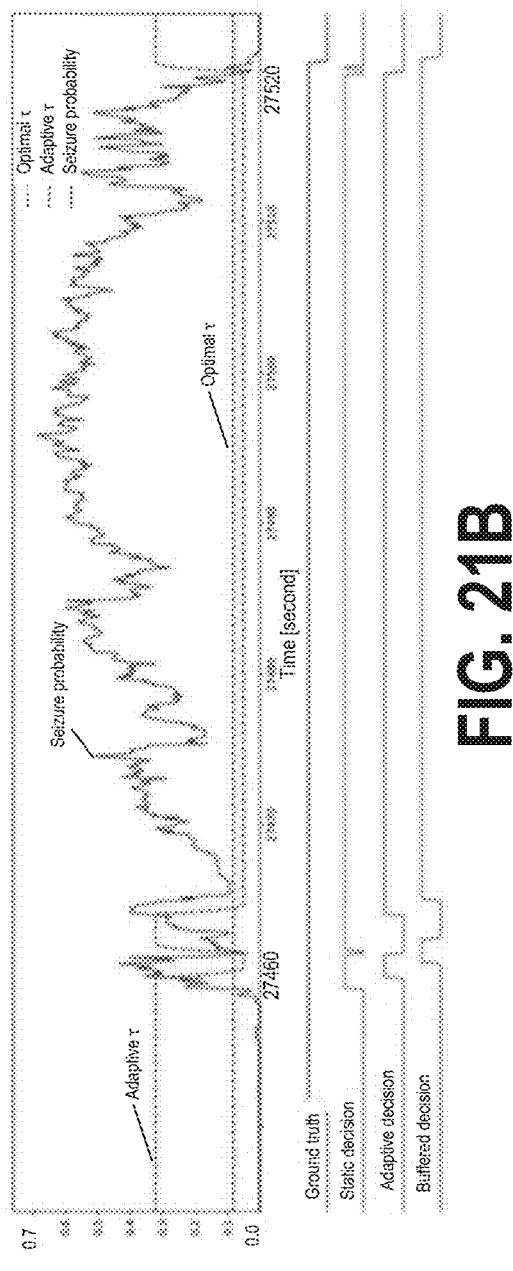
Figure 21C:
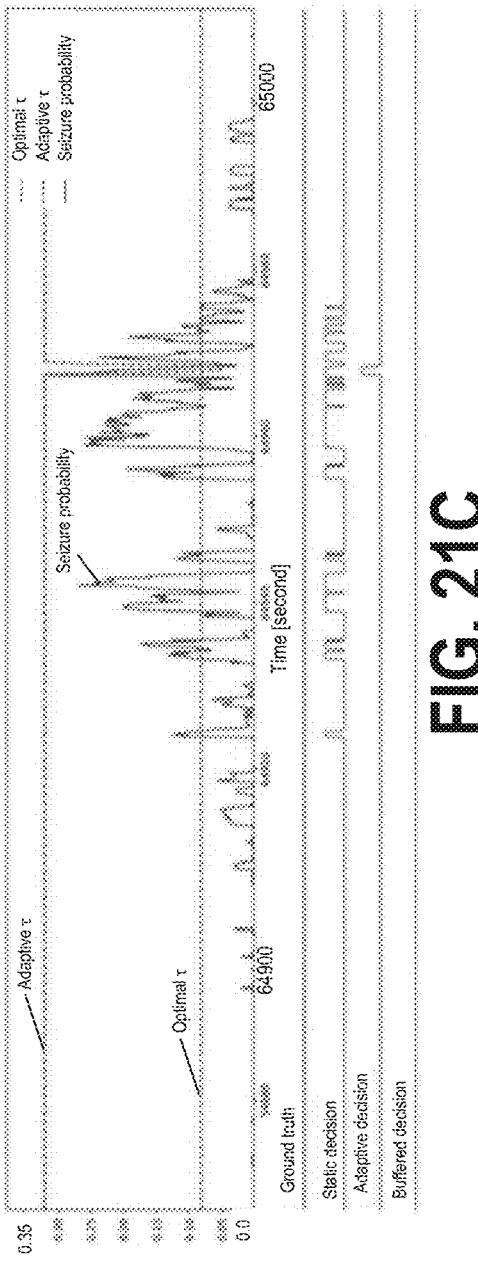

FIG. 21A shows comparison of Ground Truth (first row), Static Thresholding (second row), median-filtered Adaptive Thresholding (third row), and the Buffered Decision (fourth row). The non-thresholded decision output is shown and labeled "seizure probability", the static threshold is shown with a dotted line and labeled "optimal T", and the adaptive threshold is shown with a dotted line and labeled "adaptive T". As shown, the static thresholding technique results in more false alarm detections than the adaptive thresholding technique. FIG. 21B shows the same data as FIG. 21A, but zoomed in on the detected seizure. As shown, there is one instance of a false alarm seizure detection using the adaptive threshold. FIG. 21C shows the same data as FIG. 21A, but zoomed in on the false alarm decision of the adaptive thresholding. Table 7 below shows performance metrics of the different thresholding methods. Table 7 shows a that for adaptive thresholding, there is a slight drop in sensitivity and Event Detection Quality as a result of the minor temporal delay of the detection arising from the adaptiveness of the threshold and the subsequent temporal filtering. However, this effect is negligible compared to the gain in the Precision and the False Alarm Rate.

of threshold levels, from 0 to 1, with 0.01 increments) to convert them into a yes-no decision/outcome. Each of these evaluations gives a digital (yes-no, or 1-0) output ("decision") to indicate whether the evaluated signal segments are seizures or not. These digital time-series can then be scored against a ground truth, to obtain performance measures of the given threshold, for example such as sensitivity, specificity, and/or many others. For finding an optimal threshold setting (or desired threshold setting), there is an inherent tradeoff in balancing between maximizing sensitivity and specificity (or similar measures), for example because: (I) a higher threshold(s) will result in a lower number of false detections (high specificity), but may miss real seizures (low sensitivity), while (II) lower thresholds will result in many false alarms (the random fluctuation of the detector output will cross the lower threshold—low specificity), but will more likely find the seizure (high sensitivity). In some implementations, there may be an optimal threshold level, or a range of desirable threshold levels, where the tradeoff

TABLE 7

| | True Positive | False Negative | False Positive | True Negative | Sensitivity | Specificity | Precision | F1-Score | Event Detection Quality | False Alarm Rate |
|---|---|---|---|---|---|---|---|---|---|---|
| Optimal Static Threshold | 607 | 90 | 278 | 720802 | 0.871 | 1.000 | 0.686 | 0.767 | 0.784 | 1.397 |
| Adaptive Threshold | 575 | 122 | 10 | 721070 | 0.825 | 1.000 | 0.983 | 0.897 | 0.757 | 0.050 |
| Median-filteredadaptive thresholded decisions ('Buffered Decision') | 572 | 125 | 3 | 721077 | 0.821 | 1.000 | 0.995 | 0.899 | 0.720 | 0.000 |

10.5 A Simplified Method of Adjusting Threshold Boundaries

Figure 21D:
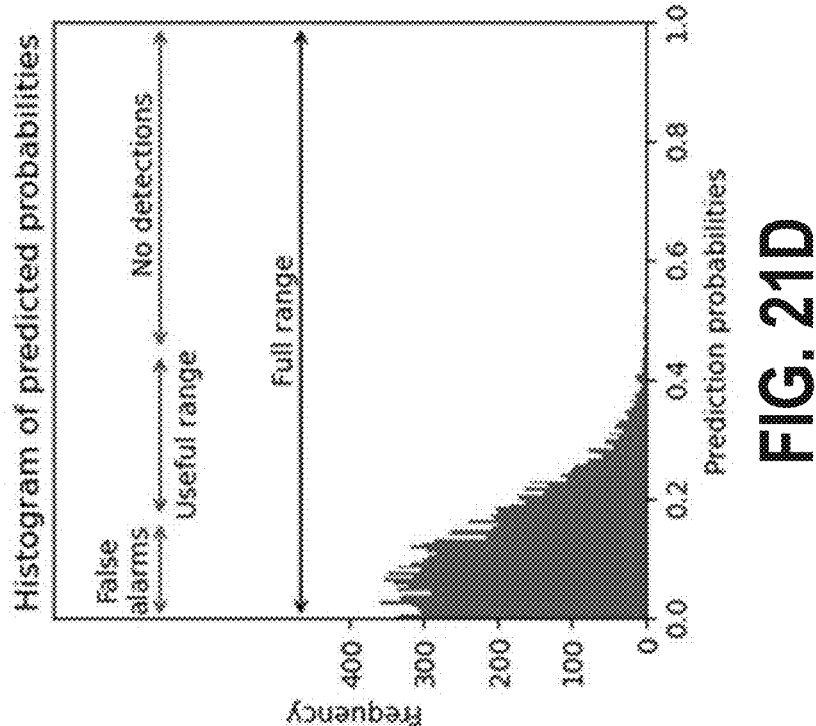
FIG. 21D is a histogram of seizure-probabilities showing the meaningful range of threshold values to detect a seizure.

In some embodiments, after the model has been trained, a threshold or threshold limits of Adaptive Thresholding (i.e., a decision boundary) may be determined. The threshold may separate the predicted continuous seizure probabilities into a binary decision between baseline and seizure. FIG. 21 depicts the meaningful range of threshold values across seizure-probabilities. As shown in FIG. 21D, the threshold can be selected on the [0, 1] range, with a tradeoff (i) between specificity and sensitivity or (ii) between event-related metrics (i.e., a value(s) falling between the "EventDetectionRate" and "FalseAlarmRate") or (iii) between other metrics that are changing their values inversely to each other if the threshold is altered. A majority of the predicted probabilities between [0, 1] lead to bad detector performance. For example, predicted probabilities can lead to too high of a threshold(s) such that no seizures are detected (e.g., labeled "No detections") or too low of a threshold(s) causing a high false alarm rate (e.g., labeled "False alarm"). The embodiments described herein may allow the user to set a preference in the above-mentioned tradeoff between event-based metrics, and in response, the algorithm may output to the user a balanced threshold value in the meaningful range of threshold values (e.g., labeled "useful range").

In some embodiments, a trained model's output (which may be, for example, an analog metric having a value anywhere between 0 and 1) is or includes a time-series of likelihoods that the given evaluated signal segments are a seizure(s) (as opposed to not a seizure(s)). This analog time-series can be iteratively thresholded with incremental threshold levels, with a certain resolution (e.g., in 100 steps between these two types of inversely behaving metrics are ideal (for the optimal case) or at least acceptable (for the desirable range case). This balancing of sensitivity and specificity can be used to determine an upper limit of the dynamic thresholding, where the threshold level sits between seizures and waits for a seizure to happen. The foregoing can be distinguished from the lower limit of the dynamic threshold, which indicates how low this threshold level may go once a seizure is detected with the high-limit threshold. This latter (i.e., the dynamic adjusting of this trade-off based pre-optimized threshold) can make the detector 'sticky'—in other words, once it detects a seizure, it may be tuned such that it is more sensitive (a lower threshold), because the likelihood is relatively high that a moment classified as a seizure will be followed by a subsequent moment that is also a seizure, given that seizure moments can follow each other in series/periods, rather than randomly. This lower threshold limit can be iteratively titrated in a manner similar to that described above for the higher threshold. As such, some embodiments set forth herein can include titrating a default threshold by finding a balance between two tradeoff outcome measures, and alternatively or in addition, can include allowing the determined optimal threshold to move lower once a seizure has been detected, to ensure that more of the seizure is captured (e.g., up to the entire duration of the seizure) and that detections within the seizure are not missed.

The probabilities outside of the useful range would not result in practically meaningful detector decisions, therefore, the algorithm can output the useful range to the user and receive a user input of a prediction probability within the useful range.

In some embodiments, the user may choose desired values for specificity and sensitivity, and the algorithm may determine a useful prediction probability range based on the specificity and sensitivity chosen. In some embodiments, the user may choose a tradeoff between event-related metrics (e.g., the "EventDetectionRate" and "FalseAlarm Rate,") and the algorithm may determine the useful prediction probability range based on the tradeoff of event-related metrics. For example, the user may determine a desired balance of the EventDetectionRate with respect to the FalseAlarmRate. The algorithm may determine the useful threshold range based on the user input. In order to evaluate the effectiveness or performance of the threshold, a weighted sum of a subset of metrics (e.g., the most relevant metrics) can be calculated, and the weighted sum may be minimized.

The algorithm may determine a threshold that minimizes the below objective function:

$$-2*(1-\alpha)*EventDetectionQuality +$$

$$2*\alpha*\left(\frac{FalseAlarmDurRate}{X}+\frac{FalseAlarmRate}{Y}\right)$$

where X and Y represent the relative importance of False Alarm Duration Rate and False Alarm Rate to the Event Detection Quality, and a is a value between [0, 1] representing the user's preference of Event Detection and FalseAlarm metrics. In an example embodiment, X=40 and Y=15 can be used.

11. Method 3—Forced Artifact Inclusion in Training of Real-Time Seizure Detector Models 11.1 State of the Art The quality of a seizure detection system heavily depends on the quality and the quantity of the labeled data used for training. EEG or ECoG are the most common type of data used for seizure detection. To 'train' the seizure detector algorithms, researchers often collect continuous EEG recordings from patients with epilepsy, both during seizures (ictal periods) and non-seizure (interictal periods). Some studies use video electroencephalography (vEEG), which combines video recording with EEG, providing both visual and electrical evidence of a seizure. This method allows for more precise labeling of the onset and end of seizures. Neurologists or trained technicians manually annotate seizure events by reviewing EEG recordings. In some cases, automated algorithms pre-label the data, which are then reviewed and corrected by experts. This process in most cases involves marking only the ictal and interictal states, seizure onset, and end.

Signal artifacts are a significant challenge in EEG analysis. These may include electrical noise, muscle movements, eye blinks, or other physiological and environmental sources of interference. In the vast landscape of interictal EEG data, these artifacts appear sparsely. Consequently, when randomly sampling the interictal EEG for training a seizure classifier, there's a pronounced risk of omitting these artifacts. This omission becomes particularly problematic when certain stereotypic activities of patients produce EEG artifacts that bear resemblance to seizure activity. Currently, these artifacts are handled by:

Artifact Rejection: Simple thresholds are applied to the raw EEG signals to identify and remove epochs with extreme values likely to be caused by artifacts.
   Artifact Correction: Techniques such as Independent Component Analysis (ICA) or Common Spatial Patterns (CSP) are employed to separate the EEG signal into components, some of which can be identified as artifacts and removed.
   Robust Feature Selection: Features that are less sensitive to artifacts are chosen for the machine learning model.
   Data Augmentation: Artificially generated seizures or artifact signals can be added to the training data to make the model more robust during real-time detection.

Improving decision making algorithms performance in distinguishing artifacts from seizure patterns is a critical element of reducing false positive alarms.

11.2 Problem Definition

Seizure detectors, without appropriate training against artifacts and/or incomplete artifact removal, can generate false positive detections, compromising the efficacy and reliability of the system.

11.3 Description of Example Solution

In some embodiments, an example solution is to forcedly include a recorded patient-specific EEG library of stereotypic artifacts in the negative labelled training set instead of trying to remove these artifacts from the actual signal. The initial data acquisition of training datasets is appended with dedicated recordings of a suite of typical patient-specific artifacts, such as chewing, walking, clapping, among others. The EEG correlates of these activities are distinctly labelled as 'artifacts'. By implementing this enriched dataset, the training algorithm is compelled to include samples from each type of artifact. This ensures that all artifacts are adequately represented in the non-seizure sample set alongside the known interictal brain activity patterns. This augmentation not only enhances the classifier's accuracy but also reduces the likelihood of false positives, making the seizure detection more reliable and robust.

The proposed solution enriches the training dataset with the prevalent artifact patterns instead of attempting to remove them, acknowledging them as an occasionally naturally appearing patterns, thus forcefully training the detection model to recognize these patterns as negative samples, distinguishing them from sometimes similar seizure patterns.

11.4 Demonstration of Embodiment

Figure 22A:
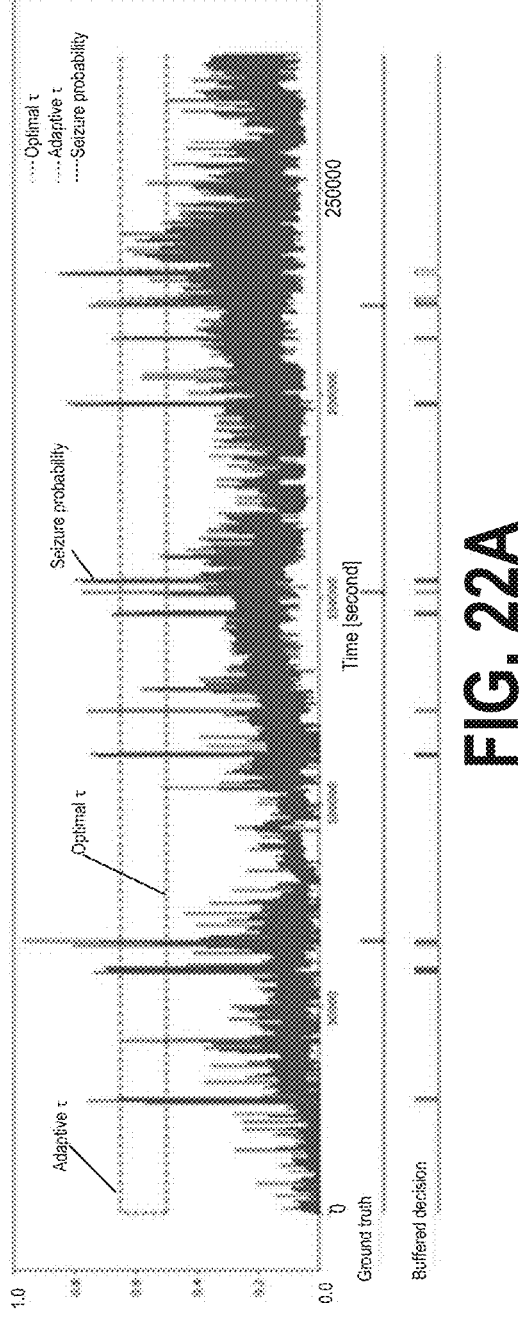
FIGS. 22A-22B shows accuracy of detection algorithms using different methods to generate training data.
Figure 22B:
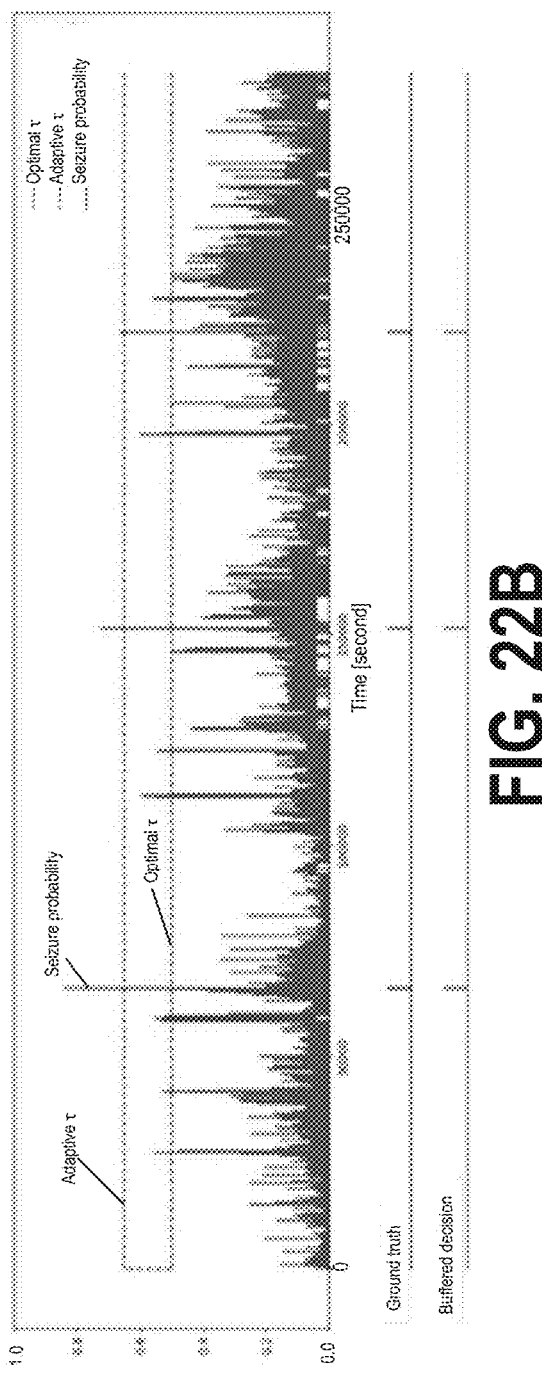

FIGS. 22A-22B show the output of the detection model (labeled "seizure probability") and the corresponding thresholded decision (bottom row) without including the recorded patient specific artifact library in the training session. Note the high number of false positive detections in the decision output (bottom row) compared to the ground truth (middle row). FIGS. 22C-22D show the output of the detection model (labeled "seizure probability") and the corresponding thresholded decision (bottom row) WITH including the recorded patient specific artifact library in the training session. Note fewer false positive detections in the decision output compared to the ground truth. Table 8 compares the detection model performance when trained without the artifact library versus with the artifact library.

TABLE 8

| Description | Training without Artifact Library | Training with Artifact Library |
|---|---|---|
| Sensitivity | 0.762 | 0.697 |
| Specificity | 0.989 | 1 |
| False Alarm Rate | 19.994 | 0 |
| Precision | 0.033 | 1 |
| F1-Score | 0.064 | 0.821 |

12. Method 4—Enriching Training Datasets with Xeno-Seizures to Improve Model Training 12.1 State of the Art:

Traditional methods of patient-specific seizure detection using EEG data often suffer from a lack of sufficient training samples. Specifically, many patients might have only a few seizure events recorded, which leads to a significant under sampling problem. This makes it challenging to train robust models that can generalize well to different types of seizures within the same patient. Data augmentation is a technique used to enhance the size and quality of training datasets by creating modified versions of the data, thus helping to reduce overfitting and improve the generalization of machine learning models. In the context of EEG data for seizure detection, data augmentation is particularly important because obtaining large datasets with a variety of seizure types and patient backgrounds can be challenging due to the rarity of events, and the labor-intensive nature of collecting and annotating this type of data. Data augmentation is usually implemented in the training of epileptic seizure detectors the following ways:

Synthetic Seizure Generation: Techniques such as Generative Adversarial Networks (GANs) can be trained to generate synthetic EEG data that mimics real seizure activity. These models can learn the complex distribution of EEG signals during seizures and produce new, artificial EEG signals that can augment the training set. Alternatively, by identifying typical seizure patterns, templates can be created and then modified with noise, time warping, or amplitude scaling to produce new seizure-like signals.

Noise Injection: Adding Gaussian noise to EEG signals can make the algorithm more robust to variations in the signal that might occur due to artifacts or other sources of interference. In addition, parts of the EEG signals can be randomly selected and erased or replaced with noise, teaching the model to handle missing or obscured data.

Time-based Transformations: The time axis of EEG signals can be slightly modified to simulate faster or slower seizure dynamics.

Frequency-based Transformations: Varying the frequency bands of signal filters to simulate differences in seizure manifestations across patients. Randomly altering the power of different frequency bands within the EEG signals can also help generating novel surrogate data.

Geometric Transformations: The order of EEG channels can be shuffled, which can help the model to not learn channel-specific features that are not generalizable.

Mixing Signals: Creating combinations of seizure and non-seizure signals by linearly combining them can help in creating ambiguous examples that can also improve the robustness of the model.

Data augmentation strategies must be carefully designed to avoid introducing biases or unrealistic features into the data. Some works use cross-patient seizure-pattern libraries to enrich the training datasets or to set up a universal detector. These approaches operate on morphing the sample signal libraries of native EEG signals or their dimension reduced versions.

12.2 Problem Definition:

Known data augmentation methods are currently lacking in that they do not use real-world, morphed seizure data to enhance the training sets for model training. The augmented data should improve the model's ability to generalize from the training data to unseen real-world data without leading to an increase in false positives or negatives. Thus, augmentation using additional real-world EEG data with preserved, realistic variance and noise may increase the model's ability to generalize.

12.3 Description of Proposed Solution

The proposed approach leverages EEG data from other patients with similar seizure feature-landmark profiles, termed 'digital seizure-siblings'. By normalizing and morphing this borrowed data to align with the target patient's EEG profile, the training dataset can be significantly enriched. This approach not only increases the number of training samples but also captures a wider realm of seizure-related brain activity, leading to a more robust seizure classifier. In some embodiments, the system 100 can implement continuous (e.g., 24/7) broadband EEG data collection; therefore, there is a growing continuous dataset of ictal and interictal recordings from multiple patients that allows increasingly precise seizure matching over time.

In addressing the challenges of training seizure classifiers, the concept of 'digital seizure-siblings' is central to the proposed solution. The concept is to augment a patient's seizure samples ('target data') with EEG data from other patients ('xeno-data') who exhibit similar EEG feature profiles. EEG data from different patients may exhibit different variances, which can be attributed to numerous external factors like the differences in recording devices, electrode placements, and more. To address this, EEG segments are first pre-processed, normalized and the signals are amalgamated into a singular 'universal channel'. Such normalization and removing the spatial aspects of a multiple channel configuration ensures that the borrowed EEG data from 'digital seizure-siblings', can be seamlessly aligned and are consistent with the target patient's data, reducing external noise and inconsistencies.

The next pivotal step is the computation of the feature-importance profile for each patient. Since model training is also specific to the negative samples, this computation is performed on a hybrid dataset containing the normalized interictal EEG segments of the actual patient whose dataset is to be enriched, and the normalized ictal (i.e., seizure) segments of the xeno-database. These profiles act as a signature, capturing the essence of EEG characteristics of a seizure the patient experiences. Then, advanced clustering or similarity learning techniques are deployed to group patients based on the resemblance of their EEG feature profiles. Similarly to matching fingerprints; for any given patient, the database can be searched to identify their 'digital seizure-siblings', ensuring that the borrowed data closely mirrors their own EEG patterns.

Next the selected datasets to be used for enriching ('xeno-data') is morphed to match the target-data in terms of the distribution of the feature values. The term 'morphing' refers to fine-tuning and alignment of the 'digital seizure-siblings' feature data to fit the distribution of the target patient's feature data. Importantly, this morphing is done separately for both seizure and non-seizure feature samples. In most cases a Gaussian mixture model is aligned on every distribution and the individual gaussians are morphed to match the target datasets gaussians. Techniques rooted in domain adaptation or transfer learning are used to perform this step, ensuring that the enriched data set truly reflects the target patient's EEG landscape.

It should be appreciated that since the detector model is taking the derived features as inputs, the morphing of the xeno-data should be performed also on the feature domain, rather than on the raw EEG signal domain. Theoretically the concept can be resembled by skewing, scaling, and shifting a distribution with two distinguishable peaks of the xeno-data to overlap with a similar two-peaked distribution of the target data. Then, the actual values of the dataset are transformed based on the morphing factors of the distributions.

Lastly, to streamline the input for the model, a 'universal channel' is used. Instead of juggling multiple EEG channels, they are amalgamated into a singular 'universal channel'. This step retains the overall importance of EEG features but eliminates the spatial specificity of where specific features originated, offering a consistent and simplified data input to the model (see FIG. 23). Alternatively, the 'channel-order' of the xeno-features can be reshuffled to match the channel importance of the target data, thus preserving the spatial distribution and profile of the dataset. In a two-stage detector embodiment, the first screening detector may operate based on a training with enriched data, either as a multichannel or as a universal single-channel detector, and a second 'verifying' stage can be trained solely on patient-specific data.

12.4 Operation

Steps:
1. Collect EEG data from a diverse set of patients.
2. Preprocess and normalize EEG data to remove variance introduced by external factors.
3. Merge all EEG channels into a single 'universal channel', ensuring the data input is consistent.
4. Train a detector with the given xeno-seizure and the actual patient's interictal EEG data. Extract features and compute the feature-importance profile for each patient.
5. Cluster or group patients based on the similarity of their feature-importance profiles.
6. For a target patient, identify 'digital seizure-siblings' from the clusters.
7. Morph the EEG data distributions of these 'digital seizure-siblings' to align with the target patient's EEG data distribution using domain adaptation techniques.
8. Train the seizure classifier using the enriched dataset.
9. Evaluate the model using appropriate metrics (e.g., sensitivity, specificity, AUC-ROC, or any metric of similar purpose and refine as necessary.

Figure 23A:
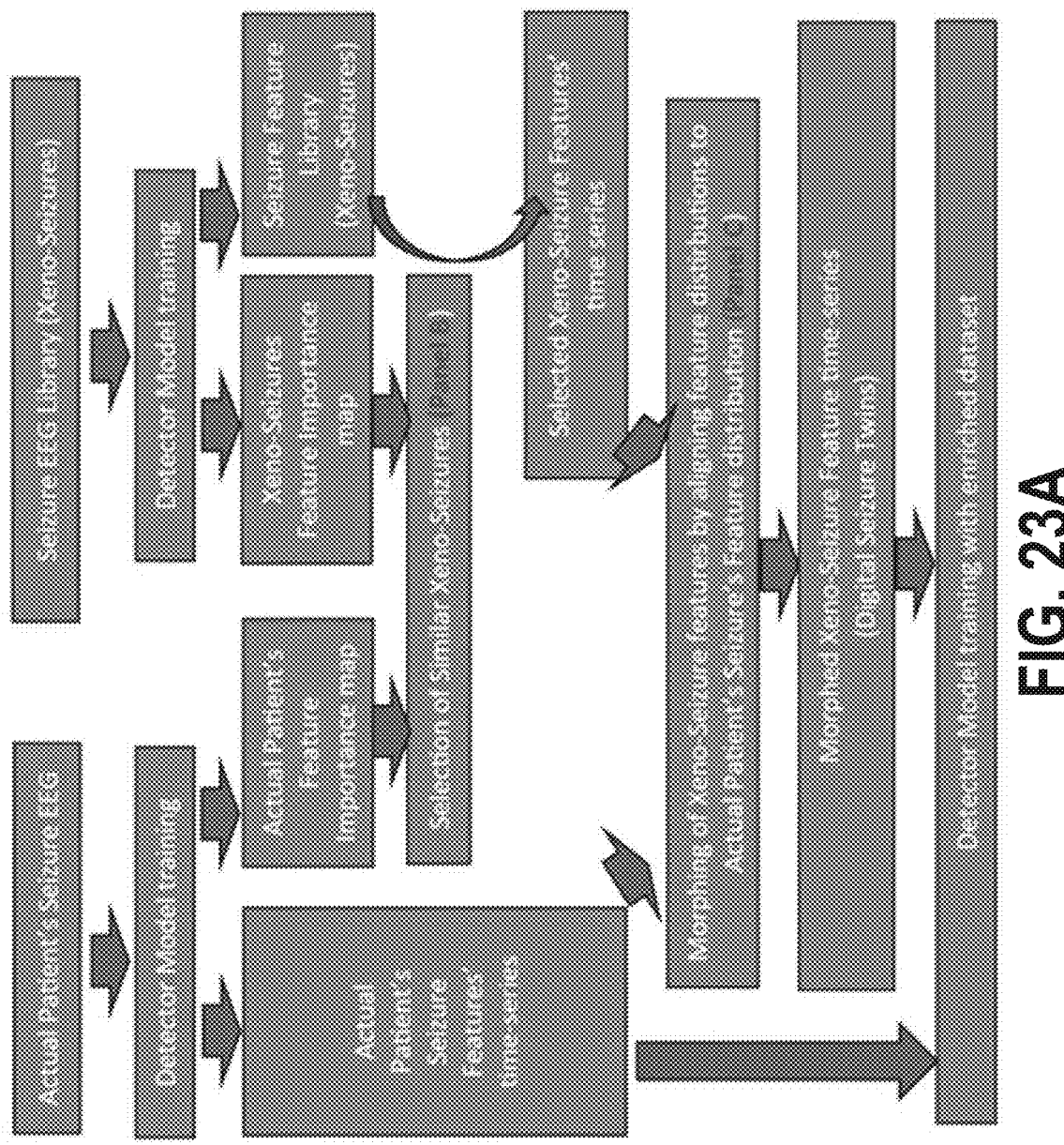
FIG. 23A shows an example processing pipeline to enrich a training dataset using Xeno-Seizure data.
Figures 23B, 23C:
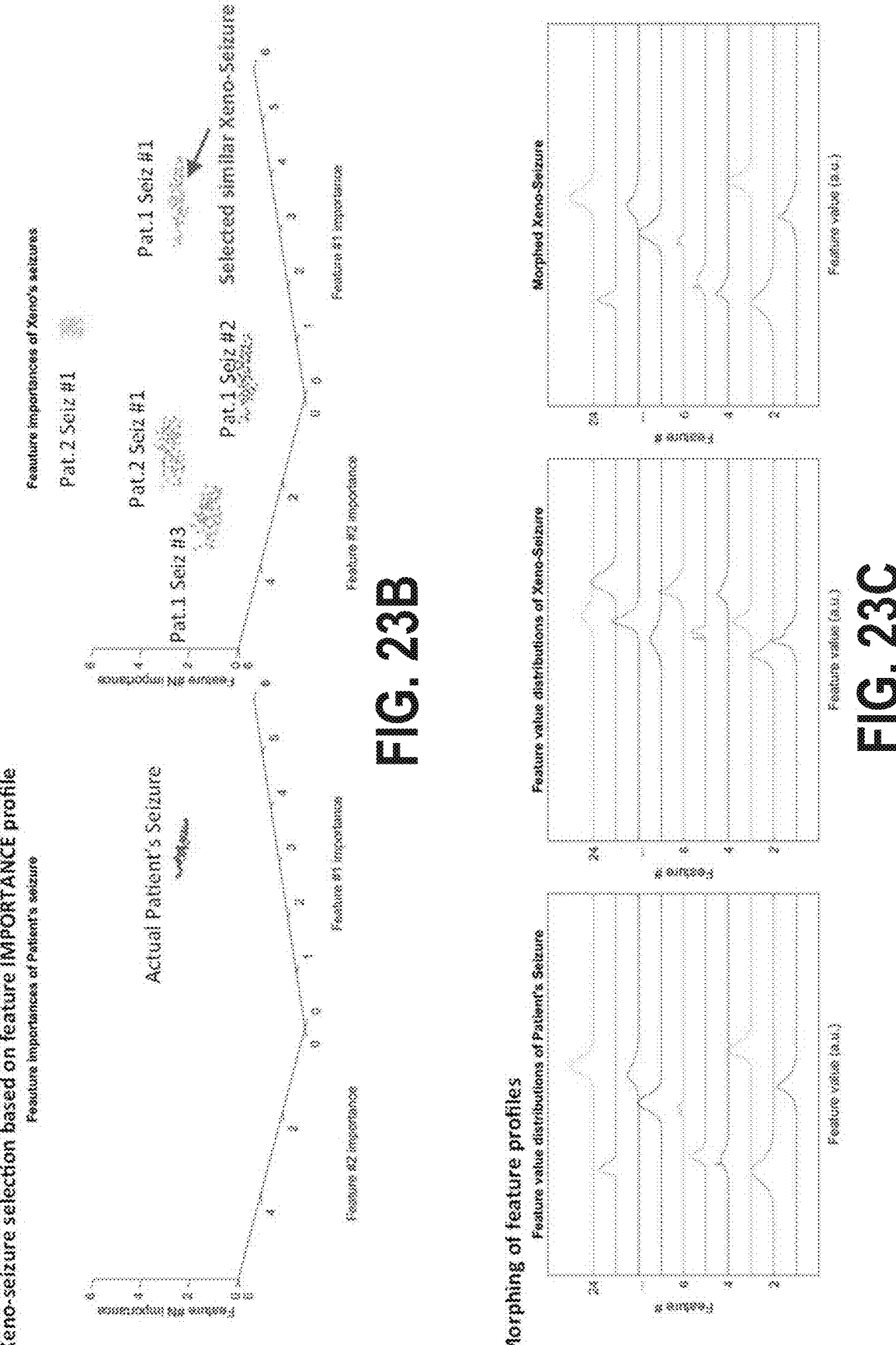
FIG. 23B-23C shows steps of Xeno-Seizure selection and morphing.
Figure 24:
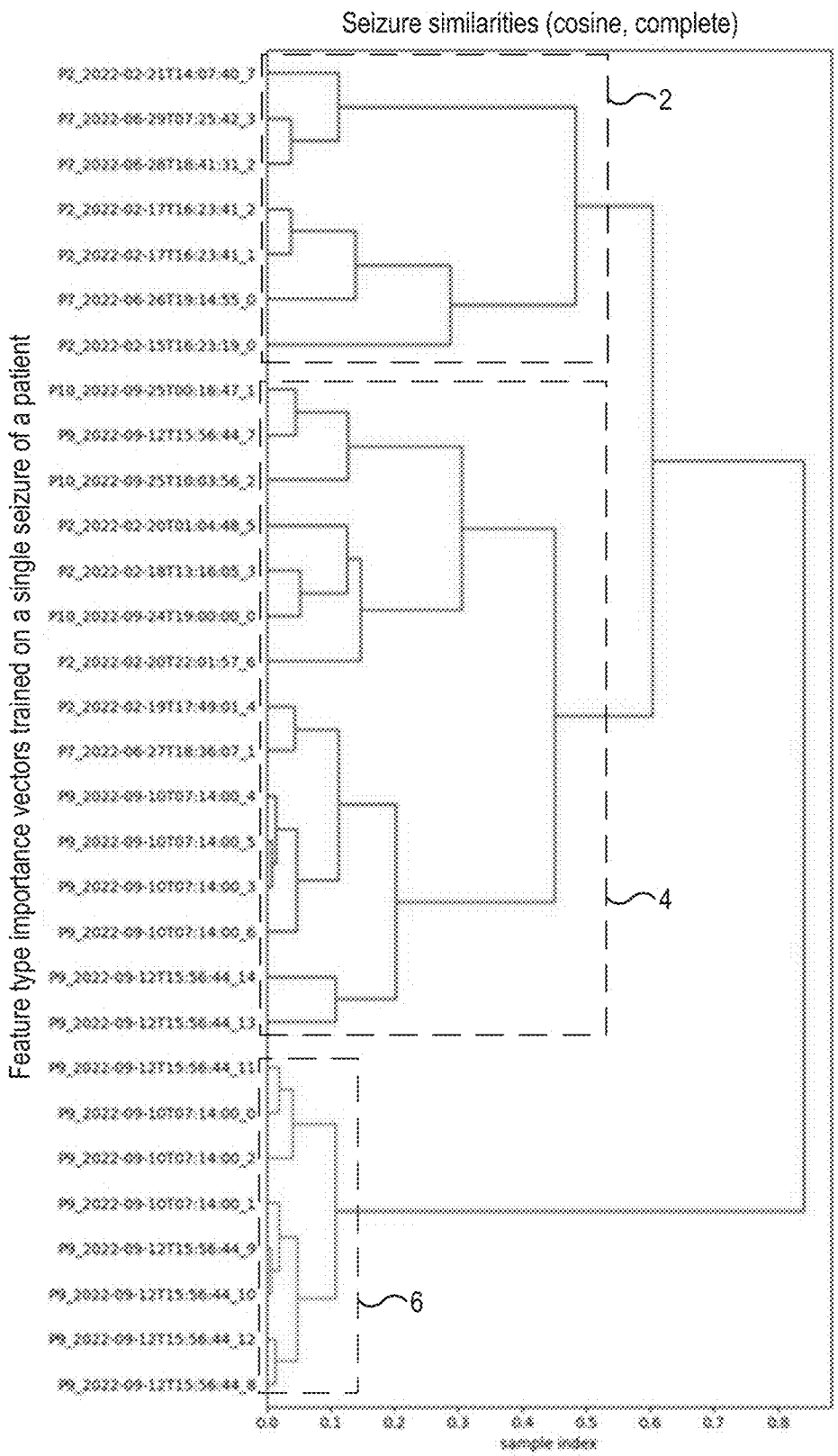
FIG. 24 shows clustering of seizures based on the similarities of their Feature Importance maps.

FIG. 23A shows an example processing pipeline for data enrichment by generating digital seizure siblings by morphing xeno-seizures, according to an embodiment. FIG. 23B-23C shows steps of Xeno-seizure selection and morphing. As shown in FIG. 23B, a detector model is trained for all seizures one-by-one against interictal and artifact activity, resulting in feature importance profiles for each seizure. Xeno seizures displaying similar feature importance profile with the actual patient's feature importance profile are selected for data enriching (augmentation). As shown in FIG. 23C, the feature value distributions of the selected Xeno seizure are morphed onto the actual patient's feature value distributions by scaling the mean, variance and average amplitude of the distributions. The morphed feature values of the xeno-seizures are then included in the training dataset of the actual patient. FIG. 24 shows clustering of seizures based on the similarities of their Feature Importance maps. As shown, seizure events (labeled along the y-axis) are grouped into similarity groups 2, 4, 6. Patients can be identified from the first two characters of the labels on the y-axis (P2—Patient #2; P7—Patient #7, etc.).

12.5 Demonstration of Embodiment

The concept of 'digital seizure-siblings' helps to enrich the training dataset ultimately resulting in more accurate seizure detection. By identifying and leveraging EEG data from other patients with similar seizure profiles, the challenge of under-sampling in patient-specific training dataset can effectively be addressed. This approach goes beyond traditional data augmentation techniques which build on the controlled distortion of existing data in focus and instead offers a more holistic and patient-centric method to improve seizure classifier robustness. The proposed solution combines the concept of 'digital seizure-siblings' with morphing EEG data distributions, offering a patient-specific approach to seizure classification that diverges from traditional methodologies.

In some embodiments, a system includes a plurality of electrodes, a memory, and one or more processors. The plurality of electrodes is configured for implantation in a patient and configured to measure a brain activity of the patient. The one or more processors are operatively coupled to the memory and the plurality of electrodes, and are configured to: (1) receive brain activity data from the plurality of electrodes, (2) detect an onset of a seizure based on the brain activity data, (3) determine, based on a pattern in the brain activity data, a timing with which to deliver current pulses to a brain of the patient to disrupt at least one oscillation in brain activity contributing to the seizure, and (4) activate a subset of electrodes from the plurality of electrodes to deliver the current pulses to a target region of the brain of the patient according to the timing.

In some implementations, the brain activity data includes electroencephalography (EEG) data.

In some implementations, a subset of electrodes from the plurality of electrodes is implanted in one of a subgaleal space of the patient, a subdural space of the patient, an epidural space of the patient, or the brain of the patient.

In some implementations, the plurality of electrodes is configured to deliver Intersectional Short-Pulse (ISP) stimulation to disrupt the at least one oscillation in brain activity contributing to the seizure.

In some implementations, the one or more processors is configured to determine the timing based on at least one of a phase or a frequency of the brain activity data, and to activate the subset of electrodes to deliver the current pulses one of immediately or after a predetermined delay, and with a predefined frequency.

In some implementations, the one or more processors is further configured to recognize the pattern of brain activity, the one or more processors is configured to activate the subset of electrodes to deliver the current pulses one of immediately or after a predetermined delay, the one or more current pulses configured to align with an inherent rhythmicity of the brain activity data.

In some implementations, the system also includes a sensor configured to measure biosignal data associated with the patient, the one or more processors configured to detect a precursor activity leading to a seizure, the onset of the seizure, or a presence of the seizure further based on the biosignal data. The one or more sensors can be configured to measure at least one of electromyography (EMG) data, electrocardiogram (ECG) data, or heart rate.

In some implementations, the one or more processors is further configured to quantify the pattern in the brain activity data by calculating a measure of rhythmicity at predetermined frequency components of the brain activity data.

In some implementations, the system also includes a communication interface configured to transfer information between the one or more processors and an external device, and the external device is configured to train a model for detecting a precursor activity leading to a seizure, the onset of the seizure, or a presence of the seizure, the model configured to be executed by the one or more processors.

The model can be trained using datasets including ictal EEG data and non-ictal EEG data from at least one of the patient or another patient.

In some embodiments, an implantable neurostimulator device includes a memory and a processor operatively coupled to the memory, the processor configured to be electrically coupled to a plurality of electrodes implanted in a patient, and also configured to: (1) receive brain activity data from the plurality of electrodes, (2) detect a precursor activity leading to a seizure, the onset of the seizure, or a presence of the seizure based on the brain activity data, (3) determine a timing with which to deliver current pulses to the brain of the patient to interfere with at least one oscillation in brain activity contributing to the seizure by calculating a measure of rhythmicity of the brain activity data, and (4) activate a subset of electrodes from the plurality of electrodes to deliver the current pulses to the region of the brain of the patient based on the timing.

In some implementations, the brain activity data includes electroencephalography (EEG) data.

In some implementations, at least a subset of electrodes from the plurality of electrodes is implanted in one of a subgaleal space of the patient, a subdural space of the patient, an epidural space of the patient, or the brain of the patient.

In some implementations, the plurality of electrodes is configured to deliver Intersectional Short-Pulse (ISP) stimulation, and each of the current pulses has an amplitude of about 0.1 milliamps (mA) to about 80 mA.

In some implementations, the one or more processors is configured to determine the timing based on one of the measure of rhythmicity in the brain activity data or a feature of the rhythmicity in the brain activity data, and to activate the subset of electrodes to deliver the current pulses one of immediately or after a predetermined delay, and with a predefined frequency.

In some implementations, the one or more processors is further configured to recognize a pattern of brain activity, the one or more processors is configured to activate the subset of electrodes to deliver the current pulses one of immediately or after a predetermined delay, the one or more current pulses configured to align with an inherent rhythmicity of the brain activity data.

In some implementations, the implantable neurostimulator device also includes one or more sensors configured to measure biosignal data associated with the patient, the one or more processors configured to detect the precursor activity leading to the seizure, the onset of the seizure, or the presence of the seizure further based on the biosignal data.

In some embodiments, a method includes measuring brain activity data associated with a brain of a patient using a plurality of electrodes implanted in the patient, and detecting an onset of a seizure based on the brain activity data. The method also includes determining a timing with which to deliver electrical stimulation to the brain of the patient to disrupt oscillations in brain activity contributing to the seizure, by analyzing oscillations in the brain activity data. The method also includes causing, in response to detecting a precursor activity leading to a seizure, an onset of the seizure, or the presence of the seizure, delivery of electrical stimulation to the brain of the patient via at least a subset of electrodes from the plurality of electrodes and according to the timing.

In some implementations, the brain activity data includes electroencephalography (EEG) data collected from a plurality of EEG channels. In some implementations, the method also includes applying a filter to each of the EEG channels, and generating a virtual channel by calculating a weighted average of the EEG channels.

In some implementations, the method also includes applying a sliding window to the EEG channels and the virtual channel to produce windowed EEG channels and a windowed virtual channel, and calculating features for each of the windowed EEG channels and the windowed virtual channel based on a predefined time interval.

The features can include at least one of time domain features, frequency domain features, spatial features, or temporal dynamic features.

Alternatively, the features can include at least one of a root mean square, a line length, a variance, a kurtosis, a Hjorth mobility, a Hjorth complexity, a wavelet transform, a mutual information, a mean coherence, a standard deviation of mean phase delay, a recurrence rate, a determinism, an entropy, or an averaged diagonal line length.

In some implementations, the method also includes inputting the features to a regressive decision tree trained using EEG data from the patient or EEG data from at least one other patient, averaging outputs of the regressive decision trees to produce an averaged output; and comparing the averaged output to a dynamic threshold that is updated based on previous outputs of a classification model.

In some embodiments, a method includes calculating one or more features based on brain activity recorded from each electrode of a plurality of electrodes implanted in a patient. The method also includes inputting at least one of (1) the one or more features, or (2) at least a portion of the recorded brain activity into a model trained using brain activity data from at least one of the patient or at least one other patient. The method also includes determining a range of effective prediction probability threshold values and selecting a threshold value from the range of effective prediction probability threshold values, and comparing an output of the model to the threshold value. The method also includes, in response to determining the output crosses the threshold value, determining a timing and a subset of electrodes with which to deliver electrical pulses. The method also includes causing delivery of the electrical pulses to the brain of the patient via at least the subset of electrodes and according to the timing.

The determining the range of effective prediction probability threshold values can be based on balancing between performance metrics from at least one pair of performance metrics, each pair of performance metrics from the at least one pair of performance metrics having the property that improving one performance metric from that pair of performance metrics results in a diminishing of the other.

The one or more features can include a mutual information between one or more pairs of electrodes, the determining the mutual information between each of the one or more pairs of electrodes optionally including (1) computing covariances between signals from a given pair of electrodes to generate a first value, (2) normalizing the first value by multiplying the first value by a product of the variances of the signals from the given pair of electrodes to generate a second value $r_{sq}$, and (3) calculating a logarithm of $(1-r_{sq})$.

The computing the one or more features can include performing recurrence quantification analysis (RQA) without using a recurrence plot matrix.

In some implementations, the one or more features includes cross-channel coherence, and the determining the cross-channel coherence includes, for each frequency component: (1) applying a frequency-specific sine kernel convolution or by applying Discrete Fourier Transform (DFT) to the brain activity signal of each electrode from the plurality of electrodes to generate frequency-specific coherence values or the frequency spectrum of the signal, (2) calculating relevant cross-coherence values from the frequency-specific coherence values or via cross spectrum calculation, and (3) storing only the relevant cross-channel coherences in an array before moving to the next frequency.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. While the embodiments have been particularly shown and described, it will be understood that various changes in form and details may be made.

Although various embodiments have been described as having particular features and/or combinations of components, other embodiments are possible having a combination of any features and/or components from any of embodiments as discussed above.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

In this disclosure, references to items in the singular should be understood to include items in the plural, and vice versa, unless explicitly stated otherwise or clear from the context. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth. The use of any and all examples, or exemplary language ("e.g.," "such as," "including," or the like) provided herein, is intended merely to better illuminate the embodiments and does not pose a limitation on the scope of the embodiments or the claims.

Some embodiments and/or methods described herein can be performed by software (executed on hardware), hardware, or a combination thereof. The use of the term "module" may encompass hardware components, software components (executed on hardware), or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

The invention claimed is:

1. A system, comprising:
a plurality of electrodes configured for implantation in a patient and configured to measure a brain activity of the patient;
a memory; and
one or more processors operatively coupled to the memory and the plurality of electrodes, the one or more processors configured to:
receive brain activity data from the plurality of electrodes;
detect an onset of a seizure based on the brain activity data;
identify a pattern in the brain activity data based on mutual information between one or more pairs of electrodes from the plurality of electrodes, the mutual information determined, at least in part, by:
computing covariances between signals from the one or more pairs of electrodes from the plurality of electrodes,
generating a first value based on the covariances,
normalizing the first value to generate a second value $r_{sq}$, and
calculating a logarithm of $(1-r_{sq})$;
determine, based on the pattern in the brain activity data, a timing with which to deliver current pulses to a brain of the patient to disrupt at least one oscillation in brain activity contributing to the seizure; and activate a subset of electrodes from the plurality of electrodes to deliver the current pulses to a target region of the brain of the patient according to the timing.

2. The system of claim 1, wherein the brain activity data includes electroencephalography (EEG) data.

3. The system of claim 1, wherein a subset of electrodes from the plurality of electrodes is implanted in one of a subgaleal space of the patient, a subdural space of the patient, an epidural space of the patient, or the brain of the patient.

4. The system of claim 1, wherein the plurality of electrodes is configured to deliver Intersectional Short-Pulse (ISP) stimulation to disrupt the at least one oscillation in brain activity contributing to the seizure.

5. The system of claim 1, wherein the one or more processors is configured to determine the timing based on at least one of a phase or a frequency of the brain activity data, and to activate the subset of electrodes to deliver the current pulses one of immediately or after a predetermined delay, and with a predefined frequency.

6. The system of claim 1, wherein the one or more processors is further configured to activate the subset of electrodes to deliver the current pulses one of immediately or after a predetermined delay, the one or more current pulses configured to align with an inherent rhythmicity of the brain activity data.

7. The system of claim 1, further comprising:
a sensor configured to measure biosignal data associated with the patient, the one or more processors configured to detect a precursor activity leading to a seizure, the onset of the seizure, or a presence of the seizure further based on the biosignal data.

8. The system of claim 7, wherein the sensor is configured to measure at least one of electromyography (EMG) data, electrocardiogram (ECG) data, or heart rate.

9. The system of claim 1, wherein the one or more processors is further configured to quantify the pattern in the brain activity data by calculating a measure of rhythmicity at predetermined frequency components of the brain activity data.

10. The system of claim 1, further comprising:
a communication interface configured to transfer information between the one or more processors and an external device,
the external device configured to train a model for detecting a precursor activity leading to a seizure, the onset of the seizure, or a presence of the seizure, the model configured to be executed by the one or more processors.

11. The system of claim 10, wherein the model is trained using datasets including ictal EEG data and non-ictal EEG data from at least one of the patient or another patient.

12. An implantable neurostimulator device, comprising:
a memory; and
a processor operatively coupled to the memory, the processor configured to be electrically coupled to a plurality of electrodes implanted in a patient, the processor configured to:
receive brain activity data from the plurality of electrodes;
detect a precursor activity leading to a seizure, an onset of the seizure, or a presence of the seizure based on the brain activity data;
identify a pattern in the brain activity data based on mutual information between one or more pairs of electrodes from the plurality of electrodes, the mutual information determined, at least in part, by:

computing covariances between signals from the one or more pairs of electrodes from the plurality of electrodes, generating a first value based on the covariances, normalizing the first value to generate a second value $r_{sq}$, and calculating a logarithm of $(1-r_{sq})$;

determine a timing with which to deliver current pulses to a brain of the patient to interfere with at least one oscillation in brain activity contributing to the seizure based on the pattern in the brain activity data; and activate a subset of electrodes from the plurality of electrodes to deliver the current pulses to a target region of the brain of the patient based on the timing.

13. The implantable neurostimulator device of claim 12, wherein the brain activity data includes electroencephalography (EEG) data.

14. The implantable neurostimulator device of claim 12, wherein at least a subset of electrodes from the plurality of electrodes is implanted in one of a subgaleal space of the patient, a subdural space of the patient, an epidural space of the patient, or the brain of the patient.

15. The implantable neurostimulator device of claim 12, wherein the plurality of electrodes is configured to deliver Intersectional Short-Pulse (ISP) stimulation, and each of the current pulses has an amplitude of about 0.1 milliamps (mA) to about 80 mA.

16. The implantable neurostimulator device of claim 12, wherein the processor is configured to determine the timing based on one of a measure of rhythmicity in the brain activity data or a feature of the rhythmicity in the brain activity data, and to activate the subset of electrodes to deliver the current pulses one of immediately or after a predetermined delay, and with a predefined frequency.

17. The implantable neurostimulator device of claim 12, wherein the processor is further configured to activate the subset of electrodes to deliver the current pulses one of immediately or after a predetermined delay, the current pulses configured to align with an inherent rhythmicity of the brain activity data.

18. The implantable neurostimulator device of claim 12, further comprising:

one or more sensors configured to measure biosignal data associated with the patient, the processor configured to detect the precursor activity leading to the seizure, the onset of the seizure, or the presence of the seizure further based on the biosignal data.

19. A method, comprising:

measuring brain activity data associated with a brain of a patient using a plurality of electrodes implanted in the patient;

detecting a precursor activity leading to a seizure, an onset of the seizure, or a presence of the seizure based on the brain activity data;

identifying a pattern in the brain activity data based on mutual information associated with the plurality of electrodes, the mutual information determined, at least in part, by:

computing covariances between signals associated with the plurality of electrodes, generating a first value based on the covariances, normalizing the first value to generate a second value $r_{sq}$, and calculating a logarithm of $(1-r_{sq})$;

determining, based on the pattern in the brain activity data, a timing with which to deliver electrical stimulation to the brain of the patient to disrupt oscillations in brain activity contributing to the seizure; and in response to detecting the precursor activity leading to a seizure, the onset of the seizure, or the presence of the seizure, causing delivery of electrical stimulation to the brain of the patient via at least a subset of electrodes from the plurality of electrodes and according to the timing.

20. The method of claim 19, wherein the brain activity data includes electroencephalography (EEG) data collected from a plurality of EEG channels.

21. The method of claim 20, further comprising:

applying a filter to each EEG channel from the plurality of EEG channels; and generating a virtual channel by calculating a weighted average of the plurality of EEG channels.

22. The method of claim 21, further comprising:

applying a sliding window to the plurality of EEG channels and the virtual channel to produce windowed EEG channels and a windowed virtual channel; and calculating features for each of the windowed EEG channels and the windowed virtual channel based on a predefined time interval.

23. The method of claim 22, wherein the features include at least one of time domain features, frequency domain features, spatial features, or temporal dynamic features.

24. The method of claim 22, wherein the features include at least one of a root mean square, a line length, a variance, a kurtosis, a Hjorth mobility, a Hjorth complexity, a wavelet transform, a mutual information, a mean coherence, a standard deviation of mean phase delay, a recurrence rate, a determinism, an entropy, or an averaged diagonal line length.

25. The method of claim 24, further comprising:

inputting the features to a regressive decision tree trained using EEG data from the patient or EEG data from at least one other patient;

averaging outputs of the regressive decision trees to produce an averaged output; and comparing the averaged output to a dynamic threshold that is updated based on previous outputs of a classification model.

26. A method, comprising:

calculating one or more features based on brain activity recorded from each electrode of a plurality of electrodes implanted in a patient, the one or more features including mutual information between one or more pairs of electrodes from the plurality of electrodes, the mutual information identified, at least in part, by:

computing covariances between signals associated with the one or more pairs of electrodes, generating a first value based on the covariances, normalizing the first value to generate a second value $r_{sq}$, and calculating a logarithm of $(1-r_{sq})$;

inputting at least one of (1) the one or more features, or (2) at least a portion of the recorded brain activity into a model trained using brain activity data from at least one of the patient or at least one other patient, determining a range of effective prediction probability threshold values and selecting a threshold value from the range of effective prediction probability threshold values;

comparing an output of the model to the threshold value;

in response to determining the output crosses the threshold value, determine a timing and a subset of electrodes with which to deliver electrical pulses; and causing delivery of the electrical pulses to a brain of the patient via at least the subset of electrodes and according to the timing.

27. The method of claim 26, wherein the determining the range of effective prediction probability threshold values is based on balancing between performance metrics from at least one pair of performance metrics, each pair of performance metrics from the at least one pair of performance metrics having the property that improving one performance metric from that pair of performance metrics results in a diminishing of the other.

28. The method of claim 26, wherein the computing the one or more features includes:

performing recurrence quantification analysis (RQA) without using a recurrence plot matrix.

29. The method of claim 26, wherein the one or more features includes cross-channel coherence, the determining the cross-channel coherence includes, for each frequency component:

applying a frequency-specific sine kernel convolution or applying Discrete Fourier Transform (DFT) to a brain activity signal of each electrode from the plurality of electrodes to generate frequency-specific coherence values or a frequency spectrum of the brain activity signal;

calculating relevant cross-coherence values from the frequency-specific coherence values or via cross spectrum calculation; and storing only relevant cross-channel coherences in an array before moving to a subsequent frequency.

* * * * *